(12) United States Patent
Chinnaiyan et al.

(10) Patent No.: US 7,597,890 B2
(45) Date of Patent: Oct. 6, 2009

(54) METHODS AND COMPOSITIONS FOR DIAGNOSING LUNG CANCER

(75) Inventors: Arul Chinnaiyan, Plymouth, MI (US); David Beer, Chelsea, MI (US); Guoan Chen, Ann Arbor, MI (US); Xiaoju Wang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 11/715,642

(22) Filed: Mar. 8, 2007

(65) Prior Publication Data

US 2008/0044839 A1 Feb. 21, 2008

Related U.S. Application Data

(63) Continuation-in-part of application No. 11/145,861, filed on Jun. 6, 2005.

(60) Provisional application No. 60/578,406, filed on Jun. 9, 2004.

(51) Int. Cl.
*A61K 39/395* (2006.01)

(52) U.S. Cl. .................................. 424/133.1; 530/387.1

(58) Field of Classification Search ........................ None
See application file for complete search history.

(56) References Cited

U.S. PATENT DOCUMENTS

| | | |
|---|---|---|
| 6,610,508 B1 | 8/2003 | Hentze et al. |
| 6,686,147 B1 | 2/2004 | Scanlan et al. |
| 6,783,961 B1 | 8/2004 | Edwards et al. |
| 6,943,241 B2 | 9/2005 | Isogai et al. |
| 7,115,416 B1 | 10/2006 | Edwards et al. |
| 7,205,117 B1 | 4/2007 | Robertson et al. |
| 7,214,498 B2 * | 5/2007 | Nelson et al. ............... 435/7.23 |
| 7,368,527 B2 | 5/2008 | Rosen et al. |
| 7,402,403 B1 | 7/2008 | Robertson et al. |
| 2003/0092009 A1 | 5/2003 | Palm |
| 2006/0014138 A1 | 1/2006 | Chinnaiyan |

FOREIGN PATENT DOCUMENTS

| | | |
|---|---|---|
| EP | 1074617 A2 | 2/2001 |
| EP | 1270724 A2 | 1/2003 |
| WO | WO0218424 A3 | 3/2002 |
| WO | WO 03/010199 | 2/2003 |
| WO | WO 03/064593 | 8/2003 |

OTHER PUBLICATIONS

Hale et al., "Zinc α-2-Glycoprotein Is Expressed by Malignant Prostatic Epithelium and May Serve as a Potential Serum Marker for Prostate Cancer1" Clinical Cancer Research, Apr. 2001; 7(4): 846-53.
Zhong, et al. "Efficient Identification And User of Tumor-Associated Antibodies as Markers of Non-small Cell Lung Cancer" Chest 2004, vol. 125, pp. 105-106.
Hufton et al. "Serological antigen selection of phage displayed colorectal tumour cDNA libraries." Biochemical Society Transactions. vol. 26, p. S5, entire document (1998).
Miller et al. "Antibody microarray profiling of human prostate cancer sera: Antibody screening and identification of potential biomarkers." Proteomics. vol. 3, pp. 56-63, p. 58 (2003).
Eisen et al. "Cluster analysis and display of genome-wide expression patterns." Proceedings of the National Academy of Sciences USA. vol. 95, pp. 14863-14868 (1998).
Li et al. "Gene Assessment and Sample Classification for Gene Expression Data Using a Genetic Algorithm/k-nearest Neighbor Method." Combinatorial Chemistry & High Throughput Screening. vol. 4, pp. 727-739 (2001).
Golub et al. "Molecular Classification of Cancer: Class Discovery and Class Prediction by Gene Expression Monitoring." Science. vol. 286, pp. 531-537(1999).
Crescenzi and Giuliani. "The main biological determinants of tumor line taxonomy elucidated by a principal component analysis of microarray data." FEBS Letters. vol. 507, pp. 114-118 (2001).
Denis and Green. "A novel, mitogen-activated nuclear kinase is related to a Drosophila developmental regulator." Genes & Development. vol. 10, pp. 261-271 (1996).
Denis et al. "RING3 Kinase Transactivates Promoters of Cell Cycle Regulatory Genes through E2F." Cell Growth & Differentiation. vol. 11, pp. 471-424 (2000).
Kanno et al. "Selective Recognition of Acetylated Histones by Bromodomain Proteins Visualized in Living Cells." Molecular Cell. vol. 13, pp. 33-43 (2004).
Gingras et al. "Regulation of translation initiation by FRAP/mTOR." Genes & Development. vol. 15, pp. 807-826 (2001).
Morino et al. "Eukaryotic Translation Initiation Factor 4E (eIF4E) Binding Site and the Middle One-Third of eIF4GI Constitute the Core Domain for Cap-Dependent Translation, and the C-Terminal One-Third Functions as a Modulatory Region." Molecular and Cellular Biology. vol. 20, pp. 468-477 (2000).
Cromer et al. "Identification of genes associate with tumorigenesis and metastatic potential of hypopharyngeal cancer by microarray analysis." Oncogene. vol. 23, pp. 2484-2498 (2004).
Park et al. "Bmi-1 is required for maintenance of adult self-renewing haematopoietic stem cells." Nature. vol. 15, No. 423 (6937), pp. 302-305 (2003).
Brass et al. "Translation initiation factor eIF-4gamma is encoded by an amplified gene and induces an immune response in squamous cell lung carcinoma." Human Molecular Genetics. vol. 6, pp. 33-39 (1997).
Bauer et al. "Translation Initiation Factor eIF-4G Is Immunogenic, Overexposed, and Amplified in Patients with Squamous Cell Lung Carcinoma." Cancer. vol. 92, pp. 822-829 (2001).

(Continued)

*Primary Examiner*—Larry R. Helms
*Assistant Examiner*—Meera Natarajan
(74) *Attorney, Agent, or Firm*—Casimir Jones, S.C.

(57) ABSTRACT

The present invention relates to compositions and methods for cancer diagnosis, research and therapy, including but not limited to, cancer markers. In particular, the present invention relates to ubiquilin 1 markers for cancer.

4 Claims, 29 Drawing Sheets

OTHER PUBLICATIONS

Bauer, C. et al. "Overexpression of the Eukaryotic Translation Initiation Factor 4G (EIF4G-1) in Squamous Cell Lung Carcinoma." International Journal of Cancer. vol. 98, pp. 181-185 (2002).
Fukuchi-Shimogori et al. "Malignant Transformation by Overproduction of Translation Initiation Factor eIF4G." Cancer Research. vol. 57, pp. 5041-5044 (1997).
Mazumder et al. "Regulated Release of L13a from the 60S Ribosomal Subunit as A Mechanism of Transcript-Specific Translational Control." Cell. vol. 115, pp. 187-198 (2003).
Miura et al. "Laser Capture Microdissection and Microarray Expression Analysis of Lung Adenocarcinoma Reveals Tobacco Smoking- and Prognosis-related Molecular Profiles." Cancer Research. vol. 62, pp. 3244-3250 (2002).
Racz et al. "Expression Analysis of Genes at 3q26-q27 Involved in Frequent Amplification in Squamous Cell Lung Carcinoma." European Journal of Cancer. vol. 35, pp. 641-646 (1999).
Molofsky et al. "Bmi-1 dependence distinguishes neural stem cell self-renewal from progenitor proliferation." Nature. vol. 425, pp. 962-967 (2003).
Singh and Figg. "Upregulation of the Androgen Receptor During Prostate Cancer Progression." Cancer Biology and Therapy. vol. 3 pp. 284-285 (2004).
Taplin et al. "Androgen Receptor: A Key Molecule in the Progression of Prostate Cancer to Hormone Independence." Journal of Cellular Biochemistry. vol. 91, pp. 483-490 (2004).
Liao and Witte. "Autoimmune anti-androgen-receptor antibodies in human serum." Proceedings of the National Academy of Sciences USA. vol. 82, pp. 8345-8348 (1985).
Latulippe et al. "Comprehensive Gene Expression Analysis of Prostate Cancer Reveals Distinct Transcriptional Programs Associated with Metastatic Disease." Cancer Research. vol. 62, pp. 4499-4506 (2002).
Luo et al. "Gene Expression Analysis of Prostate Cancers." Molecular Carcinogenesis. vol. 33, pp. 25-35 (2002).
Luo et al. "Human Prostate Cancer and Benign Prostatic Hyperplasia: Molecular Dissection by Gene Expression Profiling." Cancer Research. vol. 61, pp. 4683-4688 (2001).
Singh et al. "Gene expression correlates of clinical prostate cancer behavior." Cancer Cell. vol. 1, pp. 203-209 (2002).
Welsh et al. "Analysis of Gene Expression Indentifies Candidate Markers and Pharmacological Targets in Prostate Cancer." Cancer Research. vol. 61, pp. 5974-5978 (2001).
Bolstad et al. "A comparison of normalization methods for high density oligonucleotide array data based on variance and bias." Bioinformatics. vol. 19, pp. 185-193 (2003).
Bo et al. "New Feature subset selection procedures for classification of expression profiles." Genome Biology. vol. 3, No. 4, research0017.1-0017.11 (2002).
Rhodes et al. "Large-scale meta-analysis of cancer microarray data identifies common transcriptional profiles of neoplastic transformation and progression." Proceedings of the National Academy of Sciences USA. vol. 101, No. 25, pp. 9309-9314 (2004).
Rhodes et al. "ONCOMINE: A Cancer Microarray Database and Integrated Data-Mining Platform." Neoplasia. vol. 6, No. 1, pp. 1-6 (2004).
Wang et al. "Autoantibody Signatures in Prostate Cancer." New England Journal of Medicine. 353, No. 12, pp. 1224-1235 (2005).
Radmacher et al. "A Paradigm for Class Prediction Using Gene Expression Profiles." Journal of Computational Biology. vol. 9, No. 3, pp. 505-511 (2002).
Tukey et al. "Tightening the Clinical Trial." Controlled Clinical Trials. vol. 14, No. 4, pp. 266-285 (1993).
Kleijnen et al. "The hPLIC Proteins May Provide a Link between the Ubiquitination Machinery and the Proteasome." Molecular Cell. vol. 6. No. 2, pp. 409-419 (2000).
Mah et al. "Identification of Ubiquilin, a Novel Presenilin Interactor That Increases Presenilin Protein Accumulation." Journal of Cell Biology. vol. 151, No. 4, pp. 847-862 (2000).
Hiltunen et al. "Ubiquilin 1 Modulates Amyloid Precursor Protein Trafficking and Aβ Secretion." Journal of Biological Chemistry. vol. 281, No. 43, pp. 32240-32253 (2006).
Thomas et al. "Interaction between Presenilin 1 and Ubiquilin 1 as Detected by Fluorescence Lifetime Imaging Microscopy and a High-throughput Fluorescent Plate Reader." Journal of Biological Chemistry. vol. 281, No. 36, pp. 26400-26407 (2006).
Slifer et al. "The Ubiquilin 1 Gene and Alzheimer's Disease." New England Journal of Medicine. vol. 352, No. 26, pp. 2752-2753 (2005).
Garber et al. "Diversity of gene expression in adenocarcinoma of the lung." Proceedings of the National Academy of Sciences USA. vol. 98, No. 24, pp. 13784-13789 (2001).
Chen et al. "Protein profiles associated with survival in lung adenocarcinoma." Proceedings of the National Academy of Sciences USA. vol. 100, No. 23, pp. 13537-13542 (2003).
Zhong et al. "Antibodies to HSP70 and HSP90 in serum in non-small cell lung cancer patients." Cancer Detection and Prevention. vol. 27, No. 4, pp. 285-290 (2003).
Zhong et al. "Identification of circulating antibodies to tumor-associated proteins for combined use as markers of non-small cell lung cancer." Proteomics. vol. 4, No. 4, pp. 1216-1225 (2004).
Koziol et al. "Recursive Partitioning as an Approach to Selection of Immune Markers for Tumor Diagnosis." Clinical Cancer Research. vol. 9, No. 14, pp. 5120-5126 (2003).
Rossi et al. "Review: The role of the ubiquitination-proteasome pathway in breast cancer: Use of mouse models for analyzing ubiquitination processes." Breast Cancer Research. vol. 5, No. 1, pp. 16-22 (2003).
Huebener et al. "AACR Special Conference in cancer research: ubiquitination in normal and cancer cells." Expert Opin. Biol. Ther. vol. 3, No. 1, pp. 187-192 (2003).
Abe et al., "Plasma Levels of Heat Shock Protein 70 inPatients with Prostate Cancer: A Potential Biomarker for Prostate Cancer" Clin Prostate Cancer, Jun. 2004; 3(1): 49-53.
Brass et al., Blood, "Role of Amplified Genes in the Production of Autoantibodies" vol. 93(7) (Apr. 1), 1999:2158-2166.
European Supplemental Search Report; EP Patent Application No. 05785426.7; Applicant: Regents of the University of Michigan; Dated: Mar. 30, 2009 (5 pgs.).
Somers, Veerle A., et al.; "A Panel of Candidate Tumor Antigens in Colorectal Cancer Revealed by the Serological Selection of a Phage Displayed cDNA Expression Library"; The Journal of Immunology, Sep. 1, 2002; vol. 169 p. 2772-2780; Baltimore, MD.
Sioud, M., et al.; "Profiling the immune responses in patient sera with peptide and cDNA display libraries (Review)"; International Journal of Molecular Medicine, Jan. 1, 2000; vol. 2, No. 6 p. 123-128; Spandidos, Athens, GR.
Beghetto, Elisa, et al.; "Identification of a human immunodominant B-cell epitope within the GRA1 antigen of Toxoplasma gondii by phage display of cDNA libraries"; International Journal of Parasitology, Dec. 1, 2001; vol. 31, No. 14 p. 1659-1668; Pergamon Press, GB.
Hansen, Mona H., et al.; "Antigen-Specific IgG Antibodies in State IV Long-Time Survival Breast Cancer Patients"; Molecular Medicine, Blackwell Science, Jan. 1, 2001; vol. 7, No. 4 p. 230-239; Cambridge, MA.
Sioud, Mouldy, et al.; "Profiling the immune response in patients with breast cancer by phage-displayed cDNA libraries"; European Journal of Immunology, Mar. 1, 2001; Wiley-V C H Verlag GMBH & Co.; vol. 31, No. 3 p. 716-725; KGAA, DE.
Minenkova, Olga, et al.; "Identification of Tumor-Associated Antigens by Screening Phage-Displayed Human cDNA Libraries With Sera From Tumor Patients"; Publication of the International Union Against Cancer; 106, p. 534-544 (2003); 2003 Wiley-Liss, Inc.
Chen, Guoan, et al.; "Autoantibody Profiles Reveal Ubiquilin 1 as a Humoral Immune Response Target in Lung Adenocarcinoma"; Research Article, Cancer Res. 2007; 67: (7). Apr. 1, 2007; p. 3461-3467; www.aacrjournals.org.
Erkanli, Al, et al.; "Application of Bayesian Modeling of Autologous Antibody Responses against Ovarian Tumor-Associates Antigens to Cancer Detection"; Research Article, Cancer Res 2006; 66: (3). Feb. 1, 2006; p. 1792-1798; www.aacrjournals.org.
Mintz, Paul J., et al.; "Fingerprinting the Circulating Repertoire of Antibodies from Cancer Patients"; Research Article, Published online Dec. 23, 2002; doi:10.1038/nbt 774; www.nature.com/naturebiotechnology; Jan. 2003 vol. 21 p. 57-63.

Vaarala, Markku H., et al.; "Several Genes Encoding Ribosomal Proteins are Over-Expressed in Prostate-Cancer Cell Lines: Confirmation of L7a and L37 Over-Expression in Prostate-Cancer Tissue Samples"; Publication of the International Union Against Cancer; 78, p. 27-32 (1998); 1998 Wiley-Liss, Inc.

Gure, Ali O., et al.; "Human Lung Cancer Antigens Recognized by Autologous Antibodies: Definition of a Novel cDNA Derived from the Tumor Suppressor Gene Locus on Chromosome 3p21.3"; Ludwig Institute for Cancer Research; Cancer Research 58, p. 1034-1041; Mar. 1, 1998.

Elek, Jacki, et al.; "Microarray-Based Expression Profiling in Prostate Tumors"; Center for Molecular Biology and Biotechnology and Department of Biology, Boca Raton, FL; invivo 14: p. 173-182 2000.

Tureci, Ozlem; "Serological Analysis of Human Tumor Antigens: Molecular Definition and Implications"; Molecular Medicine Today, Aug. 1997 p. 342-349; Elsevier Science Ltd.

Walker, Michael G., et al.; Prediction of Gene Function by Genome-Scale Expression Analysis: Prostate Cancer-Associated Genes; Genome Res. 1997 9: p. 1198-1203; Access the most recent version at doi: 10.1101/gr.9.12.1198; 1999 Cold Spring Harbor Laboratory Press ISSN1054-9803/99.

Mudenda, B., et al.; "The Relationship Between Serum p53 Autoantibodies and Characteristics of Human Breast Cancer"; Br. J. Cancer (1994) 69, p. 1115-1119; MacMillan Press Ltd., 1994.

Stockert, Elisabeth, et al.; "A Survey of the Humoral Immune Response of Cancer Patients to a Panel of Human Tumor Antigens"; J. Ep. Med. The Rockefeller University Press; 0022-1007/98/04/1349/06; vol. 187, No. 8 Apr. 20, 1998 p. 1349-1354; http://www.jem.org.

Old, Lloyd J., et al.; "New Paths in Human Cancer Serology"; Ludwig Institute for Cancer Research; J. Exp. Med. The Rockefeller University Press 0022-1007/98/04/1163/05; vol. 187, No. 8, Apr. 20, 1998 p. 1163-1167; http://www.jem.org.

Kuriyama, M., et al.; "Multipile Marker Evaluation in Human Prostate Cancer With the Use of Tissue-Specific Antigens"; JNCI, vol. 68, No. 1 Jan. 1982 p. 99-105.

Mercer, Donald W.; "Use of Multiple Markers to Enhance Clinical Utility" Immunodiagnosis of Cancer, Immunology Series, 53, pp. 39-54, 1990.

* cited by examiner

Figure 4

| Characteristic | Value |
|---|---|
| Mean age (yr) ± SEM * | 59.508 ± 1.05 |
| Mean gland weight (g) ± SEM # | 57.717 ± 8.78 |
| Mean gland size (cm) ± SEM ! | 1.416 ± 0.096 |
| PSA @ | |
| Mean (ng/ml) ± SEM | 8.276 ± 1.073 |
| 0-2.5 ng/ml (%) | 8.5 |
| 2.6 –10 ng/ml (%) | 69.5 |
| 4- 10 ng/ml (%) | 57.6 |
| > 10 ng/ml (%) | 22 |
| Biochemical Recurrence (%) | 13.6 |
| Gleason grade • | |
| =< 6 (%) | 36.2 |
| >=7 (%) | 63.8 |
| Primary tumor identification † | |
| T2a (%) | 23.7 |
| T2b (%) | 64.4 |
| T3a (%) | 3.4 |
| T3b (%) | 6.8 |
| T4 (%) | 1.7 |
| Ethnicity ‡ | |
| White (Not Hispanic origin) (%) | 83 |
| Hispanic (%) | 1.9 |
| Black (Not Hispanic origin) (%) | 3.8 |
| Unknown (%) | 11.3 |

\* Data were available for 59 patients.
Data were available for 59 patients.
! Data were available for 58 patients.
@ Data were available for 59 patients.
• Data were available for 58 patients.
† Data were available for 59 patients.
‡ Data were available for 53 patients.

Figure 5

| Characteristic | Value |
| --- | --- |
| Mean age (yr) ± SEM [#] | 59.72 ± 1.06 |
| Mean gland weight (g) ± SEM [#] | 57.750 ± 2.49 |
| Mean gland size (cm) ± SEM [!] | 1.628 ± 0.145 |
| PSA [#] | |
| Mean (ng/ml) ± SEM | 7.633 ± 1.053 |
| 0-2.5 ng/ml (%) | 24.6 |
| 2.6 – 10 ng/ml (%) | 62.5 |
| 4- 10 ng/ml (%) | 43.8 |
| > 10 ng/ml (%) | 23 |
| Biochemical Recurrence (%) | 35.4 |
| Gleason grade [#] | |
| =< 6 (%) | 52.1 |
| >=7 (%) | 47.9 |
| Primary tumor identification [#] | |
| T2a (%) | 22.9 |
| T2b (%) | 58.3 |
| T3a (%) | 8.3 |
| T3b (%) | 10.4 |
| Ethnicity [#] | |
| White (Not Hispanic origin) (%) | 80.9 |
| Hispanic (%) | 2.1 |
| Black (Not Hispanic origin) (%) | 2.1 |
| Unknown (%) | 14.9 |

[#] Data were available for 62 patients.
[!] Data were available for 61 patients.

Figure 6

| Sample Number | Age | RRP | Gleason | Disease Stage at Disease | PSA (ng/ml) | Current Bone Disease | Current Soft Tissue Disease | Hormone Treatment | Chemotherapy |
|---|---|---|---|---|---|---|---|---|---|
| P1 | 58 | Y | 5+4=9 | T3b | 4 | N | N | Y | N |
| P2 | 76 | N | N/A | Metastatic | 85 | Y | Y | Y | N |
| P3 | 76 | Y | N/A | T2 | 16 | Y | Y | Y | N |
| P4 | 68 | N | 3+4=7 | T1a | 15 | N | N | N | N |
| P5 | 69 | N | 4+3=7 | T2c | 239 | Y | N | Y | Y |
| P6 | 76 | N | 4+4=8 | T2 | 6 | Y | N | Y | Y |
| P7 | 44 | N | 5+4=9 | Metastatic | 674 | Y | Y | Y | N |
| P8 | 72 | N | 1+2=3 | Metastatic | 7 | Y | Y | Y | Y |
| P9 | 72 | N | 4+4=8 | Metastatic | 412 | Y | N | Y | Y |
| P10 | 45 | N | 4+3=7 | Metastatic | 0.1 | Y | N | Y | Y |
| P11 | 52 | N | 4+3=7 | Metastatic | 183 | Y | N | Y | Y |

Figure 7

| Number of features | Prediction Accuracy (%) | Error |
|---|---|---|
| 10 | 93 | 9/129 |
| 20 | 93 | 9/129 |
| 21 | 93 | 9/129 |
| 22 | 93 | 9/129 |
| 23 | 91 | 12/129 |
| 24 | 90 | 13/129 |
| 25 | 90 | 13/129 |
| 26 | 91 | 12/129 |
| 30 | 91 | 12/129 |
| 50 | 88 | 15/129 |
| 100 | 86 | 18/129 |

Figure 8

| Sample Name | Call | Confidence | Pathology | Error |
|---|---|---|---|---|
| TrainSet_175 | Normal | 0.828 | Normal | |
| TrainSet_116 | Normal | 0.827 | Normal | |
| TrainSet_178 | Normal | 0.769 | Normal | |
| TrainSet_168 | Normal | 0.768 | Normal | |
| TrainSet_111 | Normal | 0.726 | Normal | |
| TrainSet_182 | Normal | 0.695 | Normal | |
| TrainSet_190 | Normal | 0.684 | Normal | |
| TrainSet_187 | Normal | 0.678 | Normal | |
| TrainSet_115 | Normal | 0.648 | Normal | |
| TrainSet_208 | Normal | 0.645 | Normal | |
| TrainSet_219 | Normal | 0.638 | Normal | |
| TrainSet_114 | Normal | 0.606 | Normal | |
| TrainSet_203 | Normal | 0.598 | Normal | |
| TrainSet_179 | Normal | 0.581 | Normal | |
| TrainSet_189 | Normal | 0.562 | Normal | |
| TrainSet_117 | Normal | 0.558 | Normal | |
| TrainSet_184 | Normal | 0.538 | Normal | |
| TrainSet_214 | Normal | 0.527 | Normal | |
| TrainSet_164 | Normal | 0.527 | Normal | |
| TrainSet_174 | Normal | 0.507 | Normal | |
| TrainSet_108 | Normal | 0.487 | Normal | |
| TrainSet_109 | Normal | 0.463 | Normal | |
| TrainSet_112 | Normal | 0.453 | Normal | |
| TrainSet_113 | Normal | 0.439 | Normal | |
| TrainSet_107 | Normal | 0.437 | Normal | |
| TrainSet_166 | Normal | 0.433 | Normal | |
| TrainSet_198 | Normal | 0.430 | Cancer | * |
| TrainSet_167 | Normal | 0.410 | Normal | |
| TrainSet_207 | Normal | 0.403 | Normal | |
| TrainSet_165 | Normal | 0.394 | Normal | |
| TrainSet_181 | Normal | 0.370 | Normal | |
| TrainSet_103 | Normal | 0.367 | Normal | |
| TrainSet_170 | Normal | 0.358 | Normal | |
| TrainSet_225 | Normal | 0.355 | Normal | |
| TrainSet_169 | Normal | 0.354 | Normal | |
| TrainSet_105 | Normal | 0.345 | Normal | |
| TrainSet_102 | Normal | 0.331 | Normal | |
| TrainSet_135 | Cancer | 0.329 | Cancer | |
| TrainSet_157 | Normal | 0.326 | Cancer | * |
| TrainSet_177 | Normal | 0.324 | Normal | |
| TrainSet_173 | Normal | 0.323 | Normal | |
| TrainSet_212 | Cancer | 0.236 | Normal | * |
| TrainSet_136 | Cancer | 0.233 | Cancer | |
| TrainSet_217 | Normal | 0.233 | Normal | |
| TrainSet_221 | Normal | 0.231 | Normal | |
| TrainSet_110 | Cancer | 0.227 | Normal | * |

Figure 8 continued

| | | | |
|---|---|---|---|
| TrainSet_106 | Cancer | 0.226 | Cancer |
| TrainSet_210 | Normal | 0.226 | Normal |
| TrainSet_101 | Normal | 0.222 | Normal |
| TrainSet_229 | Normal | 0.216 | Normal |
| TrainSet_133 | Cancer | 0.211 | Cancer |
| TrainSet_143 | Cancer | 0.202 | Cancer |
| TrainSet_171 | Normal | 0.197 | Normal |
| TrainSet_140 | Cancer | 0.195 | Cancer |
| TrainSet_159 | Cancer | 0.193 | Cancer |
| TrainSet_162 | Cancer | 0.191 | Cancer |
| TrainSet_131 | Cancer | 0.180 | Cancer |
| TrainSet_196 | Cancer | 0.176 | Cancer |
| TrainSet_156 | Cancer | 0.176 | Cancer |
| TrainSet_160 | Cancer | 0.168 | Cancer |
| TrainSet_222 | Normal | 0.166 | Normal |
| TrainSet_193 | Cancer | 0.165 | Cancer |
| TrainSet_161 | Cancer | 0.163 | Cancer |
| TrainSet_122 | Cancer | 0.156 | Cancer |
| TrainSet_130 | Cancer | 0.153 | Cancer |
| TrainSet_213 | Normal | 0.151 | Normal |
| TrainSet_119 | Cancer | 0.148 | Cancer |
| TrainSet_146 | Cancer | 0.146 | Cancer |
| TrainSet_163 | Cancer | 0.146 | Cancer |
| TrainSet_185 | Normal | 0.142 | Normal |
| TrainSet_183 | Normal | 0.140 | Normal |
| TrainSet_211 | Normal | 0.138 | Normal |
| TrainSet_180 | Normal | 0.136 | Normal |
| TrainSet_191 | Cancer | 0.132 | Cancer |
| TrainSet_188 | Normal | 0.130 | Normal |
| TrainSet_199 | Cancer | 0.121 | Cancer |
| TrainSet_125 | Cancer | 0.116 | Cancer |
| TrainSet_150 | Cancer | 0.109 | Cancer |
| TrainSet_223 | Cancer | 0.108 | Cancer |
| TrainSet_144 | Cancer | 0.105 | Cancer |
| TrainSet_201 | Normal | 0.102 | Normal |
| TrainSet_176 | Normal | 0.097 | Normal |
| TrainSet_202 | Normal | 0.097 | Normal |
| TrainSet_128 | Cancer | 0.093 | Cancer |
| TrainSet_141 | Cancer | 0.089 | Cancer |
| TrainSet_194 | Cancer | 0.088 | Cancer |
| TrainSet_209 | Normal | 0.087 | Normal |
| TrainSet_124 | Cancer | 0.085 | Cancer |
| TrainSet_126 | Cancer | 0.075 | Cancer |
| TrainSet_172 | Normal | 0.075 | Normal |
| TrainSet_151 | Cancer | 0.074 | Cancer |
| TrainSet_227 | Normal | 0.074 | Normal |
| TrainSet_186 | Normal | 0.069 | Normal |
| TrainSet_137 | Cancer | 0.069 | Cancer |
| TrainSet_138 | Cancer | 0.069 | Cancer |
| TrainSet_120 | Cancer | 0.067 | Cancer |
| TrainSet_129 | Cancer | 0.066 | Cancer |
| TrainSet_200 | Cancer | 0.063 | Cancer |
| TrainSet_226 | Normal | 0.058 | Normal |
| TrainSet_104 | Cancer | 0.056 | Cancer |
| TrainSet_206 | Cancer | 0.056 | Normal |
| TrainSet_152 | Cancer | 0.052 | Cancer |

Figure 8 continued

| | | | | |
|---|---|---|---|---|
| TrainSet_195 | Cancer | 0.050 | Cancer | |
| TrainSet_228 | Normal | 0.045 | Normal | |
| TrainSet_192 | Cancer | 0.042 | Cancer | |
| TrainSet_149 | Cancer | 0.041 | Cancer | |
| TrainSet_142 | Cancer | 0.040 | Cancer | |
| TrainSet_204 | Normal | 0.038 | Normal | |
| TrainSet_145 | Cancer | 0.033 | Cancer | |
| TrainSet_158 | Cancer | 0.027 | Cancer | |
| TrainSet_197 | Cancer | 0.024 | Cancer | |
| TrainSet_123 | Cancer | 0.024 | Cancer | |
| TrainSet_153 | Normal | 0.021 | Cancer | * |
| TrainSet_121 | Cancer | 0.019 | Cancer | |
| TrainSet_155 | Cancer | 0.018 | Cancer | |
| TrainSet_205 | Cancer | 0.016 | Normal | * |
| TrainSet_218 | Normal | 0.016 | Normal | |
| TrainSer_216 | Normal | 0.016 | Normal | |
| TrainSet_148 | Cancer | 0.013 | Cancer | |
| TrainSet_134 | Normal | 0.010 | Cancer | * |
| TrainSet_220 | Normal | 0.007 | Normal | |
| TrainSet_118 | Cancer | 0.003 | Cancer | |
| TrainSet_224 | Cancer | 0.002 | Normal | * |
| TrainSet_132 | Cancer | 0.001 | Cancer | |
| TrainSet_127 | Cancer | 0.000 | Cancer | |
| TrainSet_139 | Normal | 0.000 | Cancer | * |
| TrainSet_147 | Normal | 0.000 | Cancer | * |
| TrainSet_154 | Cancer | 0.000 | Cancer | |
| TrainSet_215 | Normal | 0.000 | Normal | |

\# Armstrong, S. A., Staunton, J. E., Silverman, L. B., Pieters, R., den Boer, M. L., Minden, M. D., Sallan, S. E., Lander, E. S., Golub, T. R. and Korsmeyer, S. J., MLL translocations specify a distinct gene expression profile that distinguishes a unique leukemia. Nat Genet 2002. 30: 41-47.

Figure 9

| Sample Name | Call | Confidence | Pathology | Error |
|---|---|---|---|---|
| TestSet_101 | Normal | 0.147 | Normal | |
| TestSet_102 | Normal | 0.239 | Normal | |
| TestSet_103 | Normal | 0.270 | Normal | |
| TestSet_104 | Cancer | 0.317 | Normal | * |
| TestSet_105 | Normal | 0.386 | Normal | |
| TestSet_106 | Cancer | 0.460 | Normal | * |
| TestSet_107 | Normal | 0.471 | Normal | |
| TestSet_108 | Normal | 0.570 | Normal | |
| TestSet_109 | Normal | 0.577 | Normal | |
| TestSet_110 | Normal | 0.583 | Normal | |
| TestSet_111 | Normal | 0.601 | Normal | |
| TestSet_112 | Normal | 0.635 | Normal | |
| TestSet_113 | Normal | 0.660 | Normal | |
| TestSet_114 | Normal | 0.711 | Normal | |
| TestSet_115 | Normal | 0.748 | Normal | |
| TestSet_116 | Normal | 0.002 | Cancer | * |
| TestSet_117 | Cancer | 0.002 | Cancer | |
| TestSet_118 | Normal | 0.012 | Cancer | * |
| TestSet_119 | Cancer | 0.047 | Cancer | |
| TestSet_120 | Cancer | 0.072 | Cancer | |
| TestSet_121 | Cancer | 0.084 | Cancer | |
| TestSet_122 | Cancer | 0.137 | Cancer | |
| TestSet_123 | Cancer | 0.186 | Cancer | |
| TestSet_124 | Normal | 0.226 | Cancer | * |
| TestSet_125 | Normal | 0.256 | Cancer | * |
| TestSet_126 | Cancer | 0.263 | Cancer | |
| TestSet_127 | Normal | 0.279 | Cancer | * |
| TestSet_128 | Cancer | 0.297 | Cancer | |
| TestSet_129 | Normal | 0.343 | Cancer | * |
| TestSet_130 | Normal | 0.351 | Cancer | * |
| TestSet_131 | Cancer | 0.382 | Cancer | |
| TestSet_132 | Normal | 0.386 | Cancer | * |
| TestSet_133 | Cancer | 0.396 | Cancer | |
| TestSet_134 | Cancer | 0.474 | Cancer | |
| TestSet_135 | Cancer | 0.504 | Cancer | |
| TestSet_136 | Cancer | 0.506 | Cancer | |
| TestSet_137 | Cancer | 0.543 | Cancer | |
| TestSet_138 | Cancer | 0.604 | Cancer | |

Figure 9 continued

| | | | | |
|---|---|---|---|---|
| TestSet_139 | Cancer | 0.610 | Cancer | |
| TestSet_140 | Cancer | 0.631 | Cancer | |
| TestSet_141 | Normal | 0.657 | Cancer | * |
| TestSet_142 | Cancer | 0.676 | Cancer | |
| TestSet_143 | Cancer | 0.700 | Cancer | |
| TestSet_144 | Cancer | 0.704 | Cancer | |
| TestSet_145 | Cancer | 0.708 | Cancer | |
| TestSet_146 | Cancer | 0.733 | Cancer | |
| TestSet_147 | Cancer | 0.761 | Cancer | |
| TestSet_148 | Cancer | 0.825 | Cancer | |
| TestSet_149 | Cancer | 0.836 | Cancer | |
| TestSet_150 | Cancer | 0.857 | Cancer | |
| TestSet_151 | Cancer | 0.872 | Cancer | |
| TestSet_152 | Cancer | 0.907 | Cancer | |
| TestSet_153 | Normal | 0.917 | Cancer | * |
| TestSet_154 | Cancer | 0.921 | Cancer | |
| TestSet_155 | Cancer | 0.930 | Cancer | |
| TestSet_156 | Cancer | 0.963 | Cancer | |
| TestSet_157 | Cancer | 0.984 | Cancer | |
| TestSet_158 | Cancer | 0.988 | Cancer | |
| TestSet_159 | Cancer | 1.000 | Cancer | |
| TestSet_160 | Cancer | 1.000 | Cancer | |
| TestSet_161 | Cancer | 1.000 | Cancer | |
| TestSet_162 | Cancer | 1.000 | Cancer | |
| TestSet_163 | Cancer | 1.000 | Cancer | |

* Golub, T.R. et al. Molecular classification of cancer: class discovery and class prediction by gene expression monitoring. *Science* 286, 531-537 (1999).

Figure 10

| Sample Name | Call | Confidence | Pathology | Error |
|---|---|---|---|---|
| Sample_1 | Cancer | 1.000 | Cancer | |
| Sample_2 | Cancer | 1.000 | Cancer | |
| Sample_3 | Cancer | 1.000 | Cancer | |
| Sample_4 | Cancer | 0.996 | Cancer | |
| Sample_5 | Cancer | 0.970 | Cancer | |
| Sample_6 | Cancer | 0.966 | Cancer | |
| Sample_7 | Cancer | 0.820 | Cancer | |
| Sample_8 | Normal | 0.615 | Cancer | * |
| Sample_9 | Cancer | 0.578 | Cancer | |
| Sample_10 | Cancer | 0.495 | Cancer | |
| Sample_11 | Cancer | 0.477 | Cancer | |
| Sample_12 | Normal | 0.319 | Cancer | * |
| Sample_13 | Normal | 0.314 | Cancer | * |
| Sample_14 | Cancer | 0.133 | Cancer | |
| Sample_15 | Normal | 0.065 | Cancer | * |

Figure 11

| Protein Symbol | Protein Sequence |
|---|---|
| RPL13A | RCEGINISGNFYRNKLKYLAFLRKRMNTNPSRGPYHFRAPSRIFWRTVRGMLPHKTKRGQAALDRLKVFDGIPPPYDKKKADGGSCCPQGRASEAYKKVCLSGAPGSRGWLEVPGSDSHPGGEEEACGRTRVTS |
| RPL22 | SSITVTSEVPFSKRYLKYLTKKYLKKNNLRDWLRVVANSKESYELRYFQINQDEEEEESLRPHSSN |
| Hypothetical Protein XP_373908 | PASASILAGVPMYRNEFTAWYRRMSVVYGIGTWSVLGSLLYYSRTMAKSSVDQKDGSASEVPSELSERPSLRPHSSN |
| EIF4G1 | QTKEERISQXEIMSGARTASTPTPPQTGGGLEPQANGETPQVAVIVRPDDRSQGAIIADRPGLPGPEHSPSESQPSSPSPTPSPSPVLEPGSEPNLAVLSIPGDTMTTIQMSVEEACGRTRVTS |
| BRD2 | SSESRPMSYDEKRQLSLDINKLPGEKLGRVVHIIQAREPSLRDSNPEEIEIDFETLKPSTLRELERYVLSCLRKKPRKPYSTYEMRFISWF |

Figure 12

| Lab # | Mimotope Candidate | E value | Sequence Alignment(Query, epitope sequence; Sbjct, protein hit) | Protein Sequence |
|---|---|---|---|---|
| Epitope 1 | unnamed protein product | 1.00E-18 | Query: ILYPETLLKLLI SLRRFWAEMNRPSRYT INSSENRDNLTSS<br>ILYP. LLKLLI LR P K NRDSRY INSS N.DN.TSS<br>Sbjct: ILYDQALLKLLI SLRSPCTKTNKPSRYR INSEANKDNTSS | ILYPETLLKLLISLRRFWAEM<br>MEFSRYTIMSSENRDNLTSS<br>FPN |
| Epitope 2 | hypothetical protein XP_373740 | 5.00E-05 | Query: MVPRMRRTSRASIHHIKP<br>MVP M R+S+ SIHHIKP<br>Sbjct: MVPCMHRSSQYSIHHIKP | REMVPRMRRTSRASIHHIKP<br>TE |
| 5'-UTR_BMI1 | Androgen Receptor * | 5.00E-04 | Query: CVGGRGGGGGGGGRGAGGGRGAGAGGGRPEA<br>G GG GGGGGGG G GGG G G GGG EA<br>Sbjct: GGGGGGGGGGGGGGGGGGGGGGGGGGG..EA | GVGGRGGGGGGGGRGAG<br>GGRGAGAGGGRPEAA |
| Epitope 3 | Serine/threonine-protein kinase DCAMKL1 | 0.78 | Query: IVKKQKSLCSGFKEHL...NEASIL<br>I+KK K C G KH+ N SIL<br>Sbjct: IIFKGK...CRG.KHDMIQHFVSIL | KAECFKNLIVKKQKSLCSGF<br>KEHLNEASILAQVSVSSSKR<br>WWKSWENLISSFMVWNPAH<br>LIISIPNLEKTSDLSMMSKLIF<br>LLGSRRFFRSSPRGIF |
| Epitope 4 | hypothetical protein MGC20470 | 1.8 | Query: PLKIPVA....TKNT...QASLGK..QK<br>PLKIP A TKNT A L K QK<br>Sbjct: PLKIPPARVTLTKNTTAGAAPLTKNIQK | RMPKEPLKIPVATSRTQASL<br>GKQKCRRRIMMSLRQRWQ<br>MGISWMGRLKPTQW |
| Epitope 5 | hypothetical protein DKFZp564I1171.1 | 2.6 | Query: CCEKGKFQ<br>CCEKGK+Q<br>Sbjct: CCEKGKRQ | EGSVYQCCEKGKKQVCSQ<br>R |
| Epitope 6 | hypothetical protein MGC13275 | 2.7 | Query: QSSVALTNPESYHILKPKLEAD<br>QSSVAL+ P S KP+L+ D<br>Sbjct: QSSVALSTPIS....KPQLDTE | QSSVALTNPESYHILKPKLE<br>ADLRWLKLRKRKQVSKLLVL<br>SCCLLKNLGFWKGRMGKTQ<br>QRYARLTLWRLWTLQVQPS<br>TLT |
| Epitope 7 | PTPL1-associated RhoGAP 1 | 3.4 | Query: QKLCQAKEKGM<br>+KLCQA G GM<br>Sbjct: EKLCQALGMGM | QKLCQAKEKGMCMKKLRML<br>WECQKLYSLGF |
| Epitope 8 | Unknown Protein | 3.6 | Query: PRTRTLRARRSPRNKI-AQK<br>P TRTLR RNK AQK<br>Sbjct: PTTRTLR....DKNKAPAQK | APRTRTLRARRSPRMFIAQK<br>WMMKTVKEEEWNVWMKC<br>PILKNSLPISKINFIKND |
| Epitope 9 | organic cation transporter | 3.8 | Query: PQWLLPQRGIRNT<br>P+WLL QK RIT<br>Sbjct: PRWLLSQK..RIT | PNTFSISSEGNSDVQTNFNK<br>RIKRFIWVHGPQWLLPQKG<br>ERNTRVDDF |
| Epitope 10 | BRF1 protein | 7.6 | Query: PRCLETDATQWP<br>PRCL A+QWP<br>Sbjct: PRCL.HAEQWP | PFCKFRILSPRCLSDATQWP<br>FKVLFKWDCSSNSFLGPN |
| Epitope 11 | MOV10-like 1 | 28 | Query: VSALLGWQK<br>V++LLGW.K<br>Sbjct: VTSLLGWRK | NNVSALLGWQK |
| Epitope 12 | hypothetical protein FLJ40243 | 28 | Query: PINFKI<br>PINFKI<br>Sbjct: PINFKI | QSQHGGPENFKI |

Figure 12 continued

| Epitope | | | Query/Sbjct | |
|---|---|---|---|---|
| Epitope 13 | zinc finger protein 292 | 38 | Query: LLTKTIY<br>LLTKT·Y<br>sbjct: LLTETVT | LVSILLTKTIY |
| Epitope 14 | HVEC cell-cell adhesion molecule | 51 | Query: FATFPT<br>FATFPT<br>sbjct: FATFPT | EFFATFPTPKQHGA |

* Besides androgen receptor, this sequence also matches the following proteins with significant E value: autoantigen P542, BAF250b subunit, Bm-1, CAPNS1 protein, FBRL_HUMAN, fibrillarin, FUSE binding protein 3, GAR1 protein, HMG-box transcription factor TCF-3, Homeobox protein SIX3, homeotic protein EVX2, keratin 1, MHC class II regulatory factor, RFX, RDC-1, SHOX2 protein, signal recognition particle 6S, SRP6S protein, SRY, SWI/SNF chromatin remodeling complex subunit OSA2.

Figure 23
Table 6

Sequence identity of twenty-two diagnosis related humoral immune response targets

| Clone ID | Translated peptide sequence | Size of cDNA inserts (bp) | size of translated peptides (aa) | BLASTp Protein ID (first hit) | BLASTp Protein name (first hit) | BLASTp Identities | BLASTp E value |
|---|---|---|---|---|---|---|---|
| 20B4 | AQSRSRSRRQSPWPP | 916 | 15 | XP_533642.1 | PREDICTED: similar to Splicing factor | 12/16 (75%) | 1.7 |
| 17_E12 | AVAQMRMRMKMRMRMGQ EGTQQEPQQQNILEDDTRDQGAHTGGPPGKPDADE | 482 | 52 | DAA03327.1 | TPA: HDC18596 | 12/16 (75%) | 3.00E-04 |
| 6G7 | EHIPAPASPRFSIQGS | 263 | 16 | XP_587375.1 | similar to Hypothetical | 12/16 (75%) | 8.0 |
| 14A12 | ENVSFKKTKMFFWHN | 342 | 15 | BAC44541 | ABC transporter ATP-binding protein | 9/12 (75%) | 22 |
| 5_E2 | GFIRSSSPFKLSLAYCHVKLA CLPFFHDCKFPEASPAMQNSE SIKPLSFINYPVFGMSL | 285 | 59 | EAL23842.1 | postmeiotic segregation increased 2-like 5 | 15/20 (75%) | 0.003 |
| 15_E12 | GHANVTRTNPAFVHKVTVTQ NGKWAL | 369 | 26 | AAS50427.1 | AAR062Cp | 10/13 (76%) | 3.9 |
| 10D10 | GNRDPVAC | 426 | 8 | DAA00681.1 | TPA: 52K | 7/8 (87%) | 275 |
| 22C1 | IISRRGTNTAPLTSSSATTR TPARLWCCRS | 502 | 30 | EAA75083.1 | hypothetical protein FG05539.1 | 11/16 (68%) | 2.4 |
| 15A12 | IQCVYKPNSHFV | 409 | 12 | AAP57258.1 | unknown protein | 9/11 (81%) | 15 |
| 23_E12 | LFYGGMGGWKNGSRASEAD | 244 | 19 | NP_734416.1 | NIb protein | 10/13 (76%) | 7.9 |
| 17H10 | NSFLEGEEQIL | 937 | 11 | YP_001895.1 | hypothetical protein LIC11950 | 8/8 (100%) | 11 |
| 16A4 | NSQWL | 738 | 5 | AAQ06500.1 | unknown | 5/5 (100%) | 2388 |
| 12G5 | PGLIPGFTPGLGALGSTGGSSG TNGSN ... EANLQALIATGGDINAAIERLLGSQPS | 388 | 112 | NP_038466.2 | ubiquilin 1 | 112/112 (100%) | 2.00E-94 |
| 16_E9 | PQCREKTKFN | 842 | 10 | NP_203128.1 | tripartite motif-containing 7 isoform 4 | 5/5 (100%) | 215 |
| 2D3 | PTLCVPESAPKCWQ | 322 | 14 | ZP_00692072.1 | conserved hypothetical protein | 8/9 (88%) | 18 |
| 17A5 | QAYVNV | 507 | 6 | ZP_00336338.1 | COG1538: Outer membrane protein | 6/6 (100%) | 725 |
| 3H7 | QHTNMAHVYICNKPACCAQVP | 547 | 21 | CAG11273.1 | unnamed protein product | 7/7 (100%) | 42 |
| 2F3 | QIIKLNKGVVINIIMEVRMAAR DGGLFSVI | 615 | 30 | BAD50647 | putative translation factor | 11/15 (73%) | 0.35 |
| 6F11 | RNPVSMKNAKKISWAWWHTS VVSSTQEVEAGELLEPGRRRLQ | 179 | 42 | P39192 | Alu subfamily SC sequence contamination warning entry | 30/41 (73%) | 3.00E-17 |
| 16_E8 | TMPKGNVKLGN | 295 | 11 | NP_002392.2 | mitogen-activated protein kinase kinase kinase 3 isoform 2 | 6/7 (85%) | 160 |
| 19D11 | TMTNQTNLKTNDNHTQH | 245 | 17 | CAD52700 | hypothetical protein | 10/11 (90%) | 3.8 |
| 1B2 | TVRVIMTCWLIVDIGLLIVSSVF | 137 | 23 | ZP_00381515 | hypothetical protein BlinB01000180 | 11/15 (73%) | 0.86 |

METHODS AND COMPOSITIONS FOR DIAGNOSING LUNG CANCER

This application is a continuation in part of application Ser. No. 11/145,861, filed Jun. 6, 2005, which claims priority to provisional application Ser. No. 60/578,406, filed Jun. 9, 2004, each of which is herein incorporated by reference in its entirety.

This invention was made with government support under CA111275, GM072007 and CA084896 awarded by the National Institutes of Health, and W81XWH-04-1-0886 awarded by the Army Medical Research and Material Command. The government has certain rights in the invention.

FIELD OF THE INVENTION

The present invention relates to compositions and methods for cancer diagnosis, research and therapy, including but not limited to, cancer markers. In particular, the present invention relates to ubiquilin 1 markers for lung cancer.

BACKGROUND OF THE INVENTION

Lung cancer remains the leading cause of cancer death in industrialized countries. About 75 percent of lung cancer cases are categorized as non-small cell lung cancer (e.g., adenocarcinomas), and the other 25 percent are small cell lung cancer. Lung cancers are characterized in to several stages, based on the spread of the disease. In stage I cancer, the tumor is only in the lung and surrounded by normal tissue. In stage II cancer, cancer has spread to nearby lymph nodes. In stage III, cancer has spread to the chest wall or diaphragm near the lung, or to the lymph nodes in the mediastinum (the area that separates the two lungs), or to the lymph nodes on the other side of the chest or in the neck. This stage is divided into IIIA, which can usually be operated on, and stage IIIB, which usually cannot withstand surgery. In stage IV, the cancer has spread to other parts of the body.

Most patients with non-small cell lung cancer (NSCLC) present with advanced stage disease, and despite recent advances in multi-modality therapy, the overall ten-year survival rate remains dismal at 8-10% (Fry et al., Cancer 86:1867 [1999]). However, a significant minority of patients, approximately 25-30%, with NSCLC have pathological stage I disease and are usually treated with surgery alone. While it is known that 35-50% of patients with stage I disease will relapse within five years (Williams et al., Thorac. Cardiovasc. Surg. 82:70 [1981]; Pairolero et al., Ann, Thorac. Surg. 38:331 [1984]), it is not currently possible to identify which specific patients are at high risk of relapse.

Adenocarcinoma is currently the predominant histologic subtype of NSCLC (Fry et al., supra; Kaisermann et al., Brazil Oncol. Rep. 8:189 [2001]; Roggli et al., Hum. Pathol. 16:569 [1985]). While histopathological assessment of primary lung carcinomas can roughly stratify patients, there is still an urgent need to identify those patients who are at high risk for recurrent or metastatic disease by other means. Previous studies have identified a number of preoperative variables that impact survival of patients with NSCLC (Gail et al., Cancer 54:1802 1984]; Takise et al., Cancer 61:2083 [1988]; Ichinose et al., J. Thorac. Cardiovasc. Surg. 106:90 [1993]; Harpole et al., Cancer Res. 55:1995]). Tumor size, vascular invasion, poor differentiation, high tumor proliferate index, and several genetic alterations, including K-ras (Rodenhuis et al., N. Engl. J. Med. 317:929 [1987]; Slebos et al., N. Engl. J. Med. 323:561 [1990]) and p53 (Harpole et al., supra; Horio et al., Cancer Res. 53:1 [1993]) mutation, have been reported as prognostic indicators.

Tumor stage is an important predictor of patient survival, however, much variability in outcome is not accounted for by stage alone, as is observed for stage I lung adenocarcinoma which has a 65-70% five-year survival (Williams et al., supra; Pairolero et al., supra). Current therapy for patients with stage I disease usually consists of surgical resection and no additional treatment (Williams et al., supra; Pairolero et al., supra). The identification of a high-risk group among patients with stage I disease would lead to consideration of additional therapeutic intervention for this group, as well as leading to improved survival of these patients.

SUMMARY OF THE INVENTION

The present invention relates to compositions and methods for cancer diagnosis, research and therapy, including but not limited to, cancer markers. In particular, the present invention relates to ubiquilin 1 markers for cancer.

For example, in some embodiments, the present invention provides a method for detecting cancer (e.g., lung cancer), comprising: providing a sample (e.g., blood or serum) from a subject suspected of having cancer (e.g., lung cancer); and detecting the presence or absence of autoantibodies to Ubiquilin 1 in the sample. In some embodiments, the presence of autoantibodies to Ubiquilin 1 in the sample is indicative of lung cancer in the subject. In some embodiments, detecting the presence of an autoantibody to the tumor antigen comprises detecting the binding of an antibody to said autoantibody. In some embodiments, the method further comprises the step of providing a prognosis to the subject.

In further embodiments, the present invention provides a method of screening compounds, comprising administering a test compound to a subject; and determining the presence or level of an autoantibody to Ubiquilin 1 in the presence of said test compound compared to the absence of the test compound. In some embodiments, detecting the presence of an autoantibody to Ubiquilin 1 comprises detecting the binding of an antibody to said autoantibody. In some embodiments, the subject has cancer (e.g., lung cancer).

BRIEF DESCRIPTION OF THE DRAWINGS

FIG. 2B shows immunoreactivity of three representative clones validated by ELISA. FIG. 2C shows titration curves of the humoral immune response to a representative phage-epitope clone (5'-UTR_BMI1).

FIG. 3 shows a gene expression meta-analysis of humoral immune response candidates.

FIG. 4 shows a Table of clinical and pathology information of prostate cancer patients used for biopanning and epitope profiling in the training cohort of sera.

FIG. 5 shows a Table of clinical and pathology information of prostate cancer patients used for epitope profiling in the validation cohort of sera.

FIG. 6 shows a Table of Clinical and pathology information of hormone-refractory prostate cancer patients.

FIG. 7 shows a Table of prediction accuracy of KNN models.

FIG. 8 shows a Table that summarizes class predictions for the training sample set.

FIG. 9 shows a Table of class predictions for the independent testing sample set.

FIG. 10 shows a Table of class predictions of prostate cancer sera in which PSA levels are less than 4 ng/ml.

FIG. 11 shows a Table of protein sequences of in-frame phage epitope clones.

FIG. 12 shows a Table of significant protein list for epitope protein sequence alignment.

FIG. 23 shows Table 6.

DEFINITIONS

Figure 1:
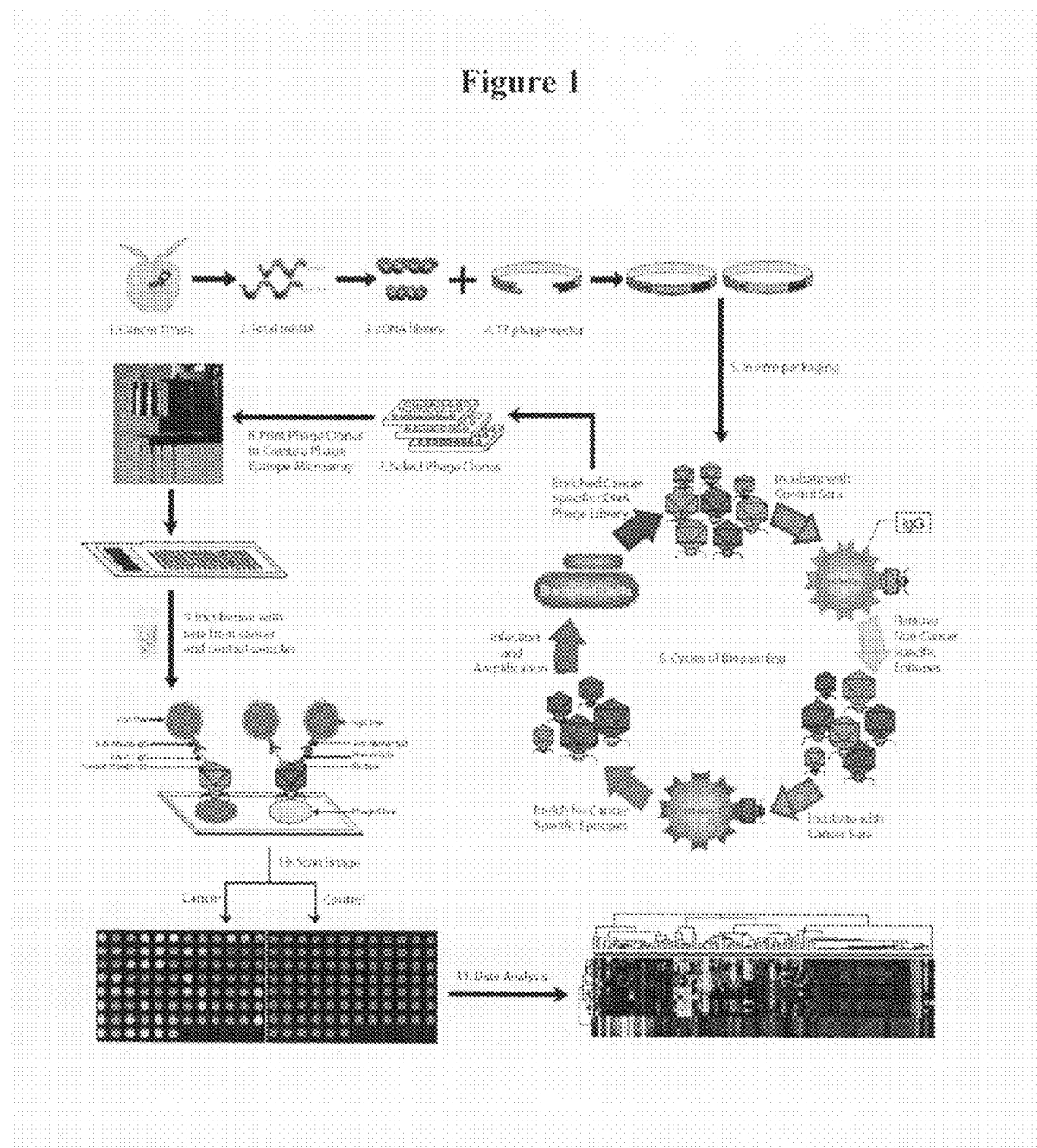
FIG. 1 provides a schematic overview of the phage-microarray profiling method of some embodiments of the present invention.

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received an initial diagnosis (e.g., a CT scan showing a mass or increased PSA level) but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental expose, previous incidents of cancer, preexisting non-cancer diseases, and lifestyle.

As used herein, the term "characterizing cancer in subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker or tumor antigen genes, including but not limited to, the cancer markers disclosed herein.

As used herein, the term "characterizing prostate tissue in a subject" refers to the identification of one or more properties of a tissue sample (e.g., including but not limited to, the presence of cancerous tissue, the presence of pre-cancerous tissue that is likely to become cancerous, and the presence of cancerous tissue that is likely to metastasize). In some embodiments, tissues are characterized by the identification of the expression of one or more cancer marker or tumor antigen genes, including but not limited to, the cancer markers disclosed herein.

As used herein, the term "cancer marker genes" refers to a gene whose expression level, alone or in combination with other genes, is correlated with cancer or prognosis of cancer. The correlation may relate to either an increased or decreased expression of the gene. For example, the expression of the gene may be indicative of cancer, or lack of expression of the gene may be correlated with poor prognosis in a cancer patient. Cancer marker expression may be characterized using any suitable method, including but not limited to, those described in illustrative Examples below.

As used herein, the term "a reagent that specifically detects expression levels" refers to reagents used to detect the expression of one or more genes (e.g., including but not limited to, the cancer markers of the present invention). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to non-cancerous control" refers to measuring the level of expression of a gene (e.g., the level of mRNA or protein) relative to the level in a non-cancerous prostate control sample. Gene expression can be measured using any suitable method, including but not limited to, those described herein.

As used herein, the term "detecting a change in gene expression in said cell sample in the presence of said test compound relative to the absence of said test compound" refers to measuring an altered level of expression (e.g., increased or decreased) in the presence of a test compound relative to the absence of the test compound. Gene expression can be measured using any suitable method, including but not limited to, those described herein.

As used herein, the term "tumor antigen" refers to an immunogenic epitope (e.g., protein) expressed by a tumor cell. The protein may be expressed by non tumor cells but be immunogenic only when expressed by a tumor cell. Alternatively, the protein may be expressed by tumor cells, but not normal cells. Exemplary tumor antigens include, but are not limited to, BRD2, eIF4G1, RPL22, RPL13A, HES1, and hypothetical protein XP_373908.

As used herein, the term "autoantibody" refers to an antibody produced by a host (with or without immunization) and directed to a host antigen (e.g., a tumor antigen).

As used herein, the term "cancer vaccine" refers to a composition (e.g., a tumor antigen and a cytokine) that elicits a tumor-specific immune response. The response is elicited from the subject's own immune system by administering the cancer vaccine composition at a site (e.g., a site distant from the tumor). In preferred embodiments, the immune response results in the eradication of tumor cells everywhere in the body (e.g., both primary and metastatic tumor cells).

As used herein, the term "instructions for using said kit for detecting cancer in said subject" includes instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. As used herein, the term "cancer expression profile map" refers to a presentation of expression levels of genes in a particular type of tissue (e.g., primary, metastatic, and pre-cancerous tissues). The map may be presented as a graphical representation (e.g., on paper or on a computer screen), a physical representation (e.g., a gel or array) or a digital representation stored in computer memory. Each map corresponds to a particular type of tissue (e.g., primary, metastatic, and pre-cancerous) and thus provides a template for comparison to a patient sample. In preferred embodiments, maps are generated from pooled samples comprising tissue samples from a plurality of patients with the same type of tissue.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "providing a prognosis" refers to providing information regarding the impact of the presence of cancer (e.g., as determined by the diagnostic methods of the present invention) on a subject's future health (e.g., expected morbidity or mortality, the likelihood of getting cancer, and the risk of metastasis).

As used herein, the term "prostate specific antigen failure" refers to the development of high prostate specific antigen levels in a patient following prostate cancer therapy (e.g., surgery). As used herein, the term "risk of developing prostate specific antigen failure" refers to a subject's relative risk (e.g., the percent chance or a relative score) of developing prostate specific antigen failure following prostate cancer therapy.

As used herein, the term "post surgical tumor tissue" refers to cancerous tissue (e.g., prostate tissue) that has been removed from a subject (e.g., during surgery).

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "initial diagnosis" refers to results of initial cancer diagnosis (e.g. the presence or absence of cancerous cells). An initial diagnosis does not include information about the stage of the cancer of the risk of prostate specific antigen failure.

As used herein, the term "biopsy tissue" refers to a sample of tissue (e.g., prostate tissue) that is removed from a subject for the purpose of determining if the sample contains cancerous tissue. In some embodiment, biopsy tissue is obtained because a subject is suspected of having cancer. The biopsy tissue is then examined (e.g., by microscopy) for the presence or absence of cancer.

As used herein, the term "inconclusive biopsy tissue" refers to biopsy tissue for which histological examination has not determined the presence or absence of cancer.

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "disease" refers to any deviation from a normal state in a subject. In preferred embodiments, the methods and compositions of the present invention are useful in the diagnosis and treatment of diseases where the immunological reaction (e.g., generation of immunoglobulins to native proteins) differs in subjects with disease and subjects not having disease. The present invention finds use with any number of diseases including, but not limited to, cancer, autoimmune disease, inflammatory disease, cardiovascular disease and diabetes.

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxygenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene that is used in conjunction with CAD-deficient cells and the mammalian hypoxanthine-guanine phosphoribosyl transferase (hprt) gene that is used in conjunction with hprt$^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer diagnosis, research and therapy, including but not limited to, cancer markers. In particular, the present invention relates to ubiquilin 1 markers for lung cancer.

However, the present invention is not limited to use in the diagnosis and treatment of cancer. The methods and compositions of the present invention find use in the diagnosis and treatment of a variety of diseases including, but not limited to, inflammatory disease, autoimmune disease, cancer, cardiovascular disease, and diabetes.

When cancer is identified at the earliest stages, the probability of cure is very high and therefore diagnostic screening tests that can detect these early stages are crucial. Tumor-associated antigens recognized by humoral effectors of the immune system are an attractive target for diagnostic and therapeutic approaches to human cancer. Efforts toward the development of early detection assays for cancers have traditionally depended on single biomarker molecule. Current technologies have been disappointing and have not resulted in diagnostic tests suitable for clinical practice.

Serologic identification of antigens by recombinant expression cloning (SEREX) has been used for identification of few types of antigen over recent years through screening expression cDNA libraries from human solid tumors with sera of the autologous patients. This type of screening of a cDNA expression library by conventional methods, however, requires the preparation of a large number of membrane filters blotted with bacteriophage plaques that are then searched with a specific probe. In the case of the SEREX experiments, the screening is performed using large amounts of sera from cancer patients, which are usually available in very limited quantity. The second limitation is that such immunoscreening procedure does not allow selection of antigens that are recognized by sera from different patients. In addition, due to the filter screening procedure, SEREX does not allow for high throughput screening and thus makes it difficult to perform replicated experiments for the selection of antigens that can be recognized by sera from a subset of cancer patients. Furthermore, SEREX relies upon a one-step screening technique without affinity selection steps (biopanning).

The methods and compositions of the present invention overcome many of these limitations. In some embodiments, the present invention provides an effective screening test to overcome these limitations and simplify the screening procedure by performing affinity selection of cDNA libraries in very small volumes using, for example, T7 phage display cDNA libraries. The platform of phage-epitope microarrays is capable of detecting over 2300 phage clones in one microarray using only microliters of sera. Highly parallel assays using different patient samples are easily compared using protein microarray technology that allows for the molecular classification of cancer based on epitomic profiles (akin to molecular profiles based on gene expression). In some embodiments, the methods of the present invention employ the recognition of a pattern of immunologic response as a diagnostic strategy. The present invention is not limited by the nature of the peptide display system used.

Phage-display technology is typically based on the insertion of foreign nucleotide sequences into genes encoding for various capsid proteins of T7 phage, resulting in a heterogeneous mixture of phages, each displaying the different peptide sequence encoded by a corresponding insert. A physical link between a displayed fusion protein and DNA encoded for it make this phage target selectable. In some embodiments, the methods of the present invention detect antibodies that are produced by patients in reaction to proteins expressed in their tumors. These markers find use as diagnostic biomarkers and therapeutic targets. In some embodiments, the methods of the present invention employ pattern recognition of multiple markers as a diagnostic rather than any single marker. Features of the approach include acknowledging the heterogeneous nature of any specific kind of cancer, and using specialized bioinformatics techniques to interpret the results.

Experiments conducted during the course of development of the present invention resulted in the detection of a serum reaction with large numbers of epitopes using a highly parallel phage display assay on protein microarrays. Once the chosen epitope markers are spotted on the final version of the array, serum from both cancer patients and controls are tested. In some embodiments, the results of the reaction of the sera with the various subjects are used to train a machine learning device to build a predictor and further to test unknown samples.

The methods and compositions of the present invention provide several advantages over existing methods. For example, in some embodiments, the methods of the present invention utilize fluorescent probes and laser scanner, resulting in high sensitivity and the detection of very small signal differences. In addition, the methods of the present invention allow for detection at the protein expression level rather than cDNA level as compared to cDNA or oligo arrays. In preferred embodiments, the methods of the present invention utilize an analytical approach rather that a visual assessment, which results in greater consistency and reproducibility. Further, due to the high sensitivity of this technique, low amounts (e.g., only 1-2 µl) of serum samples may be used. The methods of the present invention are rapid and allow for the analysis of protein-protein interactions.

I. Markers for Cancer

In some embodiments, the present invention provides markers whose expression is specifically altered in cancerous prostate tissues. Such markers find use in the diagnosis and characterization of cancer (e.g., prostate, lung or breast cancer).

A. Identification of Markers

In some embodiments, the phage expression profiling methods of the present invention (See e.g., the experimental section for a detailed description) are used to identify cancer markers or tumor antigens. Exemplary lung tumor antigens include, but are not limited to, ubiquilin 1.

B. Detection of Cancer Markers

In some embodiments, the present invention provides methods for detection of expression of cancer markers (e.g., ubiquilin 1. In preferred embodiments, expression is measured directly (e.g., at the RNA or protein level). In some embodiments, expression is detected in tissue samples (e.g., biopsy tissue). In other embodiments, expression is detected in bodily fluids (e.g., including but not limited to, plasma, serum, whole blood, mucus, and urine). The present invention further provides panels and kits for the detection of markers. In preferred embodiments, the presence of a cancer marker is used to provide a prognosis to a subject. The information provided is also used to direct the course of treatment. For example, if a subject is found to have a marker indicative of a highly metastasizing tumor, additional therapies (e.g., hormonal or radiation therapies) can be started at a earlier point when they are more likely to be effective (e.g., before metastasis). In addition, if a subject is found to have a tumor that is not responsive to hormonal therapy, the expense and inconvenience of such therapies can be avoided.

In some embodiments, the present invention provides a panel for the analysis of a plurality of markers. The panel allows for the simultaneous analysis of multiple markers correlating with carcinogenesis and/or metastasis. For example, a panel may include markers identified as correlating with cancerous tissue, metastatic cancer, localized cancer that is likely to metastasize, pre-cancerous tissue that is likely to become cancerous, and pre-cancerous tissue that is not likely to become cancerous. Depending on the subject, panels may be analyzed alone or in combination in order to provide the best possible diagnosis and prognosis. Markers for inclusion on a panel are selected by screening for their predictive value using any suitable method, including but not limited to, those described in the illustrative examples below.

In other embodiments, the present invention provides a phage array profile map comprising protein array profiles of cancers of various stages or prognoses (e.g., likelihood of future metastasis). Such maps can be used for comparison with patient samples. Any suitable method may be utilized, including but not limited to, by computer comparison of digitized data. The comparison data is used to provide diagnoses and/or prognoses to patients.

i) Detection of RNA

In some preferred embodiments, detection of prostate cancer markers (e.g., including but not limited to, ubiquilin 1) is detected by measuring the expression of corresponding mRNA in a tissue sample (e.g., lung tissue). mRNA expression may be measured by any suitable method.

ii) Detection of Protein

In other embodiments, gene expression of cancer markers is detected by measuring the expression of the corresponding protein or polypeptide. Protein expression may be detected by any suitable method. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

In other embodiments, the immunoassay described in U.S. Pat. Nos. 5,599,677 and 5,672,480; each of which is herein incorporated by reference.

iii) Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of metastasis) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may choose further intervention or counseling based on the results. In some embodiments, the data is used for research use. For example, the data may be used to further optimize the inclusion or elimination of markers as useful indicators of a particular condition or stage of disease.

C. Detection of Tumor Antigens

As described above, the presence of an immune response to specific proteins expressed in cancerous cells is indicative of the presence of cancer. Accordingly, in some embodiments, the present invention provides methods (e.g., diagnostic methods) for detecting the presence of tumor antigens identified using the methods of the present invention (e.g., Ubiquilin 1). In some embodiments (e.g., where tumor antigens are expressed in cancerous cells but not non-cancerous cells), tumor antigen proteins are detected directly. In other embodiments (e.g., where the presence of an autoantibody in cancerous but not cancerous cells is indicative of the presence of cancer), autoantibodies to the tumor antigens are detected. In preferred embodiments, tumor antigens are detected directly in tumors or cells suspected of being cancerous.

The diagnostic methods of the present invention find utility in the diagnosis and characterization of cancers. For example, the presence of an autoantibody to a specific protein may be indicative of a cancer. In addition, certain autoantibodies may be indicative of a specific stage or sub-type of the same cancer.

The information obtained is used to determine prognosis and appropriate course of treatment. For example, it is contemplated that individuals with a specific autoantibody or stage of cancer may respond differently to a given treatment than individuals lacking the antibody. The information obtained from the diagnostic methods of the present invention thus provides for the personalization of diagnosis and treatment.

i) Detection of Antigens

In some embodiments, antibodies are used to detect tumor antigens in a biological sample from an individual. The biological sample can be a biological fluid, such as, but not limited to, blood, serum, plasma, interstitial fluid, urine, cerebrospinal fluid, and the like, containing cells. In preferred embodiments, the biological sample comprises cells suspected of being cancerous (e.g., cells obtained from a biopsy).

The biological samples can then be tested directly for the presence of tumor antigens using an appropriate strategy (e.g., ELISA or radioimmunoassay) and format (e.g., microwells, dipstick (e.g., as described in International Patent Publication WO 93/03367), etc). Alternatively, proteins in the sample can be size separated (e.g., by polyacrylamide gel electrophoresis (PAGE), in the presence or not of sodium dodecyl sulfate (SDS), and the presence of tumor antigens detected by immunoblotting (e.g., Western blotting). Immunoblotting techniques are generally more effective with antibodies generated against a peptide corresponding to an epitope of a protein, and hence, are particularly suited to the present invention.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

In some embodiments, an automated detection assay is utilized. Methods for the automation of immunoassays are well known in the art (See e.g., U.S. Pat. Nos. 5,885,530, 4,981,785, 6,159,750, and 5,358,691, each of which is herein incorporated by reference). In some embodiments, the analysis and presentation of results is also automated. For example, in some embodiments, software that generates a prognosis based on the presence or absence of a series of antigens is utilized.

ii) Detection of Autoantibodies

In some embodiments, the presence of autoantibodies to a tumor antigen is detected. This approach to diagnosing and typing tumors is particularly suited to tumor antigens that are present, but not immunogenic, in normal cells and immunogenic in tumor cells. For example, in some embodiments, antibodies (e.g., monoclonal or polyclonal) are generated to the autoantibodies identified during the development of the present invention. Such antibodies are then used to detect the presence of autoantibodies using any suitable technique, including but not limited to, those described above.

In other embodiments, tumor proteins are attached to a solid surface. The presence of autoantibodies is identified by contacting the solid surface (e.g., microarray) with serum from the subject and detecting binding to a tumor marker. One exemplary method for performing such an assay is described in the experimental section below.

iii) Other Detection Methods

The present invention is not limited to the detection methods described above. Any suitable detection method that allows for the specific detection of cancerous cells may be utilized. For example, in some embodiments, the expression of RNA corresponding to a tumor antigen gene is detected by hybridization to an antisense oligonucleotide (e.g., those described below). In other embodiments, RNA expression is detected by hybridization assays such as Northern blots, RNase assays, reverse transcriptase PCR amplification, and the like.

In further embodiments of the present invention, the presence of particular sequences in the genome of a subject are detected. Such sequences include tumor antigen sequences associated with abnormal expression of tumor antigens (e.g., overexpression or expression at a physiological inappropriate time). These sequences include polymorphisms, including polymorphisms in the transcribed sequence (e.g., that effect tumor antigen processing and/or translation) and regulatory sequences such as promoters, enhances, repressors, and the like. These sequences may also include polymorphisms in genes or control sequences associated with factors that affect expression such as transcription factors, and the like. Any suitable method for detecting and/or identifying these sequences is within the scope of the present invention including, but not limited to, nucleic acid sequencing, hybridization assays (e.g., Southern blotting), single nucleotide polymorphism assays (See e.g., U.S. Pat. No. 5,994,069, herein incorporated by reference in its entirety), and the like.

Direct and/or indirect measures of tumor antigen expression may be used as a marker within the scope of the present invention. Because the present invention provides a link between tumor antigen expression and cancer, any indication of tumor expression may be used. For example, the expression, activation, or repression of factors involved in tumor antigen signaling or regulation may be used as surrogate measures of expression, so long as they are reliably correlated with tumor antigen expression and/or cancer.

D. Molecular Fingerprint

In some embodiments, the present invention provides "molecular fingerprints" or "expression profile maps" of cancer markers or tumor antigens. Such molecular fingerprints and expression profiles provide a profile of the presence of autoantibodies or cancer markers in particular cancers or cancer sub-types. The profiles find use in providing cancer diagnoses and prognoses. Such prognoses can be used to determine treatment course of action. For example, in some embodiments, the profile of a particular cancer subtype is indicative of a cancer that is responsive to a particular choice of therapy. In other embodiments, profiles are indicative of the aggressiveness of a particular cancer sub-type and are used to determine the aggressiveness of treatment to be pursued.

E. Prognostic Applications

In some embodiments, cancer markers identified using the methods and compositions of the present invention find use in providing cancer prognoses (e.g., probability of cancer metastasis, recurrence or death from cancer). In experiments conducted during the course of development of the present invention (See e.g., Examples 3 and 4) a correlation between expression profiles and cancer prognosis was observed. For example, a correlation between expression of tripartite motif-containing 7 isoform 4, cytochrome c oxidase subunit I, nucleolar protein 3 (apoptosis repressor with CARD domain), hypothetical protein AM638, putative p150, MUP1, similar to CG9996-PA, hypothetical protein Magn028940, COG0568: DNA-directed RNA polymerase, sigma subunit, IgG kappa light chain variable region and lung cancer prognosis was observed (See Example 3).

F. Kits

In yet other embodiments, the present invention provides kits for the detection and characterization of cancer (e.g., prostate, breast, or lung cancer). In some embodiments, the kits contain antibodies specific for a cancer marker or tumor antigen, in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

G. In Vivo Imaging

In some embodiments, in vivo imaging techniques are used to visualize the expression of cancer markers or tumor antigens in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers or tumor antigens of the present invention (e.g., prostate cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers or tumor antigens of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin Onc 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

II. Antibodies

The present invention provides isolated antibodies. In preferred embodiments, the present invention provides monoclonal antibodies that specifically bind to an isolated polypeptide comprised of at least five amino acid residues of the cancer markers or tumor antigens described herein (e.g., BRD2, eIF4G1, RPL22, RPL13A, HES1, hypothetical protein XP_373908, ubiquilin 1, nucleolar protein 3 (NOL3), alpha-2-glycoprotein 1 and heat shock 70 kDa protein 8 (HSPA70)). These antibodies find use in the diagnostic and therapeutic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a cancer marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is cross-linked on the carrier and used for immunization, is produced efficiently. For example, bovine serum albumin, bovine cycloglobulin, keyhole limpet hemocyanin, etc. may be coupled to a hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a cancer marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Drug Screening

In some embodiments, the present invention provides drug screening assays (e.g., to screen for anticancer drugs). The screening methods of the present invention utilize cancer markers and tumor antigens identified using the methods of the present invention. For example, in some embodiments, the present invention provides methods of screening for compound that alter (e.g., increase or decrease) the expression of cancer marker or tumor antigen genes. In some embodiments, candidate compounds are antisense agents (e.g., oligonucleotides) directed against cancer markers. See below for a discussion of antisense therapy. In other embodiments, candidate compounds are antibodies that specifically bind to a cancer marker or tumor antigen of the present invention.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker or tumor antigen mRNA expressed by the cell. mRNA expression can be detected by any suitable method. In other embodiments, the effect of candidate compounds on expression of cancer marker or tumor antigen genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers or tumor antigens of the present invention, have an inhibitory (or stimulatory) effect on, for example, cancer marker or tumor antigen expression or activity, or have a stimulatory or inhibitory effect on, for example, the expression or activity of a cancer marker or tumor antigen substrate. Compounds thus identified can be used to modulate the activity of target gene products (e.g., cancer marker or tumor antigen genes) either directly or indirectly in a therapeutic protocol, to elaborate the biological function of the target gene product, or to identify compounds that disrupt normal target gene interactions. Compounds that inhibit the activity or expression of cancer markers or tumor antigens are useful in the treatment of proliferative disorders, e.g., cancer, particularly metastatic (e.g., androgen independent) prostate cancer.

In one embodiment, the invention provides assays for screening candidate or test compounds that are substrates of a cancer marker or tumor antigen protein or polypeptide or a biologically active portion thereof. In another embodiment, the invention provides assays for screening candidate or test compounds that bind to or modulate the activity of a cancer marker or tumor antigen protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nalt. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Natl. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a cancer marker or tumor antigen protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity. The cell, for example, can be of mammalian origin.

The ability of the test compound to modulate cancer marker or tumor antigen binding to a compound, e.g., a cancer marker substrate, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker or tumor antigen is coupled with a radioisotope or enzymatic label to monitor the ability of a test compound to modulate cancer marker binding to a cancer marker or tumor antigen substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker or tumor antigen protein or biologically active portion thereof is contacted with a test compound and the ability of the test compound to bind to the cancer marker or tumor antigen protein or biologically active portion thereof is evaluated. Preferred biologically active portions of the cancer marker or tumor antigen proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 15 the assay should be maximal. An FRET binding event can be conveniently measured through standard fluorometric detection means well known in the art (e.g., using a fluorimeter).

In another embodiment, determining the ability of the cancer marker or tumor antigen protein to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anticancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker or tumor antigen protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker or tumor antigen protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the cancer marker or tumor antigen protein or biologically active portion thereof with a known compound that binds the cancer marker or tumor antigen to form an assay mixture, contacting the assay mixture with a test compound, and determining the ability of the test compound to interact with a cancer marker or tumor antigen protein, wherein determining the ability of the test compound to interact with a cancer marker or tumor antigen protein includes determining the ability of the test compound to preferentially bind to cancer markers or tumor antigens or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers or tumor antigens ("cancer marker-binding proteins" or "cancer marker-bp") and are involved in cancer marker or tumor antigen activity. Such cancer marker-bps can be activators or inhibitors of signals by the cancer marker proteins or targets as, for example, downstream elements of a cancer markers-mediated signaling pathway.

Modulators of cancer marker or tumor antigen expression can also be identified. For example, a cell or cell free mixture is contacted with a candidate compound and the expression of cancer marker or tumor antigen mRNA or protein evaluated relative to the level of expression of cancer marker or tumor antigen mRNA or protein in the absence of the candidate compound. When expression of cancer marker or tumor antigen mRNA or protein is greater in the presence of the candidate compound than in its absence, the candidate compound is identified as a stimulator of cancer marker or tumor antigen mRNA or protein expression. Alternatively, when expression of cancer marker or tumor antigen mRNA or protein is less (i.e., statistically significantly less) in the presence of the candidate compound than in its absence, the candidate compound is identified as an inhibitor of cancer marker or tumor antigen mRNA or protein expression. The level of cancer marker or tumor antigen mRNA or protein expression can be determined by methods described herein for detecting cancer marker or tumor antigen mRNA or protein.

A modulating agent can be identified using a cell-based or a cell free assay, and the ability of the agent to modulate the activity of a cancer marker or tumor antigen protein can be confirmed in vivo, e.g., in an animal such as an animal model for a disease (e.g., an animal with prostate, breast or lung cancer or metastatic prostate, breast, or lung cancer; or an animal harboring a xenograft of a prostate, lung, or breast cancer from an animal (e.g., human) or cells from a cancer resulting from metastasis of a prostate, breast, or lung cancer (e.g., to a lymph node, bone, or liver), or cells from a prostate, breast, or lung cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

IV. Cancer Therapies

In some embodiments, the present invention provides therapies for cancer (e.g., prostate cancer). In some embodiments, therapies target cancer markers or tumor antigens identified using the phage array profiling methods of the present invention (e.g., ubiquilin 1).

A. Immunotherapy

The tumor antigens identified during the development of the present invention find use in cancer immunotherapy. Such methods are improvements over the non-specific chemotherapeutic cancer therapies currently available. For example, in some embodiments, tumor antigens are used to generate therapeutic antibodies. In other embodiments, the tumor antigens of the present invention find use in the generation of cancer vaccines.

i) Antibody Immunotherapy

In some embodiments, the present invention provides therapy for cancer comprising the administration of therapeutic antibodies (See e.g., U.S. Pat. Nos. 6,180,357; and 6,051,230; both of which are herein incorporated by reference).

In some embodiments, the therapeutic antibodies comprise an antibody generated against a tumor antigen of the present invention (e.g., ubiquilin 1) conjugated to a cytotoxic agent. Such antibodies are particularly suited for targeting tumor antigens expressed on tumor cells but not normal cells. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents will serve as useful agents for attachment to antibodies or growth factors, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted to tumor antigens of the present invention. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions and described above. In preferred embodiments, administration of an antibody composition of the present invention results in a measurable decrease in cancer (e.g., decrease or elimination of tumor).

ii) Cancer Vaccines

In some embodiments, the present invention provides cancer vaccines directed against a specific cancer. Cancer vaccines induce a systemic tumor-specific immune response. Such a response is capable of eradicating tumor cells anywhere in the body (e.g., metastatic tumor cells). Methods for generating tumor vaccines are well known in the art (See e.g., U.S. Pat. Nos. 5,994,523; 5,972,334; 5,904,920; 5,674,486; and 6,207,147; each of which is herein incorporated by reference).

In some embodiments, tumor vaccines are administered when cancer is first detected (e.g., concurrently with other therapeutics such as chemotherapy). In other embodiments, cancer vaccines are administered following treatment (e.g., surgical resection or chemotherapy) to prevent relapse or metastases. In yet other embodiments, cancer vaccines are administered prophylactically (e.g., to those at risk of a certain cancer).

In some embodiments, the cancer vaccines of the present invention comprise one or more tumor antigens in a pharmaceutical composition (e.g., those described above). In some embodiments, the tumor antigen is inactivated prior to administration. In other embodiments, the vaccine further comprises one or more additional therapeutic agents (e.g., cytokines or cytokine expressing cells).

In some embodiments (e.g., the method described in U.S. Pat. No. 5,674,486, herein incorporated by reference), selected cells from a patient, such as fibroblasts, obtained, for example, from a routine skin biopsy, are genetically modified to express one or more cytokines. Alternatively, patient cells that may normally serve as antigen presenting cells in the immune system such as macrophages, monocytes, and lymphocytes may also be genetically modified to express one or more cytokines. The cytokine expressing cells are then mixed with the patient's tumor antigens (e.g., a tumor antigen of the present invention), for example in the form of irradiated tumor cells, or alternatively in the form of purified natural or recombinant tumor antigen, and employed in immunizations, for example subcutaneously, to induce systemic anti-tumor immunity.

The vaccines of the present invention may be administered using any suitable method, including but not limited to, those described above. In preferred embodiments, administration of a cancer vaccine of the present invention results in elimination (e.g., decrease or elimination of tumors) or prevention of detectable cancer cells.

B. Antisense Therapies

In some embodiments, the present invention targets the expression of cancer markers. For example, in some embodiments, the present invention employs compositions comprising oligomeric antisense compounds, particularly oligonucleotides (e.g., those identified in the drug screening methods described above), for use in modulating the function of nucleic acid molecules encoding cancer markers of the present invention (e.g., ubiquilin 1), ultimately modulating the amount of cancer marker expressed. This is accomplished by providing antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$, and $-O-N(CH_3)-CH_2-CH_2-$ [wherein the native phosphodiester backbone is represented as $-O-P-O-CH_2-$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a $O(CH_2)_2ON(CH_3)_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$.

Other preferred modifications include 2'-methoxy(2'-O—$CH_3$), 2'-aminopropoxy(2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

C. RNAi Therapies

In other embodiments, RNAi is used to regulate expression of tumor antigens or cancer markers of the present invention. RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3): 158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

C. Genetic Therapies

The present invention contemplates the use of any genetic manipulation for use in modulating the expression of cancer markers (e.g., ubiquilin 1) of the present invention. Examples of genetic manipulation include, but are not limited to, gene knockout (e.g., removing the cancer marker gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

V. Pharmaceutical Compositions

In some embodiments, the present invention provides pharmaceutical compositions that may comprise all or portions of tumor antigen or cancer marker polynucleotide sequences, tumor antigen polypeptides, inhibitors or antagonists of tumor antigen bioactivity, including antibodies, alone or in combination with at least one other agent, such as a stabilizing compound, and may be administered in any sterile, biocompatible pharmaceutical carrier, including, but not limited to, saline, buffered saline, dextrose, and water. The pharmaceutical compositions find use as therapeutic agents and vaccines for the treatment of cancer.

The methods of the present invention find use in treating cancers as described in greater detail above. Antibodies can be administered to the patient intravenously in a pharmaceutically acceptable carrier such as physiological saline. Standard methods for intracellular delivery of antibodies can be used (e.g., delivery via liposome). Such methods are well known to those of ordinary skill in the art. The formulations of this invention are useful for parenteral administration, such as intravenous, subcutaneous, intramuscular, and intraperitoneal.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, compositions (e.g., antibodies and vaccines) can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions may be administered alone to individuals suffering from cancer.

Depending on the type of cancer being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline.

For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of antibody or vaccine may be that amount that decreases the presence of cancerous cells (e.g., shrinks or eliminates a tumor or reduces the number of circulating cancer cells). Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For antibodies to a tumor antigen of the present invention, conditions indicated on the label may include treatment of conditions related to cancer.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts antibody levels.

A therapeutically effective dose refers to that amount of antibody that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference).

In some embodiments, the pharmaceutical compositions of the present invention further include one or more agents useful in the treatment of cancer. For example, in some embodiments, one or more antibodies or vaccines are combined with a chemotherapeutic agent. Chemotherapeutic agents are well known to those of skill in the art. Examples of such chemotherapeutics include alkylating agents, antibiotics, antimetabolitic agents, plant-derived agents, and hormones. Among the suitable alkylating agents are nitrogen mustards, such as cyclophosphamide, aziridines, alkyl alkone sulfonates, nitrosoureas, nonclassic alkylating agents, such as dacarbazine, and platinum compounds, such as carboplatin and cisplatin. Among the suitable antibiotic agents are dactinomycin, bleomycin, mitomycin C, plicamycin, and the anthracyclines, such as doxorubicin (also known as adriamycin) and mitoxantrone. Among the suitable antimetabolic agents are antifols, such as methotrexate, purine analogues, pyrimidine analogues, such as 5-fluorouracil (5-FU) and cytarabine, enzymes, such as the asparaginases, and synthetic agents, such as hydroxyurea. Among the suitable plant-derived agents are vinca alkaloids, such as vincristine and vinblastine, taxanes, epipodophyllotoxins, such as etoposide, and camptothecan. Among suitable hormones are steroids. Currently, the preferred drug is adriamycin. However, other suitable chemotherapeutic agents, including additional agents within the groups of agents identified above, may be readily determined by one of skill in the art depending upon the type of cancer being treated, the condition of the human or veterinary patient, and the like.

Suitable dosages for the selected chemotherapeutic agent are known to those of skill in the art. One of skill in the art can readily adjust the route of administration, the number of doses received, the timing of the doses, and the dosage amount, as needed. Such a dose, which may be readily adjusted depending upon the particular drug or agent selected, may be administered by any suitable route, including but not limited to, those described above. Doses may be repeated as needed.

VI. Transgenic Animals Expressing Cancer Marker Genes or Knockouts

The present invention contemplates the generation of transgenic animals comprising an exogenous cancer marker or tumor antigen (ubiquilin 1) gene of the present invention or mutants and variants thereof (e.g., truncations or single nucleotide polymorphisms). In other embodiments, the transgenic animals comprise a knock-out of a cancer marker or tumor antigen gene. In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

Example 1

Phage Array Profiling of Prostate Cancer

This Example describes a phage array profiling method of the present invention as applied to prostate cancer.

A. Methods

Patient Population and Samples. At the time of diagnosis and prior to radical prostatectomy, sera from biopsy-proven clinically localized prostate cancer participants were collected by the University of Michigan Specialized Research Program in Prostate Cancer (SPORE) tissue/serum bank between January 1995 to January of 2003. The average age of all prostate cancer patients was 59.6 (range 41-74). For post-prostatectomy prostate cancer patients, the average age and PSA value were 58.1 and 0.169 ng/ml respectively. Sera from lung adenocarcinoma patients (average age 53.9) without any known history of prostate cancer were used. As controls, serum samples from 85 age-matched males (average age 62.5, range 50-80) with no known history of cancer were used for the study. All sera were stored in aliquots at −20° C. until use.

Construction of T7 phage display prostate cancer cDNA libraries. Total RNA was isolated separately from six prostate cancer tissue samples according to the standard Trizol protocol (Dhanasekaran et al., Nature 412, 822-826. (2001)). The integrity of each RNA preparation was assessed by confirming that the $A_{260}/A_{280}$ ratio was greater than 1.8 and gel electrophoresis. Equal amounts of total RNA from six tissues were combined to make a pool. Poly(A) RNA was purified from the total RNA pool following Straight A's mRNA Isolation System protocol (Novagen). A total of 8.7 μg of mRNA was eluted and its integrity was judged by gel electrophoresis.

OrientExpression cDNA Synthesis and Cloning System (Novagen) was used for the construction of the T7 phage prostate cancer cDNA libraries. In order to ensure the representation of both N-terminal and C-terminal amino acid sequences and eliminate the 3' bias inherent from oligo(dT)-primed strands, equal amounts of mRNA from each was used to construct two cDNA libraries using directional oligo(dT) primers and random primers in parallel.

After vector ligation and T7 packaging, two cDNA phage display libraries were constructed and the library titers were determined by plaque assay with $4.2 \times 10_6$ pfu for the oligo (dT) primer library and $2.2 \times 10_6$ pfu for the random primer library, respectively. Phage particles from two libraries were combined to make phage library pool. After amplification, glycerol was added and the libraries were stored at −80° C.

Amplification of Libraries. Five milliliters of LB with carbenicillin was inoculated at 37° C. overnight with a single colony of BLT5615 from a freshly streaked plate. Overnight culture was added to 100 ml of LB with carbenicillin and grew to an $OD_{600}$ of 0.5. One mM of IPTG was added and the cells were allowed to grow for further 30 min. An appropriate volume of culture was infected with phage library at multiplicity of infection (MOI) of 0.001-0.01 (i.e. 100-1000 cells for each pfu). The infected bacteria were incubated with shaking at 37° C. for 1-2 hr until lysis was observed. The phage lysate was then clarified by spinning at 8000×g for 10 min. The supernatant is collected and stored at −80° C.

Biopanning for Phage-Epitope Clones Specific for Prostate Cancer. To enrich for phageepitopes that bind to IgGs specifically associated with prostate cancer, a positive and negative selection strategy was performed. First, a pre-clearing step was used to remove non-specific epitope-clones by pre-adsorbing the phage libraries onto purified IgG pool from 10 normal sera. Next, the pre-cleared phage libraries were selected onto the pool of IgGs purified from the sera of 19 localized prostate cancer patients. Protein A/G agarose beads (Pierce) were then used to purify IgGs from the sera of prostate cancer patients. Briefly, 10 μl protein-A/G agarose beads were placed into 1.5 ml eppendorf tubes and washed two times with 1×PBS. Washed beads were blocked with 1% BSA at 4° C. for 1 hr. The beads were then incubated at 4° C. with 15 μl of individual serum from control or prostate cancer patients at 1:50 dilution in 1% BSA. After incubation overnight, the beads were washed with 1×PBS by centrifuging at 1000 g for 2 min. After three washes, 10 μl of 1×PBS was added to each tube, and 10 tubes of protein A/G-IgG complex from 10 control sera and 19 tubes of prostate cancer sera were combined to make IgG pools of control and prostate cancer respectively. These control and prostate cancer IgG pools associated with protein A/G beads were stored at 4° C. as stocks for subsequent biopanning.

Twenty microliters of control IgG pool was incubated with 30 μl amplified phage library pool diluted at 1:40 with 10% BSA at 4° C. After 2 hrs, the mixture was centrifuged at 1000 g for 2 min. The beads with non-specifically bound phage particles were discarded, and the supernatant was collected. Next, the supernatant was incubated with 30 μl of the prostate cancer IgG pool at 4° C. overnight. The mixture was centrifuged at 1000 g for 2 min and the supernatant was discarded. To elute the bound phage, 100 μl of 1% SDS was added and incubated at room temperature for 10 min to break up the antibody-antigen reaction without disrupting T7 phage particles. The bound phages were removed from the beads by centrifuging at 5500 g for 8 min. Eluted phages were transferred to 10 ml culture of BLT5615 cells for amplification. Five cycles of affinity selections and biopanning were carried out for enrichment of prostate cancer-specific epitope phages.

Construction of the Phage-Epitope Microarrays. The phage library (~$10^{10}$ pfu) from the fifth cycle of biopanning was diluted at 1:$10^8$ and allowed to grow on LB agar plates with carbenicillin. A total number of 2300 random phage colonies were picked and amplified in 96-well plates. The phage lysates were spotted onto on FAST slides (Schleicher & Schuell) to make high density phage epitope microarrays using a GMS 417 printer (Affymetrix). T7 phage without any cDNA insert and anti-human IgG at 1:1000 dilution were spotted in triplicate as negative and positive controls, respectively. The arrays were dried overnight at room temperature. Before processing, the arrays were rinsed briefly in a 4% nonfat milk/PBS with 0.1% tween-20 to remove unbound phage, and then transferred immediately to 4% nonfat milk/PBS as a blocking solution for 1 hr at room temperature. Without allowing to dry, 2 ml of PBS containing human serum and T7-tag antibody (Novagen) at a dilution of 1:500 and 1:5000 respectively was applied to the surface of the slides in a screw-top slide hybridization tube. To test the specificity of the immune response, reactive serum was first quenched of non-specific activity by pre-adsorbing with 50 fold higher amount (v/v) of bacterial lysate ($OD_{600}$ of 0.5) and then used for incubation as described below. The arrays were incubated with sera from prostate cancer or control individuals for 1 hour at room temperature and then washed 5 times in PBS/0.1% Tween-20 solution for 5 min each. All washes were performed at room temperature.

After washing, the arrays were incubated with 2 ml of PBS containing Cy3-labeled goat antimouse antibody and Cy5-labeled goat anti-human antibody (Jackson ImmunoResearch) at a dilution of 1:5,000 for both for 1 hr in the dark. Five washes were performed using PBS/0.1% Tween-20 solution with 5 mins each. The arrays were dried by centrifuging at 500 g for 5 min and scanned.

Scanning and Primary Analysis of Phage-Epitope Microarrays. All slides were scanned using 532 nm and 635 nm lasers (Axon Laboratories). After scanning, the array images were quantified using GenePix software (Axon Laboratories). According to the experimental design, the median of Cy5/Cy3 was utilized so as to control the small variations in the amount of phage epitope being spotted. Ratio of Cy5/Cy3 for each spot was subtracted by median of Cy5/Cy3 of the negative T7 empty spots with the observation that the signal for the T7 empty phage on each chip highly correlated with the signal intensity for whole array. A Z-transformation was applied to clones so that the mean of each clone was zero across arrays and the standard deviation was 1.

Normalized data was subjected to two-way clustering analysis with use of Cluster and TreeView (Eisen et al., Proc Natl Acad Sci USA 95, 14863-14868 (1998)). To filter the data, the criteria of at least 1 observation with absolute values greater than 1.2 was applied and 186 clones were selected. An unsupervised hierarchical clustering analysis was performed with correlation (uncentered) similarity matrix and average linkage clustering.

Supervised Analysis of Humoral Immune Response Profiles. In order to efficiently screen hundreds of sera on phage epitope clones, a focused protein microarray comprised of 180 phage clones selected from the primary analysis of high-density epitope microarrays described above was utilized. This focused microarray included four T7 empty phages as negative controls. By employing this small microarray platform, 129 sera included 59 sera from prostate cancer patients obtained prior to prostatectomy and 70 control sera from age-matched males were screened as mentioned above.

The entire dataset from 129 samples was used to build a class prediction model by a leave one out cross-validation (LOOCV) strategy in genetic algorithm/K-nearest neighbors (GA/KNN) (k=3 in this study) method (Li et al., 4, 727-739 (2001)). The raw phage-epitope microarray data was normalized as described for the high-density epitope microarrays. The normalized array data was then applied to GA for selection of feature epitopes and assessment of the relative predictive importance of the epitope by ranking them based on their frequency of occurrence in GA solutions. Different numbers of the top-most epitopes were used to build a different KNN prediction model.

Prediction accuracy and error were calculated using LOOCV to evaluate the performance of different KNN model. Finally, a top-ranked 22 clones were selected based on their best performance on specificity and sensitivity. Prediction sensitivity and specificity were computed based on the number of misclassified samples in the cancer and control groups.

Class Prediction on Independent Data. A weighted voting scheme was adopted to predict "test samples", as described previously (Golub et al., Science 286, 531-537 (1999)). Briefly, each epitope in the feature set casts a weighted vote for a class 0 or 1: $V_x=T_x(e_x-b_x)$ where $e_x$ is expression value of epitope x, $T_x$ is the t-statistic for comparing the two class means of epitope x in the training set, and $b_x$ is $(\mu_{class0}+\mu_{class1})/2$. The final vote for class 0 or 1 is sign $(\Sigma_x V_x)$ and the prediction strength (PS) or confidence in the prediction of the winning class is $(V_{win}-V_{lose})/(V_{win}+V_{lose})$, where Vi is the votes for class i.

Statistical Analysis. Principal Components Analysis (PCA) (Crescenzi and Giuliani, FEBS Lett 507, 114-118 (2001)) was applied on the epitomic profiles of the 22 phage clones. The first five components contained 90% of the variation in the data set and were subsequently used as covariates in the logistic regression fitting cancer versus normal as binary diagnostic outcome. Fitted probabilities were obtained and used to generate the ROC curve to assess the prediction accuracy of the epitomic profile. All statistical analysis was performed with SPSS 11.1 (SPSS Inc). The mean values for phage epitope humoral response were presented as mean plots with the error bars signifying a 95% confidence interval of the mean. P values less than 0.05 were considered statistically significant.

Sequence Analysis of Humoral Response Candidates. The top 22 phage epitope clones were amplified by PCR using T7 capsid forward and reverse primers (Novagen). Briefly, 2 µl of fresh phage lysate with titer of ~$10^{10}$ pfu was incubated with 100 µl of 10 mM EDTA, pH 8.0 at 60° C. for 10 min. After centrifuging at 14,000×g for 3 min, 2 µl of denatured phage was used for PCR in 100 µl volume of reaction under standard condition. PCR products were confirmed on 1% agarose gel containing ethidium bromide. After purifying with Multi-Screen-FB filter plate (Millipore) following manufacturer's protocol, PCR products were sequenced using T7 capsid forward primer to determine the cDNA inserts. DNA sequence and potential protein sequence were aligned using NCBI BLAST.

Development of an ELISA to Validate Humoral Response Candidates. ELISAs were developed for the phage epitopes to confirm their immunoreactivity with different patient serum. Ninety-six well MAX-SORB microtiter plates (NUNC) were coated with 100 µl of diluted T7-tag antibody (Novagen) using 1×PBS at 1:1000 overnight at 4° C. on an orbital shaker. All the additions were in 100 µl volumes unless otherwise mentioned. Dilutions of serum and secondary detection reagents were carried out in 1:5 HPE buffer (R&D systems). After washing 5 times with PBS/Tween-20 using EL404 microplate autowasher (Bio-Tek), the plates were blocked first with 200 µl of 2% BSA/PBS for 2 hrs followed by 200 µl of superblock (Pierce) for 2 mins, both at room temperature. Phages and the T7 empty phage as negative control were separately diluted at 1:25 to a final titration of ~$10^9$ pfu. After washing as above, the plate was incubated with 100 µl of diluted phages for 2 hrs at RT. Serially diluted (1:500, 1:1000 and 1:2000) serum samples were added to each well, and incubated for 1 hr at RT. After washing, the plates were then incubated with 1:10000 diluted HRP-conjugated anti-human IgG for 1 hr at RT. The plates were then developed using 100 µl TMB substrate system (Sigma) for 30 min after final washing. The reaction was stopped using 50 µl of 1.5 M $H_2SO_4$ and read at 450 nm using ELx 800 universal microplate reader (Bio-Tek).

Meta-Analysis of Gene Expression of Humoral Response Candidates. The gene expression level of four genes, namely BRD2, eIF4G1, RPL13A and RPL22, were studied using ONCOMINE. Briefly, each gene was searched on the database, and the results were filtered by selecting prostate cancer. The data from study class of benign prostate, prostate cancer and/or metastatic prostate cancer with p<0.05 were used to plot the box plots with SPSS11.1. P values for each group were calculated using student t-test.

Immunoblot Analysis. Tissues were homogenized in NP-40 lysis buffer containing 50 mmol/L Tris-HCl, pH 7.4, 1% Nonidet P-40 (Sigma) and complete protease inhibitor cocktail (Roche). Fifteen µg of protein extracts were mixed with SDS sample buffer and electrophoresed onto a 4-15% linear gradient SDS-polyacrylamide gel under reducing conditions. The separated proteins were transferred onto polyvinyl difluoride membranes (Amersham). The membranes were then incubated for 1 hour in blocking buffer (Tris-buffered saline with 0.1% Tween (TBS-T) and 5% nonfat dry milk). Membranes were incubated with purified eIF4G1 rabbit polyclonal at 1:4000 dilution (Bethyl), RPL22 mouse monoclonal (BD biosciences) at 1:400 dilution, BRD2 rabbit polyclonal (Abgent) diluted at 1:400 and RPL13a rabbit polyclonal (kind gift of Dr. Paul Fox) used at 1:4000 dilution and incubated overnight at 4° C. After washing three times with TBS-T buffer, the membrane was incubated with horseradish peroxidase-linked donkey anti-rabbit IgG or rabbit anti-mouse IgG HRP conjugate (Amersham) at 1:5000 for 1 hour at room temperature.

After washing the blots with TBS-T and TBS, the signals were visualized with the ECL detection system (Amersham) and autoradiography. To monitor equal loading, the membranes were incubated with anti-human GAPDH antibody (Abcam) at 1:25,000 dilution for two hours and the signals were visualized.

Tissue microarray (TMA) and Immunohistochemistry. In order to determine the expression of eIF4G1 protein in situ across a wide range of prostate tissues, a prostate cancer progression TMA composed of benign prostate tissue, localized prostate cancers and metastatic prostate cancer was employed. Antigen retrieval was carried out by heating the slides in citrate buffer pH 6.0 in a microwave oven for 15 minutes. Rabbit anti-eIF4G1 (Bethyl) antibodies were applied (1:100 dilution) and incubated for 1 hour at room temperature. Secondary anti-mouse antibodies avidin-conjugated were applied before washing. Enzymatic reaction was completed using a streptavidin biotin detection kit (Dako).

Immunofluorescence and confocal microscopy. The prostate cancer tissue section slides were soaked in xylene to remove paraffin. Antigen was retrieved by heating the slides in citrate buffer pH6.0 for 15 minutes in a pressure cooker. The slides were then blocked in PBS-T with 5% normal donkey serum for 1 hour. A mixture of rabbit anti-eIF4G1 (Bethyl) antibody and mouse anti-Ecadherin (BD biosciences) antibody was added to the slides at 1:40 and 1:250 dilutions respectively and incubated for 1 hour at room temperature. Slides were then incubated with secondary antibodies (anti-mouse Alexa 488 and anti-rabbit Alexa 555 at 1:1000 dilution) were incubated for 1 hour. After washing the slides with PBS-T and PBS, the slides were mounted using vectashield mounting medium containing DAPI. Confocal images were taken with Ziess LSM510 META (Carl Zeiss) imaging system using ultraviolet, Argon and Helium Neon 1 light source. The triple color images were exported as TIFF images and color balanced.

B. Results

An overview of the method used in the present invention to identify epitomic biomarkers of prostate cancer is described in FIG. 1. To develop a T7 phage display library for prostate cancer, RNA was isolated from prostate cancer tissues derived from six patients with clinically localized disease (three patients with Gleason grade 6 and three patients with Gleason grade 7 prostate cancer). To generate a wide range of epitopes (both representing C-terminal and N terminal epitopes), parallel libraries were constructed using oligo(dT) and random primers.

Once packaged into the T7 phage system, epitopes from the library were expressed as a fusion protein with the capsid 10B protein on the surface of the phage. This serves as "bait" to capture potential autoantibodies found in serum. To enrich for epitopes that specifically generate a humoral response in prostate cancer patients, the phage-epitope libraries were subjected to five rounds of biopanning (FIG. 1). In order to remove non-specific immunoreactivity, the phage epitope particles were pre-adsorbed to a pool of immunoglobulins (IgG) isolated from ten control individuals. The "flow-thru" or nonbonding supernatant was then enriched for prostate cancer-specific epitopes by incubating with IgGs from a pool of 19 patients with clinically localized prostate cancer (see FIGS. 4, 5, and 6 for clinical and pathological information for patients). Protein A/G beads were used to isolate phage-epitope particles that specifically bound antibodies from prostate cancer patients. The bound phages were eluted and amplified in bacteria, thus completing one round of biopanning (FIG. 1). After five rounds of biopanning, it is expected that the pool will be enriched for epitopes that specifically elicit a humoral immune response in prostate cancer patients. Approximately 2300 (2.3K) phage-epitope clones were selected randomly from the biopanned material in order to generate protein microarrays. Once in a microarray format, these enriched phage epitope clones are used to interrogate serum samples for humoral immune response markers.

Using this 2.3K phage-epitope microarray, sera from prostate cancer patients and controls was evaluated. A two-color system was used in which a green fluorescent dye (Cy3) was used to measure levels of the capsid 10B fusion protein as a control for protein spotting, and a red fluorescent (Cy5) was used to measure levels of bound IgG (FIG. 1). Therefore, increased Cy5/Cy3 ratios represented varying levels of immune reactivity. As an initial discovery approach, 31 serum samples consisting of 20 sera from prostate cancer patients and 11 controls were evaluated. Most of the sera from prostate cancer patients exhibited antibody repertoires that reacted with phage-epitope clones on the microarrays while most of the controls did not. After normalization, the data was filtered for elements that have a Cy5/Cy3 ratio with an absolute value greater than 1.2 in at least one of the serum samples. This resulted in 186 phage-epitope clones, which were used for subsequent analyses. Using an unsupervised learning method, Cy5/Cy3 values from these immunoreactive clones were hierarchically clustered. The sera from prostate cancer patients and those from controls segregated into two predominant clusters. Samples in the cluster containing primarily sera from prostate cancer patients, exhibited a robust humoral response to specific phage epitope clones (represented by intensities of yellow color). In this set of 31 sera there was one mis-classified sample from both the prostate cancer cohort as well as the control group. This resulted in a sensitivity and specificity of 95% and 91%, respectively.

To expand the population of sera tested, a focused phage-epitope microarray consisting of the 180 of clones used in the unsupervised analysis (above) as well as additional control elements (i.e., T7 empty phage) was developed. Using these focused protein microarrays, 129 serum samples including 59 patients with biopsy-confirmed prostate cancer and 70 controls were evaluated. Unsupervised analysis using the total 176 epitope clones (excluding four negative clones) revealed 80% specificity and 83% sensitivity for 129 serum samples (see FIG. 7). To increase the classification accuracy, a class prediction model was developed by employing a non-parametric pattern recognition approach, Genetic Algorithm (GA) combined with k-Nearest Neighbor (KNN), to discriminate different serum samples. The predictive importance of each epitope for sample classification was evaluated and the epitopes were then ranked with the top-most epitope assigned a rank of 1. Eleven different KNN class prediction models were constructed using different numbers of the top-most epitopes (10, 20-26, 30, 50, and 100 features) to evaluate their predictive performances by leave-one-out-cross-validation. The prediction accuracy improved as more epitopes were involved in the models, whereas too many epitopes introduced excess error in the model thus decreasing the prediction accuracy. The 22 phage epitope clones yielded the best performance in classifying the serum samples with 97% specificity (2 out of 70 controls misclassified) and 88% sensitivity (7 out of 59 prostate cancer patients mis-classified). Thus, in a substantially larger cohort of sera, it was possible to predict prostate cancer status based on the humoral response to 22 phage epitopes.

Figure 2:
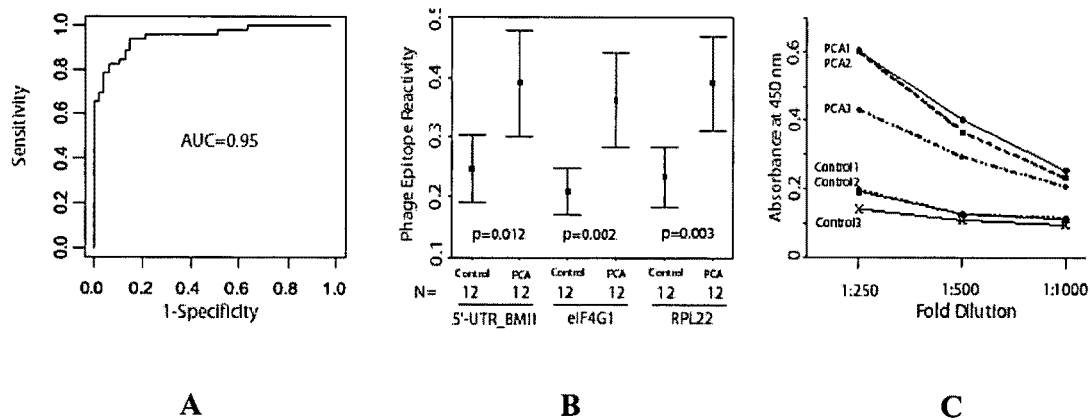
FIG. 2 shows supervised analyses and validation of humoral immune response candidates of prostate cancer. FIG. AB shows a Receiver Operator Characteristic (ROC) curve based on multiplex analysis of the 22 epitomic biomarkers. AUC, area under the curve.

The receiver operator characteristics (ROC) of a multiplex panel of humoral response markers was next evaluated to assess prediction accuracy. In order to develop an ROC curve, the 22 predictive phage epitope biomarkers were considered as covariates and the dimension of the dataset from humoral immune response was reduced by principal components analysis (PCA). The first five components accounting for 90% of the variation were applied to logistic regression to predict prostate cancer versus control. The fitted probabilities from the logistic model (p<0.001 for the overall model) were used as threshold points to calculate sensitivities and specificities (FIG. 2A). The area under the curve equaled 0.95.

The 22 top discriminating clones identified by supervised analysis were sequenced. Six out of the 22 clones were found to be in-frame and in known expressed sequences. These Six included Bromodomain Containing Protein 2 (BRD2), Eukaryotic Translation Initiation Factor 4 Gamma 1 (eIF4G1), Ribosomal Protein L22 (RPL22), Ribosomal Protein L13A (RPL13A), HES1 (hairy and enhancer of split 1, homolog of Drosophila), and hypothetical protein XP_373908. None of these proteins have been associated with prostate cancer previously as either an over-expressed protein or as a humoral response target. Except hypothetical protein XP_373908, four of the in-frame phage-epitope clones were intracellular proteins involved in regulating transcription or translation in rapidly growing cells. BRD2, also known as RING3, is a nuclear transcription factor kinase known to be up-regulated in human leukemias (Denis and Green, Genes Dev 10, 261-271 (1996); Denis et al., Cell Growth Differ 11, 417-424 (2000)). BRD2 has been shown to specifically interact with acetylated lysine 12 on histone H4 (Kanno et al., Mol Cell 13, 33-43 (2004)). Initiation factors of the eIF4 group are important in the recognition of the 5' cap region of messenger RNAs (mRNA) as well as unwinding of mRNA structure (Gingras et al., Genes Dev 15, 807-826 (2001)). Among them, eIF4G1 plays a central role in the assembly of the preinitiation complex (Morino et al., Mol Cell Biol 20, 468-477 (2000)). eIF4G1 has been shown to be overexpressed in head and neck squamous cell carcinoma (Cromer et al., Oncogene (2003)) and squamous lung carcinoma patients (Bauer, C. et al. Int J Cancer 98, 181-185 (2002); Bauer et al., Cancer 92, 822-829 (2001)) and produces a humoral immune response (Brass et al., Hum Mol Genet. 6, 33-39 (1997)). Overexpression of eIF4G1 has been shown to transform NIH3T3 cells (Fukuchi-Shimogori et al., Cancer Res 57, 5041-5044 (1997)). RPL22 and RPL13A are cytoplasmic ribosomal proteins that are the components of the 60S subunit (Mazumder et al., Cell 115, 187-198 (2003)). RPL22 has been shown to be overexpressed in lung cancer (Miura et al., Cancer Res 62, 3244-3250 (2002); Racz et al., Eur J Cancer 35, 641-646 (1999)). RPL13a was identified as a candidate interferon-Gamma Activated Inhibitor of Translation (GAIT) and thus mediates transcript-specific translational control (Mazumder et al., supra). HES1 is basic helix-loop-helix transcription factor of the achaete-scute family. Human achaete-scut homolog 1 (hASH1) is highly expressed in neuroendocrine cancers such as medullary thyroid cancer and small cell lung cancer. HES1 genes encode helix-loop-helix transcription repressors with structural homology to the Drosophila hairy and Enhancer-to-split. HES1 protein is detected at abundant levels in most non-neuroendocrine human lung cancer cell lines.

The remaining 17 prostate cancer specific phage epitope clones were either in un-translated regions of expressed genes or out of frame in the coding sequence of known genes (see FIGS. 11 and 12)). These clones likely represent "mimotopes" or epitopes that are structurally similar to expressed proteins but unrelated or weakly related at the protein sequence level. Three of the remaining 17 discriminating clones represented an epitope encoded by overlapping sequence from the 5' un-translated region (UTR) of the BMI1 gene (5'-UTR_BMI1), which is a Polycomb Group (PcG) protein implicated in various cellular processes including self-renewal (Park et al., Nature 423, 302-305 (2003); Molofsky et al., Nature 425, 962-967 (2003)). PcG proteins function as multi-component complexes. Protein BLAST analysis of the peptide sequence shared by the three phage clones representing the 5'-UTR_BMI1 identified significant homology (E value=$5 \times 10_{-4}$) to a glycine-rich stretch of the androgen receptor (FIG. 12). Androgens are known to play an important role in prostate cancer progression (Singh and Figg, Cancer Biol Ther 3 (2004); Taplin et al., J Cell Biochem 91, 483-190 (2004)). This was the only phage epitope clone picked up by the methods of the present invention that was represented by multiple independent clones suggesting consistency and robustness of this humoral response in prostate cancer patients (FIG. 2B, C). In 1985, Liao and Witte reported that that 37% of males and only 3% of females had significant autoantibodies to androgen receptor (Liao and Witte, Proc Natl Acad Sci USA 82, 8345-8348 (1985)). Males older than 66 more often had higher-titer autoantibodies to androgen receptor than younger males or females.

To validate the observations we made using phage-epitope protein microarrays, an ELISA was generated using three of the phage epitope clones including the 5'-UTR_BMI1, eIF4G1 and RPL22. Phage particles were purified and coated onto 96-well plates for subsequent incubation with representative sera from prostate cancer patients and controls. As shown in FIG. 2B, prostate cancer patients produce a humoral response to these epitopes relative to controls. Titration of the humoral immune response to the 5'-UTR_BMI1 clone is shown as a representative example in FIG. 2C.

In order to validate the 22-clone epitomic profile, an independent cohort of sera from 48 clinically localized prostate cancer patients (pre-prostatectomy), 14 prostate cancer patients (post-prostatectomy), 11 hormone refractory prostate cancer patients, 15 age-matched controls and 10 lung cancer patients was employed. A prediction model was built by a weighted voting algorithm using the 22 phage epitope profile derived from the "training" cohort of 129 samples (FIG. 8). As an independent test cohort, a class prediction was made for 63 samples (48 localized prostate cancer and 15 controls) using this model (FIG. 9). In total, only 2 out of 15 controls and 8 out of 42 cancers were misclassified, which resulted in 87% specificity and 81% sensitivity. An additional 6 cancer samples were considered as unclassified due to a low prediction strength (confidence) of 0.1 (See FIGS. 8, 9 and 10). After prostatectomy, the humoral response was generally decreased especially in patients that did not exhibit a recurrence suggesting that the immune response is attenuated upon removal of the "immunogen". 4/4 patients that exhibited PSA recurrence post-prostatectomy, also maintained the 22-epitope humoral response. Only 3 out 11 patients with hormone-refractory disease exhibited a humoral response to the 22 selected epitopes. This suggests that the humoral immune response is attenuated in advanced prostate cancer or those patients treated with anti-androgens and/or chemotherapeutics. To determine if this 22-epitope profile is specific to prostate cancer, sera from 10 lung cancer patients was also examined. Only 2/10 sera from lung cancer patients exhibited reactivity to the prostate cancer epitopes. This is in contrast to the over 80% sensitivity achieved for prostate cancer patients using this platform, suggesting that the epitomic profile is prostate cancer-specific (proportion test, P<0.001).

Figure 3A:
FIG. 3A shows a heatmap representation of the humoral immune response for four in frame phage-epitope clones assessed across 129 serum samples.
Figure 3B:
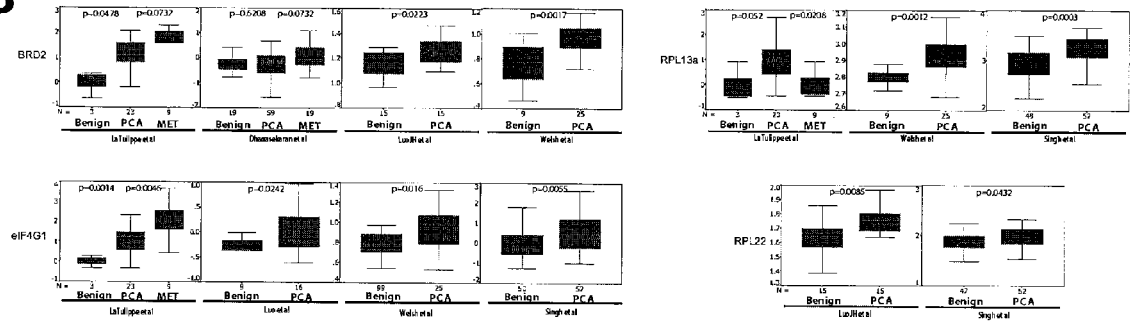
FIG. 3B shows the relative gene expression levels of in frame phage-epitope clones assessed using publicly available DNA microarray data housed in ONCOMINE.
Figure 3C:
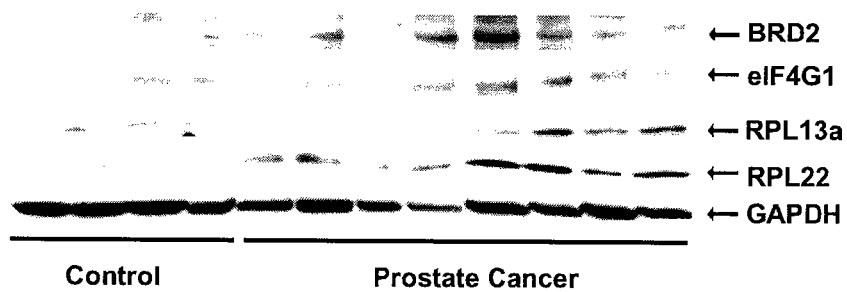
FIG. 3C shows immunoblot validation of the overexpression of humoral response candidates at the protein level in prostate cancer.

To determine whether the four in-frame phage epitope clones (FIG. 3A) are dysregulated in prostate cancer, a meta-analysis of publicly available prostate cancer gene expression data was performed (LaTulippe et al., Cancer Res 62, 4499-4506 (2002); Luo et al., Mol Carcinog 33, 25-35 (2002); Luo et al., Cancer Res 61, 4683-4688. (2001); Singh et al., Cancer Cell 1, 203-209. (2002); Welsh et al., Cancer Res 61, 5974-5978. (2001); Dhanasekaran et al., supra). This in silico analysis suggested there was ample evidence in multiple profiling studies for over-expression of the four in-frame phage epitope clones (FIG. 3B). Immunoblot analyses of benign prostate and prostate cancer tissue extracts demonstrated overexpression of these humoral response candidates at the protein level confirming the in silico analyses (FIG. 3C).

To assess the expression of the humoral response candidates in situ, immunohistochemistry and immunofluorescence analysis was performed. One out of the four antibodies used for immunoblot analysis (FIG. 3C) were compatible for tissue staining purposes. The antibody that was successful for these applications was directed against the eIF4G1 protein. Weak cytoplasmic staining of eIF4G1 was observed in benign prostate epithelia, and strong staining was observed in clinically localized prostate cancer. These immunohistochemical analyses were further confirmed by immunofluorescence staining for eIF4G1. A strong cytoplasmic staining of eIF4G1 was observed in prostate cancer epithelia as compared to negative staining in benign epithelia.

In summary, the present example describes a robust approach of combining phage display with protein microarrays to detect cancer based on the endogenous humoral immune response. As this approach relies on a multiplex set of markers, it is less likely to suffer from the drawbacks of monitoring single biomarkers such as PSA.

Example 2

Breast Cancer Detection by Epitomic Profiling of the Humoral Immune Response

This Example describes an investigation of the humoral immune signature in breast cancer. The phage display breast cancer cDNA library was purchased commercially from Novagen. The library was enriched for breast cancer specific phage epitopes using a pool of IgG from 10 breast cancer sera and 10 normal controls. A total of 2,304 phage clones were picked and printed on slides to make a high-density phage epitope microarray. By applying this platform, 77 sera samples were screened, including 42 breast cancers and 35 normal controls. The images and data were analyzed and normalized as for prostate cancer (See Example 1). In order to build a predictor, a total of 28 cancers and 24 controls were randomly selected and assigned as training set, and the remaining 14 cancers and 11 controls served as test set. The best performing clones were selected from the training set by t-test with 1000× permutation. A total of 21 clones were selected with 81% specificity (5/24) and 79% sensitivity (6/28). When applying these 21 phage epitopes on independent test set, the same level of accuracy was achieved with 91% specificity (10/11) and 50% sensitivity (7/14).

Example 3

Figure 13:
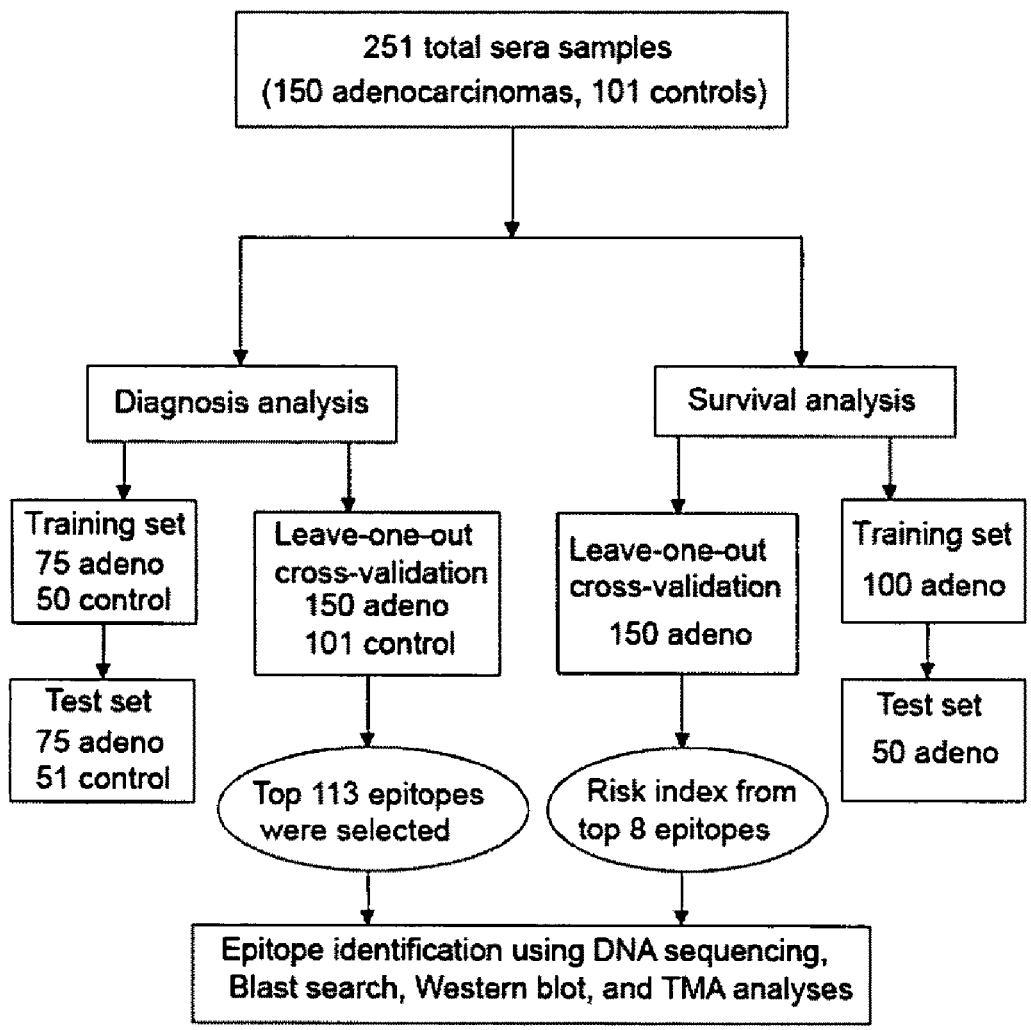
FIG. 13 shows a schematic of the approach used to identify epitomic biomarkers of lung cancer in some embodiments of the present invention.

Humoral Immune Response Profiles Associated with Diagnosis and Prognosis in Lung Adenocarcinomas A. Construction of Phage-Epitope Protein Microarray The approach described above for profiling of prostate cancer (See Example 1) was used to identify epitomic biomarkers of lung cancer (FIG. 13). To develop a phage display library for lung cancer, total RNA was isolated from 7 lung cancer tissues (3 lung adenocarcinomas and 4 squamous). The phage library was then enriched by affinity purification (biopanning) using individual serum samples from 6 adenocarcinomas, 4 squamous and 3 non-cancer controls. Thus, a total of 13 enriched phage libraries were created. After four rounds of biopanning, epitopes that specifically elicit a humoral immune response in lung cancer patients or controls were enriched for. Totally, 2304 phage-epitope clones were selected randomly from the 13 biopanned libraries in order to generate epitope microarrays. Once in a microarray format, these enriched phage epitope clones were used to interrogate serum samples for humoral immune response markers.

Using this high-density phage-epitope microarray platform, sera from 150 lung adenocarcinomas and 101 non-cancer controls were evaluated. As described above (See Example 1), a two-color system was employed in which a green fluorescent dye (Cy3) was used to measure levels of the capsid 10B fusion protein as a control for protein spotting, and a red fluorescent (Cy5) was used to measure levels of bound IgG. Therefore, increased Cy5/Cy3 ratios represented varying levels of immune reactivity. After normalization, data were used for subsequent diagnosis and survival analyses. Results are shown in Tables 1 and 2.

TABLE 1

Clinical information for Training/Test set samples

|  | Training set | Test set |
|---|---|---|
| Adenocarcinomas (n) | 75 | 75 |
| Age average (year) | 63.6 | 66.3 |
| Age range | 44-90 | 34-88 |
| Male | 37 | 37 |
| Female | 38 | 38 |
| stage I-II | 57 | 59 |
| stage III-IV | 18 | 16 |
| Dead | 35 | 33 |
| Alive | 40 | 42 |
| survival time (ms) | 31.5 | 32.4 |
| No-cancer control (n) | 50 | 51 |
| Age average (year) | 60.8 | 60.8 |
| Age range | 36-77 | 40-77 |
| Male | 30 | 31 |
| Female | 20 | 20 |

TABLE 2

Prediction accuracy of training and test sets

|  | Training set | Test set |
|---|---|---|
| Sensitivity | 82.7% (62/75) | 82.7% (62/75) |
| Specificity | 94.0% (47/50) | 84.3% (43/51) |
| Accuracy | 87.2% (109/125) | 83.3% (105/126) |

For diagnosis analysis, 251 samples were first randomly assigned to training set (75 tumors and 50 controls) and test set (75 tumors and 51 controls) with matched age, sex, stage and survival (FIG. 13 and Table 1). In the training set, t-test combined with leave-one-out-cross-validation (LOOCV) was performed to build a class prediction model, and the top-ranked 59 epitope clones were selected based on their best performance on 82.7% (62/75) sensitivity and 94.0% (47/50) specificity (Table 2). Prediction sensitivity and specificity were computed based on the number of misclassified samples in the cancer and control groups. This prediction model consisting of 59 phage-epitopes was then applied to the independent test set. The test samples were correctly classified into cancer and normal groups with 82.7% (62/75) sensitivity and 84.3% (43/51) specificity, respectively (Table 2).

Figure 14:
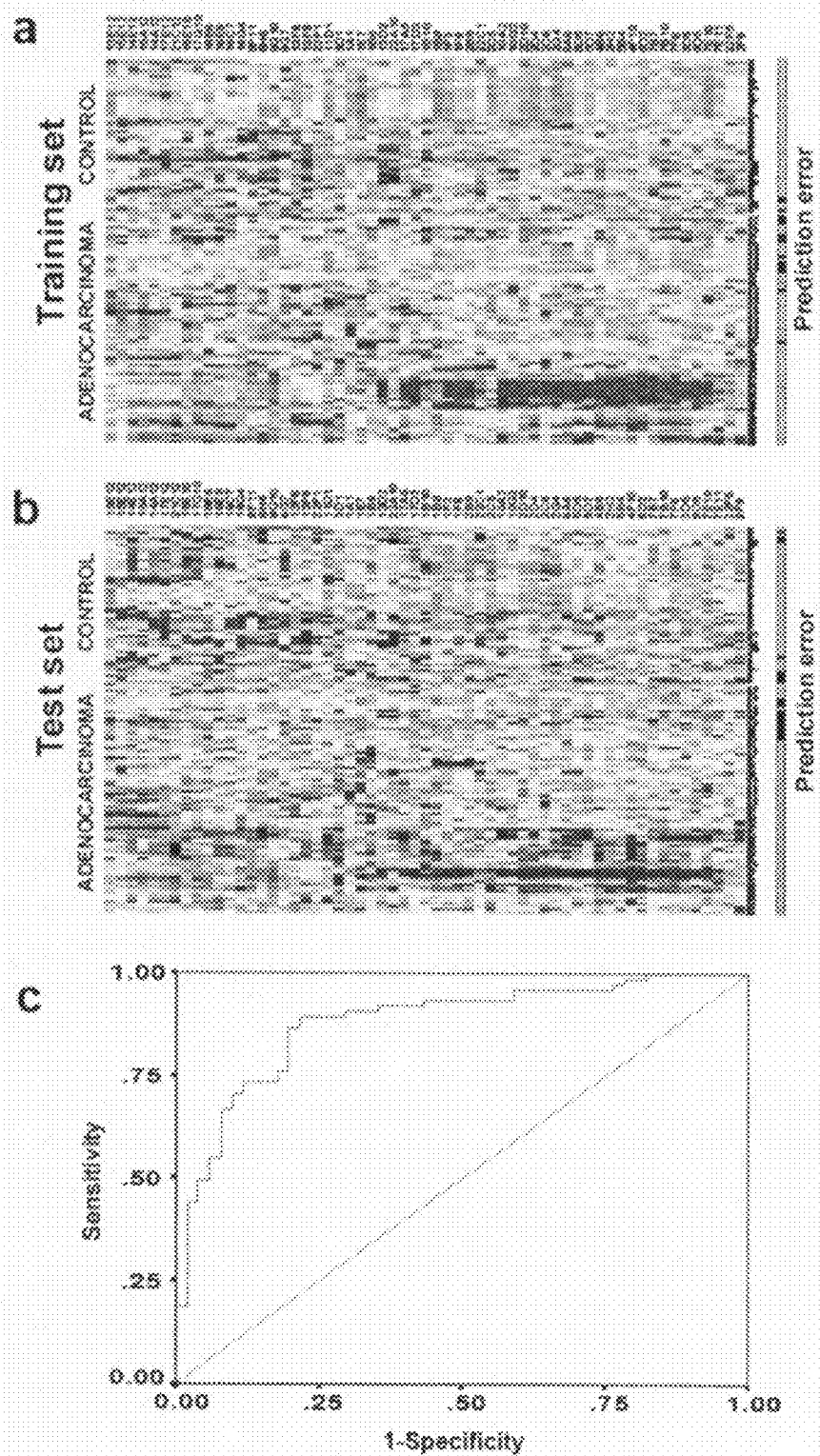
FIG. 14 shows performance of the immune response profile in the test set.

In order to investigate the predictive performance of the immune response profile, receiver operator characteristics (ROC) analysis was performed using the 59 phage-epitopes derived from the training set to assess the prediction accuracy in the test set. The discriminative ability of the panel of 59 phage-epitopes between cancers and controls was statistically significant (p<0.0001) with an area under the curve (AUC) equal to 0.88 (95% CI=0.82 to 0.94) (FIG. 14).

A leave-one-out cross-validation approach was performed on entire 251 samples (150 tumors and 101 controls) to select the best diagnosis related phage epitopes. The top-ranked 113 clones were found to give the best predict values with 83% ($^{125}/_{150}$) sensitivity and 87.1% ($^{88}/_{101}$) specificity.

B. Humoral Immune Response Profiles Predict Survival

The association between phage epitopes and patient survival was next investigated. First, the 150 cancer samples were randomly assigned to a training (n=100) set and test set (n=50) with matched stage and dead/alive. LOOCV with Cox proportional-hazard regression model was used to select the survival related epitopes in the training set. An epitope risk index was created from 7 top-ranked survival related clones based on median cutoff point of the index, which give the best overall survival prediction in the training set (P=0.004, FIG. 15a). The risk index and cutoff point were then applied to the test set. This risk index of the top 7 clones correctly identified low- and high-risk individuals within the independent test set (P=0.02, FIG. 15b).

Figure 15:
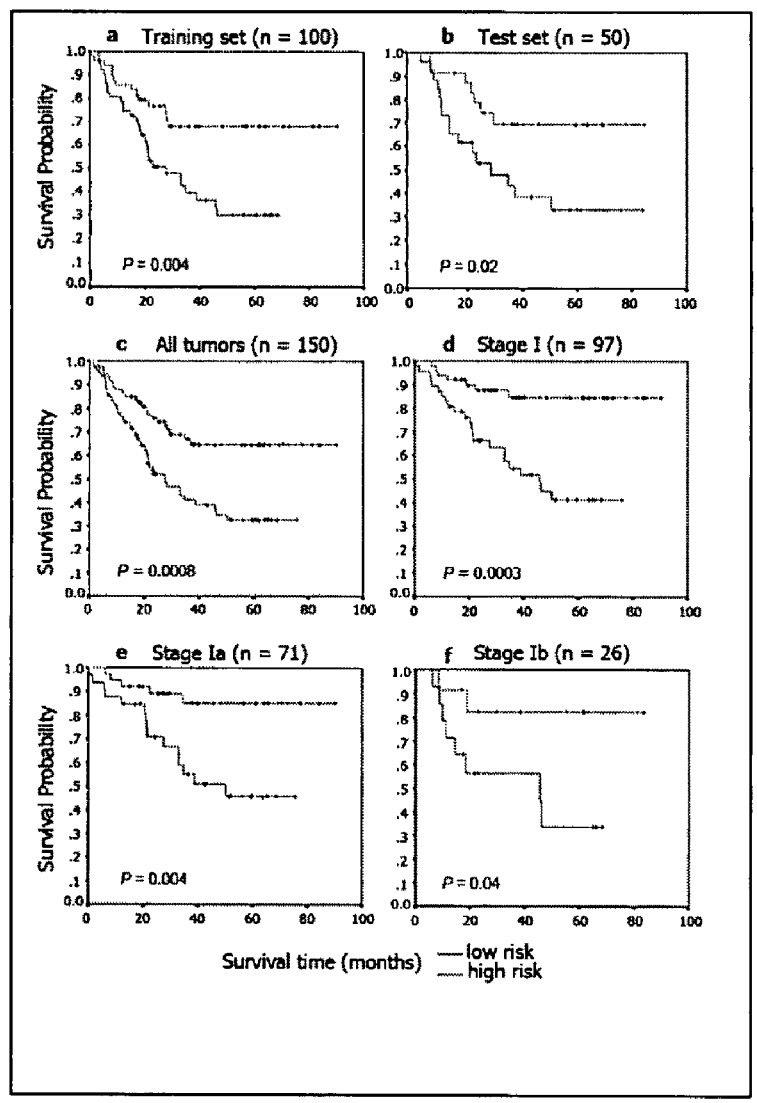
FIG. 15 shows humoral immune response profiles and patient survival.

In order to select the most robust set of survival related clones, the LOOCV approach was used to identify epitopes associated with survival from all 150 tumor samples. A risk index of the top 8 clones can significantly separate 150 patients to high- and low-risk groups (median cutoff point, P=0.0008, FIG. 15c). This risk index can also predict patients with stage I, Ia or Ib cancer (FIGS. 15d, e and f). Further analysis with univariate Cox model showed that patient stage, T or N status were also related to survival, but age and sex were not (Table 3). To analyze whether this epitope risk index is an independent factor from other clinical variables, multivate Cox model was performed on age, sex, stage and risk index. The result showed that this epitope risk index is an independent survival predictor (P=0.003, Table 4).

TABLE 3

Univariate Cox's proportional hazards model

| Variable | P value |
|---|---|
| Age | 0.96 |
| Sex | 0.48 |
| Stage II | 0.02 |
| III-IV | <0.0001 |
| T status | 0.02 |
| N status | <0.0001 |
| Epitope Risk index | 0.0008 |

TABLE 4

Multivariate Cox's proportional hazards model

| Variable | HR | 95% CI | P value |
|---|---|---|---|
| Age | 1.02 | 0.999-1.05 | 0.06 |
| Sex | 1.13 | 0.693-1.85 | 0.6 |
| Stage II | 2.61 | 1.233-5.54 | 0.01 |
| Stage III-IV | 5.89 | 3.352-10.35 | <0.00001 |
| Epitomic risk index | 2.23 | 1.328-3.76 | 0.003 |

C. Identification of Phage Epitopes

The phage display peptide microarray strategy allows for the easy identification of humoral response targets by sequencing and BLAST searching. The top 400 clones identified by previously LOOCV analysis based on all samples were sequenced (Table 5). Some sequences were found to be in-frame of known protein sequence, such as ubiquilin 1, nucleoar protein 3 (NOL3), alpha-2-glycoprotein 1 and heat shock 70 kDa protein 8 (HSPA70). Most of the humoral immuno response peptide targets were mimotopes.

Among the in-frame known proteins, heat shock 70 kDa protein was previously reported to be a humoral immune response target in lung cancer by another group. Two different sizes (113-197 and 113-219 CDS region) of HSP70 were found with the same humoral immune response pattern. Three clones of nucleoar protein 3 and alpha-2-glycoprotein 1 were uncovered respectively although the serum antibody to NOL3 was decreased in tumors as compared to no-cancer controls and this humoral immune response was related to an unfavorable survival in lung adenocarcinomas (P<0.006).

Figure 16:
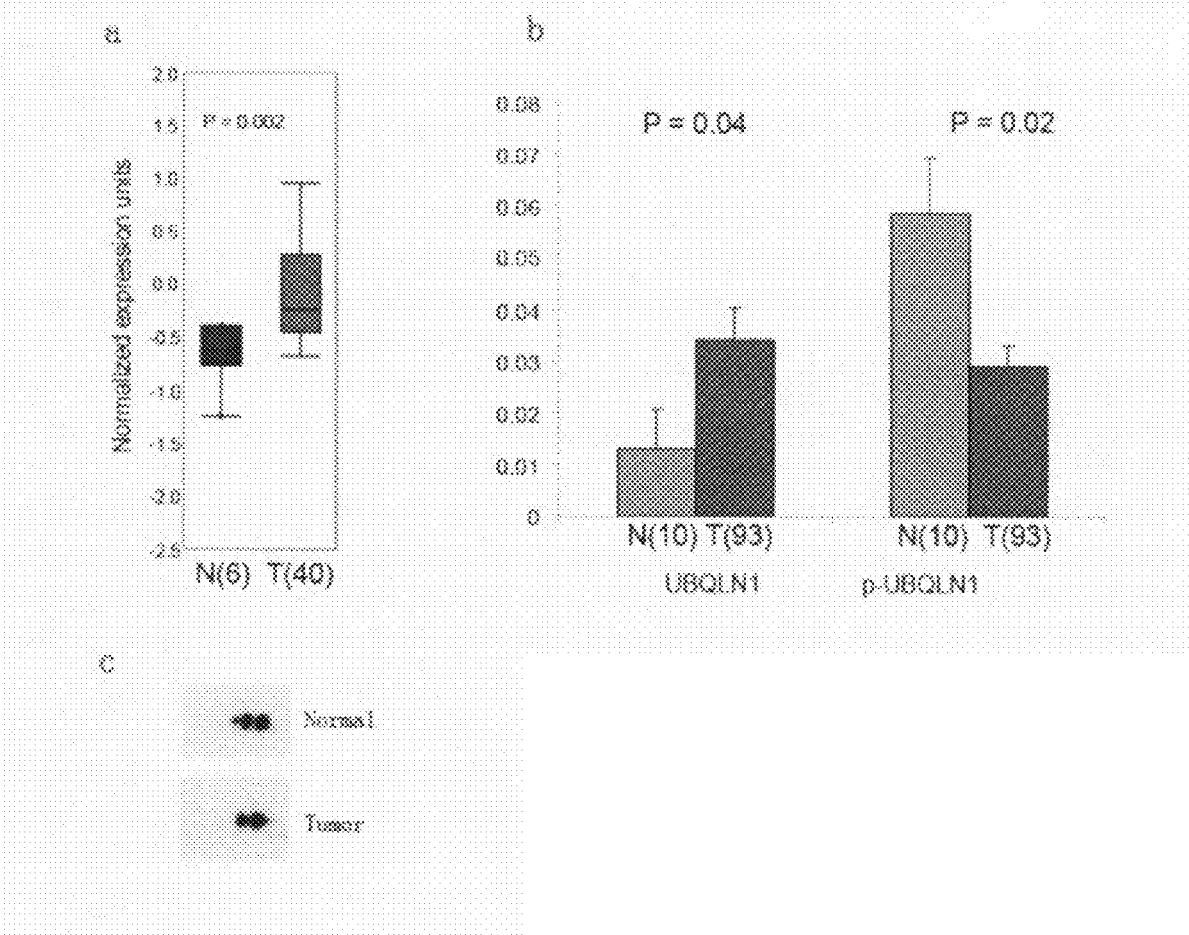
FIG. 16 shows characterization of UBQLN1.

A total of 9 clones with 2 different sizes (112 aa and 125aa) of UBQLN1 were found in this study. The mRNA was increased in lung adenocarcinomas (FIG. 16a). Two forms of protein were found by 2D Western blot, of which the native form was increased in tumors as compared to normal lung tissue and the phosphorylated form was decreased in tumors (FIGS. 16b and c). A second phosphorylated form of UBQLN1 was found in normal tissue only.

TABLE 5

Sequence Identity for phage clones associated with diagnosis and prognosis.

| Clone ID | Associated with Diagnosis | Associated with Prognosis | Translated Protein Sequences | SEQ ID NO | No. of Clones | Protein Identity |
|---|---|---|---|---|---|---|
| 12G5 | X | | PGLIPGFTPGLGALGST GGSSGTNGSNATPSEN TSPTAGTTEPGHQQFI QQMLQALAGVNPQLQ NPEVRFQQQLEQLSA MGFLNREANLQALIAT GGDINAAIERLLGSQPS | 1 | 7 | Ubiquilin 1 |
| 12G9 | X | | QIQQGLQTLATEAPGL IPGFTPGLGALGSTGGS SGTNGSNATPSENTSP TAGTTEPGHQQFIQQM LQALAGVNPQLQNPE VRFQQQLEQLSAMGF LNREANLQALIATGGD INAAIERLLGSQPS | 2 | 2 | Ubiquilin 1 |
| 7A2 | X | | NSLESYAFNMKATVE DEKLQGKINDEDKQKI LDKCNEIINWLDKNQT AEKEEFEHQQKELEKV CNPIITKLYQSAGGMP GGMPGGFPGGGAPPS GGASSGPTIEEVD | 3 | 2 | Heat shock 70kDa protein 8 (HSPA8) |
| 18D11 | X | | GAYPSTYDLDIEVHGG LQPCLELEYGAEPIVGI KGSLDSLASEEATMK VESWGSRKHEALYCIQ NTEI | 4 | 2 | hypothetical protein OB1516 |
| 4C10 | X | | QAFPQQTGRRATSEPT AM | 5 | 2 | PREDICTED: similar to Coagulation factor II receptor precursor |
| 2D5 | X | | VTRPPSGRRPPTS | 6 | 2 | PREDICTED: similar to B-cell receptor-associated protein 29 |
| 17H12 | X | | AVAQMRMRMKMRM RMGQEGTQQEPQQQN ILEDDTRDQGAHTGGP PGKPDADE | 7 | 2 | TPA: HDC18596 |
| 19G8 | X | | QERQTRAQKKGTSSSG HSTTKVIP | 8 | 2 | putative protein |
| 4C4 | X | | GTEIDGRSISLYYTGEK GQNQDYRGGKNSTWS GESKTLVLSNLSYSAT EETLQEVFEKATFIKVP QNQNGKSKGYAFIEFA SFEDAKEALNSCNKRE IEGRAIRLELQGPRGSP NARSQPSKTLFVKGLS EDTTEETLKESFDGSV RARIVTDRETGSSKGF GFVDFNSEEDAKAAK EAMEDGEIDGNKVTL DWAKPKGEGGFGGRG | 9 | 1 | Nucleolin (NCL protein) |

TABLE 5-continued

Sequence Identity for phage clones associated with diagnosis and prognosis.

| Clone ID | Associated with Diagnosis | Associated with Prognosis | Translated Protein Sequences | SEQ ID NO | No. of Clones | Protein Identity |
|---|---|---|---|---|---|---|
| | | | GGQACGRTRVTS | | | |
| 11G4 | X | | LGTAIGPVGPVTPIGPI GPIVPFTPIGPIGPIGPT GPAAPPGSTGSGGPTG PTVSSAAPSETTSPTSE SGPNQQFIQQMVQAL AGANAPQLPNPEVRFQ QQLEQLNAMGFLNRE ANLQALIATGGDINAA IERLLGSQPS | 10 | 1 | Ubiquilin 2 |
| 5B4 | X | | AERVSETWYMKGTVQ HCDFN | 11 | 1 | apolipoprotein B |
| 22A10 | X | | AKHSSAYTFFHPHSNP VSHYHPRFI | 12 | 1 | hypothetical protein UM00661.1 |
| 7D8 | X | | ARWGLRMG | 13 | 1 | acetyl-CoA acetyltransferase |
| 7G8 | X | | CCLPRFTESTSV | 14 | 1 | similar to ENSANGP000000 05259 |
| 8D5 | X | | GELKGKEK | 15 | 1 | adenine phosphoribosyltran sferase 1, APRT |
| 13D2 | X | | GKVGGGFLI | 16 | 1 | COG0730: Predicted permeases |
| 22F5 | X | | GPQTDRPPQDRRPRHA PCPQEGCVPLESNAGR PHNLLSDYSCDKSPGR SMTRG | 17 | 1 | hypothetical protein MCA0617 |
| 17D3 | X | | GSRGQEFKTSLANMV KLHLY | 18 | 1 | PRO0478 |
| 1H8 | X | | HLHNPGDPCRVMSQR PL | 19 | 1 | PREDICTED: similar to VPS10 domain receptor protein SORCS 3 |
| 18A7 | X | | HPWAPKGWARWGAA PWAAGWPGTPALSAG TPKLAAALE | 20 | 1 | PREDICTED: similar to Zinc finger protein 43 |
| 22C1 | X | | IISRRGTNTAPLTSSSA TTRTPARLWCCRS | 21 | 1 | hypothetical protein FG05539.1 |
| 1E8 | X | | IKTKENMLREARQKG LVTNGSPSD | 22 | 1 | hypothetical protein |
| 6B5 | X | | IRIAPLEVKFLDRRKTD QSESICQECFH | 23 | 1 | solute carrier family 9, member 4 |
| 4D1 | X | | KKKDNL | 24 | 1 | COG0628: Predicted permease |
| 4E8 | X | | KKTSGPDGFTGERYQ XI | 25 | 1 | ORF2 contains a reverse transcriptase domain |
| 2B6 | X | | KYWRSIEDRKI | 26 | 1 | cytochrome D ubiquinol oxidase subunit II |

TABLE 5-continued

Sequence Identity for phage clones associated with diagnosis and prognosis.

| Clone ID | Associated with Diagnosis | Associated with Prognosis | Translated Protein Sequences | SEQ ID NO | No. of Clones | Protein Identity |
|---|---|---|---|---|---|---|
| 2G4 | X | | LELQRQSSL | 27 | 1 | spalt4 |
| 13F6 | X | | LEPSFSANYHKDKKTPHVLTHRWELNNENTWTQEEEQHTLGPVL | 28 | 1 | PREDICTED: similar to glycogenin 2 |
| 13F9 | X | | LIFRGNGQGMREGNKK | 29 | 1 | hypothetical protein AN5619.2 |
| 1B8 | X | | LLLKLEPISQQ | 30 | 1 | glycosyl transferase, group 2 family protein |
| 1F4 | X | | LRQEDCLNIPGGRGCSEPRSCHCTPAWATE | 31 | 1 | KIAA1556 protein |
| 7E6 | X | | LRSHAWWWT | 32 | 1 | trbI |
| 10G2 | X | | LSISCL | 33 | 1 | hypothetical protein FG08221.1 |
| 2C6 | X | | MVLVNLKP | 34 | 1 | heparan Sulfate-glucuronic acid-5-Epimerase (hse-5) |
| 7F9 | X | | NKTPSVPHNHFSLIK | 35 | 1 | PREDICTED: similar to zinc finger protein 300 |
| 8B6 | X | | NSCILKEDKDILKKPLNSRFSSNSKVKNMRLLEHSTFSAPLNRVM | 36 | 1 | asparagine-rich protein, putative |
| 7E10 | X | | NSDFYDFFHK | 37 | 1 | Hypothetical protein CBG01255 |
| 2D10 | X | | NSEGRLLS | 38 | 1 | Hypothetical protein ZC443.6 |
| 2F9 | X | | NSFDLVGTGGLEESRLSIPWPLGSLLYAKSPRK | 39 | 1 | TPA: olfactory receptor OR11-50 |
| 3C5 | X | | NSKESI | 40 | 1 | ATP-dependent helicase |
| 3D1 | X | | NSKNTVLQLDSVRSMSESRAITT | 41 | 1 | immunoglobulin heavy chain variable region |
| 2B9 | X | | NSLPGLPSLYFVSMAKHKNNTSTTIS | 42 | 1 | GH05757p |
| 7B7 | X | | NSPNTLFRSASTKPK | 43 | 1 | genral secretion protein E |
| 2C5 | X | | NSQECLSQILLIPSSCLKKNICV | 44 | 1 | ENSANGP00000011065 |
| 7E11 | X | | NSRLRGIL | 45 | 1 | COG0330: Membrane protease subunits, stomatin/prohibitin homologs |
| 4B6 | X | | NSVFLPFINMFIRKWYHSEHISYILFFFCVWIFTLR | 46 | 1 | sensor-histidine kinase VanSc |
| 11D1 | X | | NVTRVFK | 47 | 1 | hypothetical protein |

TABLE 5-continued

Sequence Identity for phage clones associated with diagnosis and prognosis.

| Clone ID | Associated with Diagnosis | Associated with Prognosis | Translated Protein Sequences | SEQ ID NO | No. of Clones | Protein Identity |
|---|---|---|---|---|---|---|
| 7A10 | X | | PASTLKGQDARNRLTQK | 48 | 1 | similar to AF15q14 protein isoform 2 |
| 1B12 | X | | PIHMCYTGAKKEGCFVGKSS-EEVPRTWLLSLKGDGVNSPCWGSY | 49 putative | 1 | CIR protein, |
| 13D1 | X | | PQIASHSLFLLPRVLSTSIIS | 50 | 1 | hypothetical protein GZ28G717 |
| 5A4 | X | | PQMTKTKRTHKNI | 51 | 1 | FP588 |
| 17A5 | X | | QAYVNV | 52 | 1 | COG1538: Outer membrane protein |
| 8B3 | X | | QEASVSGLKMKSMSTKQVWNQIAFDEKGSGFWRLYFRCCYNASSNQD | 53 | 1 | S2 gene product |
| 6A6 | X | | QTCKQLQFLPFAS | 54 | 1 | PREDICTED: hypothetical protein XP537924 |
| 7B10 | X | | RMTYLWGLNHKPTDNVNCHSQFLP | 55 | 1 | putative permease (MFS superfamily) |
| 5D5 | X | | RSQFQQGNVPVQSRLR | 56 | 1 | hypothetical protein having cryptosporidium-specific paralog |
| 2B3 | X | | RVTPTAEQSPIPGCRK | 57 | 1 | TonB-dependent receptor |
| 1A8 | X | | VCSSSIHRSPQVERVSPPHHFPEEQT | 58 | 1 | PMF31 |
| 3D5 | X | | VESASLHLDCF | 59 | 1 | hypothetical protein BH11560 |
| 3B7 | X | | VGGGRASGRIANGCWA | 60 | 1 | AMPA GLutamate Receptor subunit (glr-2) |
| 1A10 | X | | VPIQMPPEATCVT | 61 | 1 | hypothetical protein Bcep02003282 |
| 6D2 | X | | VSNSMKI | 62 | 1 | ORFveg109 |
| 1F6 | X | | VVSGSGHLERSQDCGEKGNIFQ | 63 | 1 | likely glycerol-3-phosphate dehydrogenase |
| 20A12 | X | | AHSPTKGCQICQDQEK | 64 | 1 | putative retroelement pol polyprotein |
| 20D12 | X | | AHSRRKTAGN | 65 | 1 | recombination activating gene 2 |
| 6G7 | X | | EHIPAPASPRFSIQGS | 66 | 1 | PREDICTED: similar to Hypothetical protein 4832420M10, partial |
| 10D10 | X | | GNRDPVAC | 67 | 1 | TPA:52K |

TABLE 5-continued

Sequence Identity for phage clones associated with diagnosis and prognosis.

| Clone ID | Associated with Diagnosis | Associated with Prognosis | Translated Protein Sequences | SEQ ID NO | No. of Clones | Protein Identity |
|---|---|---|---|---|---|---|
| 17H8 | X | | GPWHQMPSPTKGWLGRISQ | 68 | 1 | flagellum-specific ATP synthase FliI |
| 15B6 | X | | IAHSGSSVF | 69 | 1 | Niemann-Pick disease, type C1 |
| 15A12 | X | | IQCVYKPNSHFV | 70 | 1 | Similar to RIKEN cDNA 4930429O20 |
| 19B12 | X | | IYISLNVVTLKACTLKFGCINATFNLN | 71 | 1 | ENSANGP000000 25688 |
| 23E12 | X | | LFYGGMGGWKNGSRASEAD | 72 | 1 | NIb protein |
| 15E9 | X | | LLQRNTVPQKQRNKAGWRMTLTS | 73 | 1 | PREDICTED: similar to ankyrin repeat-containing SOCS box protein 5 |
| 16H8 | X | | LPSVARRSPGLGPQLRQQGGCGPVCHHQDIPPPQGLPFPLAPSPFL | 74 | 1 | parathymosin-like |
| 8B12 | X | | NSALGNHGEGKPIVECLLRC | 75 | 1 | two-component system, sensor protein |
| 6H3 | X | | NSASSKCPSY | 76 | 1 | hypothetical protein PMM1351 |
| 21G10 | X | | NSFKAIRK | 77 | 1 | CDC27D-618 protein |
| 17H10 | X | | NSFLEGEEQIL | 78 | 1 | hypothetical protein LIC11950 |
| 14E12 | X | | NSSVTLMRQRVTMMGRHTT | 79 | 1 | DNA topoisomerase II |
| 21C12 | X | | PDWDAVVQSWLTAASNS | 80 | 1 | ADAM 32 precursor (A disintegrin and metalloprotease domain 32) variant |
| 16C7 | X | | PRRTGEGAPPARLARRAGEVEHERTC | 81 | 1 | PREDICTED: similar to testin |
| 17G10 | X | | SKLSKGYEKLVF | 82 | 1 | putative transcriptional regulator |
| 16E8 | X | | TMPKGNVKLGN | 83 | 1 | mitogen-activated protein kinase kinase kinase 3 isoform 2 |
| 8F11 | X | | VITLIYR | 84 | 1 | hypothetical protein OB0069 |
| 16H11 | X | X | GPEGSEAVQSGTPEEPEPELEAEASKEAEPEPEPEPELEPEAEAEPEPELEPEPDPEPEPDFEERDESEGIPEGQSSDRRCPAHAG | 85 | 3 | nucleolar protein 3 (apoptosis repressor with CARD domain) |

TABLE 5-continued

Sequence Identity for phage clones associated with diagnosis and prognosis.

| Clone ID | Associated with Diagnosis | Associated with Prognosis | Translated Protein Sequences | SEQ ID NO | No. of Clones | Protein Identity |
|---|---|---|---|---|---|---|
| 16E9 | X | X | PQCREKTKFN | 86 | 1 | tripartite motif-containing 7 isoform 4 |
| 16B11 | | X | SGMPRRYSDYPDAYTT | 87 | 1 | cytochrome c oxidase subunit I |
| 16E11 | | X | DVRVSIHKHILG | 88 | 1 | nucleolar protein 3 (apoptosis repressor with CARD domain) |
| 8E11 | | X | GKRRDSFFSF | 89 | 1 | hypothetical protein AM638 |
| 14E11 | | X | LETIILSKLAQEQKTKHRMFSLISGS | 90 | 1 | putative p150 |
| 16G11 | | X | NSPSVGLFTH | 91 | 1 | MUP1 |
| 10G9 | | X | NSRLYQKYKN | 92 | 1 | similar to CG9996-PA |
| 5E3 | | X | PARLARRAGEVEHERTC | 93 | 1 | hypothetical protein Magn028940 |
| 16F11 | | X | SLTSTASDGDYSARTVM | 94 | 1 | COG0568:DNA-directed RNA polymerase, sigma subunit |
| 10G11 | | X | TQSPTTLNVAGTPQQ | 95 | 1 | IgG kappa light chain variable region |
| 21C5 | | | PSQLKCSPSANVKMGGGKGLKIRENCMHLRT | 96 | 14 | glycine decarboxylase |
| 13E11 | | | GERGKRTFQKESDTALILRECPICL | 97 | 11 | BRCA1 protein |
| 11A12 | | | NSLEWTKVYLGKKIWTPEKGNSSYK | 98 | 7 | FAM53B protein |
| 13B3 | | | RPQTDRPPQDRRPRHAPCPQEGCVPLESNAGRPHNLLSDYSCDKSPGRSMTRG | 99 | 5 | PSIP1 protein |
| 19H9 | | | GQQRKPCLGGKKKT | 100 | 3 | CGI-143 protein |
| 22A9 | | | NSTATTSSSSLKDPGSRRPSWTSLAKERSQEQAKRNLEFQSPTLSPPMKATLSKPS | 101 | 3 | Oncogene EMS1 |
| 16B9 | | | PCSKH | 102 | 3 | Siah2 protein |
| 15D6 | | | QERPSETIDRERKRLVETLQADSG...EPDFEERDESEDS | 103 | 3 | nucleolar protein 3 |
| 13C8 | | | RICPTHTKPQNTVPLHLLRPTIDQL | 104 | 3 | FAT tumor suppressor 2 precursor |
| 12E5 | | | WVSEPHCVVVNM | 105 | 3 | Kinesin-like protein KIF13B |

TABLE 5-continued

Sequence Identity for phage clones associated with diagnosis and prognosis.

| Clone ID | Associated with Diagnosis | Prognosis | Translated Protein Sequences | SEQ ID NO | No. of Clones | Protein Identity |
|---|---|---|---|---|---|---|
| 15E3 | | | GAGTGARARARAGAALTWS | 106 | 2 | ALEX2 protein |
| 17A7 | | | ILLMRRRMTRMSGGAEQTQTMQMGVKTK | 107 | 2 | CREB-binding protein |
| 17B10 | | | LHHIGQQHPQRFWHQRPIS | 108 | 2 | telomerase catalytic subunit |
| 18H6 | | | LMRVLKTEVTGYQEVCTPKRNWNSRQE | 109 | 2 | EF hand domain family, member A1 |
| 13E12 | | | NSLIQHQHLGQI | 110 | 2 | ZFP-95 |
| 19G6 | | | NSQGLDFSKATLRSRQRL | 111 | 2 | TIP30 |
| 18F11 | | | NSSDSLRIVWLLSDVYESFLHLPFQISHCSWYKYLS | 112 | 2 | CCAAT/enhancer binding protein alpha |
| 14H12 | | | NSSPADLPCRIC | 113 | 2 | UbcH 7-binding protein |
| 21E12 | | | RTPSSPCWPPGPVLAE...EPEPDFEERDESEDS | 114 | 2 | nucleolar protein 3 (apoptosis repressor with CARD domain) |
| 13A6 | | | RVPKQRYRSMEQNRALRNNAVYLQLSDL | 115 | 2 | tumor-related protein DRC2 |
| 10G3 | | | STKKMGTQALSKAAPHG | 116 | 2 | kringle-containing protein |
| 15B12 | | | TRSGSSSWAVLTGARPKRLCAATFPNMEKS | 117 | 2 | HSPC017 |
| 8G11 | | | AEEYRLQRHYCSY | 118 | 1 | Pleckstrin and Sec7 domain containing 2 |
| 23D12 | | | AESTPVQDPSIFCEYSTPTSMGGGK | 119 | 1 | Chain B, Binary Complex Structure Of Human Tau Protein Kinase I |
| 11A2 | | | AEVPILFIPP | 120 | 1 | solute carrier family 4 sodium bicarbonate cotransporter-like member 10 |
| 17A1 | | | AGGSFSPWPVLLPPPPPGGKSGHNRGQRPH | 121 | 1 | frizzled 8 |
| 10D4 | | | AHIRTKDSINCI | 122 | 1 | TRIM14 isoform alpha |
| 6F3 | | | AICSIL | 123 | 1 | |
| 10E5 | | | AIGKIAKNNP | 124 | 1 | SFRS protein kinase 2 |
| 16E4 | | | ANNLLNGGLYTGKPYCGN | 125 | 1 | RAD51D |
| 10C11 | | | ANQLNELNPK | 126 | 1 | |
| 9G11 | | | AQGPRCAGCTGKGRTTAG | 127 | 1 | |

TABLE 5-continued

Sequence Identity for phage clones associated with diagnosis and prognosis.

| Clone ID | Associated with Diagnosis | Prognosis | Translated Protein Sequences | SEQ ID NO | No. of Clones | Protein Identity |
|---|---|---|---|---|---|---|
| 6D4 | | | AQVLCHIEDQVPDQIL PGVPLELLGEFCQESG RRK | 128 | 1 | |
| 12B5 | | | ARGPSWRSNELWLHH LSSSSRHLMSS | 129 | 1 | |
| 1A11 | | | ASCYLTSNCTTRVQ | 130 | 1 | |
| 1F11 | | | ASRKIWYELNSGYAE WRTEEAIRRSGRHQV Q | 131 | 1 | |
| 1E7 | | | ATLSV | 132 | 1 | |
| 4E5 | | | AVYFFKAK | 133 | 1 | |
| 13H8 | | | AWYKICKICL | 134 | 1 | |
| 14B9 | | | AYNKFLHL | 135 | 1 | |
| 21A12 | | | CWPGWSQTPDLR | 136 | 1 | |
| 7H8 | | | DEWKNTFQGELKGLK C | 137 | 1 | |
| 14A5 | | | DKKFLIETSI | 138 | 1 | |
| 7G7 | | | DVFNTVGPLGWSVFH PQTNADQNGVF | 139 | 1 | |
| 1G7 | | | ECQGQC | 140 | 1 | |
| 6G6 | | | EEEHSDKYVLSLLMNS LSLRS | 141 | 1 | |
| 6G2 | | | EFFLMTIGKN | 142 | 1 | |
| 17G8 | | | EKEKNLNCFFGRTTTK KR | 143 | 1 | |
| 7A5 | | | EKLATSMYLQNPNWR LSSESEVSME | 144 | 1 | |
| 9F11 | | | ELESCCVTQAGVPCYD LCSLQPPSPGFK | 145 | 1 | |
| 12H4 | | | ELLFL | 146 | 1 | |
| 21B8 | | | EMLNGGRVLWM | 147 | 1 | |
| 12B3 | | | EQLQT | 148 | 1 | |
| 4F10 | | | ERKVF | 149 | 1 | |
| 8B1 | | | ETSIKYT | 150 | 1 | |
| 17G12 | | | GAGKFLREKEKEISLG LMLGK | 151 | 1 | |
| 8E5 | | | GCLG | 152 | 1 | |
| 1F7 | | | GCLGFWGRG | 153 | 1 | |
| 15C3 | | | GEACLSTATSW | 154 | 1 | |
| 6C12 | | | GFLTMERKKITPPTTK TYISTLPTDSIKQLRNG DYKATS | 155 | 1 | |

TABLE 5-continued

Sequence Identity for phage clones associated with diagnosis and prognosis.

| Clone ID | Associated with Diagnosis | Prognosis | Translated Protein Sequences | SEQ ID NO | No. of Clones | Protein Identity |
|---|---|---|---|---|---|---|
| 7C9 | | | GGCDHCRDTTHGGCG HCGLRGNPSRPPDLQD CLC | 156 | 1 | |
| 3A6 | | | GIFFVSKI | 157 | 1 | |
| 3A1 | | | GIGNVKDGRHGESF | 158 | 1 | |
| 14A11 | | | GISPTKEDVIHSDVQD ELVHSACYVCI | 159 | 1 | |
| 23F5 | | | GKHEGEG | 160 | 1 | |
| 3C10 | | | GKIDERGRQGGRERD RNRDRERQRERE | 161 | 1 | |
| 17B6 | | | GKPKRHWDERAAGGL | 162 | 1 | |
| 1A1 | | | GKPTPLIQ | 163 | 1 | |
| 9F9 | | | GKVKELNKEVREKKG KIKQYNTXQKGKKSR RQCKNS | 164 | 1 | |
| 7E7 | | | GLPLWRRERVKVMR | 165 | 1 | |
| 5G11 | | | GLWWKRKYLHLNTRE KHSQKLLCDDCIHLTE LNIPIDRAVWKHSCCG MCKWRFGAL | 166 | 1 | |
| 24D5 | | | GMST | 167 | 1 | |
| 21D2 | | | GNYAK | 168 | 1 | |
| 21D12 | | | GNYARQ | 169 | 1 | |
| 11H11 | | | GPAFVLMKPGASPYPI LALTLITNQMLQNKSN NDPN | 170 | 1 | |
| 1F9 | | | GPFCHQRSGNPRIHHQ HSQAHPWSGLQEACT SGTQRDSEICHEGDGN SRCAH | 171 | 1 | |
| 8G5 | | | GPTSN | 172 | 1 | |
| 21H11 | | | GQHYPNTKARQKITTR KL | 173 | 1 | |
| 10F2 | | | GQRLIIING | 174 | 1 | |
| 1G3 | | | GRCVVATEINSRNRDS ACQEFEFRV | 175 | 1 | |
| 13G1 | | | GRGRTRWGMGMLLK KIQ | 176 | 1 | |
| 3E1 | | | GRPGIGATHSSRFIPLK | 177 | 1 | |
| 19F5 | | | GRVPFTFFNLSL | 178 | 1 | |
| 2B10 | | | GTSSSHDPLSRLPKLN LSRGGVWASWVK | 179 | 1 | |
| 3H10 | | | GVERVAYSIHPASPTS VSHSLVERMAMAPPV MESMRSPPQSTRPRVP LS | 180 | 1 | |

TABLE 5-continued

Sequence Identity for phage clones associated with diagnosis and prognosis.

| Clone ID | Associated with Diagnosis | Prognosis | Translated Protein Sequences | SEQ ID NO | No. of Clones | Protein Identity |
|---|---|---|---|---|---|---|
| 17B12 | | | GWGRRIA | 181 | 1 | |
| 6D6 | | | HCHCLPDLP | 182 | 1 | |
| 3G10 | | | HILSSTCCFLTF | 183 | 1 | |
| 7D6 | | | HLWAQHHSVSSLKGRTTLEYF | 184 | 1 | |
| 17B4 | | | HTFKNTWELKNENTWTQGGEYHTPGPAGGFGGKGRESIRTKI | 185 | 1 | |
| 8F4 | | | IASYM | 186 | 1 | |
| 16G2 | | | IDLKSNL | 187 | 1 | |
| 12G12 | | | IFRN | 188 | 1 | |
| 4F5 | | | IGTRDQGKRLRMK | 189 | 1 | |
| 7G1 | | | ILLQGYPGSSSTSLRPHSSN | 190 | 1 | |
| 16E3 | | | INQKYTWLDKSHYALTTNASS | 191 | 1 | |
| 4F11 | | | IQNSKKS | 192 | 1 | |
| 17C8 | | | IQSATELVGRLGMHPRIQSATELVVS | 193 | 1 | |
| 14B10 | | | IRASNQYRSSVKYISVH | 194 | 1 | |
| 6A3 | | | ITPRAVFWY | 195 | 1 | |
| 20D10 | | | IYFKKKT | 196 | 1 | |
| 7H2 | | | KDHAQSNKYLTSL | 197 | 1 | |
| 4E9 | | | KGMNKTSKNCGTM | 198 | 1 | |
| 15G5 | | | KGTTRSGSLGCK | 199 | 1 | |
| 2G11 | | | KIYNI | 200 | 1 | |
| 4D5 | | | KKAERSTK | 201 | 1 | |
| 1C8 | | | KKEESSSRMWPL | 202 | 1 | |
| 22C12 | | | KKHFICTSFLDLGYTVPVY | 203 | 1 | |
| 12D2 | | | KSFCRIFLCW | 204 | 1 | |
| 20B6 | | | KSTAHSLCKGLM | 205 | 1 | |
| 11H2 | | | KTTIF | 206 | 1 | |
| 21E6 | | | LAYVSNSHQGKFGWLSGLSR | 207 | 1 | |
| 7G11 | | | LDGMLAAQTEEDPET | 208 | 1 | |
| 15F4 | | | LETEAGESLEPRRWRLQ | 209 | 1 | |
| 22D3 | | | LEVRISRPSWLTR | 210 | 1 | |
| 13A12 | | | LHKPQSQWTR | 211 | 1 | |

TABLE 5-continued

Sequence Identity for phage clones associated with diagnosis and prognosis.

| Clone ID | Associated with Diagnosis Prognosis | Translated Protein Sequences | SEQ ID NO | No. of Clones | Protein Identity |
|---|---|---|---|---|---|
| 4A9 | | LHQNPKGLGSESFWIT LPGR | 212 | 1 | |
| 20C1 | | LKDVTVSVRLAPLYIS M | 213 | 1 | |
| 14F2 | | LKHENCLNPGGRGCSE SRWCRCTPTRTTE | 214 | 1 | |
| 10A9 | | LKQILSSVLNSEIELLL | 215 | 1 | |
| 9H8 | | LLHMAAARRSAEQRG KSPS | 216 | 1 | |
| 7C2 | | LLPQPPE | 217 | 1 | |
| 16G1 | | LLSHLQDWQHH | 218 | 1 | |
| 12G1 | | LLSKSLRNEDTAVV | 219 | 1 | |
| 7B8 | | LQTGKEKASHPPPTLF SPIIYNNTDLRAVKVIL KYYIKWVRRE | 220 | 1 | |
| 14G11 | | LQVTLPRRGRDTCGSH REATER | 221 | 1 | |
| 16G12 | | LRIT | 222 | 1 | |
| 23B7 | | LRLSTPWPTLKPHLKG KVMSL | 223 | 1 | |
| 16C10 | | LSESIWFAFHFDDCK | 224 | 1 | |
| 15F5 | | LSHGTG | 225 | 1 | |
| 1C11 | | LTRNDI | 226 | 1 | |
| 11B9 | | MKEYA | 227 | 1 | |
| 11D12 | | NELWLHHLSSSSRHL MSS | 228 | 1 | |
| 10C12 | | NGCVYLSKFKL | 229 | 1 | TBC1 domain family, member 2 |
| 17A3 | | NKEREVFSTNGTGYPH GKKRTTQ | 230 | 1 | |
| 15D12 | | NNQK | 231 | 1 | |
| 1E4 | | NRGKHRG | 232 | 1 | |
| 4A5 | | NSACL | 233 | 1 | |
| 1C12 | | NSAQN | 234 | 1 | |
| 8D1 | | NSASTEPSTNRLQLPW VGGLMQTGRLPGSLT A | 235 | 1 | |
| 18D4 | | NSASTRPISHIRRRTLL SSA | 236 | 1 | |
| 11B10 | | NSDLVRHQFKGKTTL KVH | 237 | 1 | |
| 5D4 | | NSDQIQNTGAESREKV RMSITADEFVG | 238 | 1 | |
| 3E4 | | NSDVI | 239 | 1 | |

TABLE 5-continued

Sequence Identity for phage clones associated with diagnosis and prognosis.

| Clone ID | Associated with Diagnosis Prognosis | Translated Protein Sequences | SEQ ID NO | No. of Clones | Protein Identity |
|---|---|---|---|---|---|
| 3B8 | | NSECTCIIVKGNTFSPCKFIV | 240 | 1 | |
| 4D2 | | NSEG | 241 | 1 | |
| 13H12 | | NSEGAT | 242 | 1 | |
| 2A7 | | NSEQQRLKELKSEHTNNKKVKQPCC | 243 | 1 | |
| 15D1 | | NSESNSFASKNK2N | 244 | 1 | |
| 21B1 | | NSFCVCVFNSQS | 245 | 1 | |
| 8C2 | | NSFGFST | 246 | 1 | |
| 18C9 | | NSFLLEIQEPSLGVWIRTPFL | 247 | 1 | |
| 10E11 | | NSFLSF | 248 | 1 | |
| 11F3 | | NSFPSSICFNS | 249 | 1 | |
| 1E10 | | NSFQGLQDYLIKSSMNLVL | 250 | 1 | TRHDE |
| 15F11 | | NSFRKQRHWKG | 251 | 1 | |
| 6C6 | | NSFRL | 252 | 1 | |
| 20E10 | | NSFRPHRFKSNA | 253 | 1 | |
| 7C12 | | NSFRYFA | 254 | 1 | |
| 11E7 | | NSGVSW | 255 | 1 | |
| 9E3 | | NSHCDI | 256 | 1 | |
| 4C9 | | NSHNPKLEK | 257 | 1 | |
| 7A3 | | NSIHHVLLSLHPPLYK | 258 | 1 | |
| 3A2 | | NSIHM | 259 | 1 | |
| 22C3 | | NSIIPRAIWLSVERMWQLRW | 260 | 1 | |
| 2A6 | | NSIKCKKM | 261 | 1 | |
| 12H7 | | NSIKRFSASCVARICPG | 262 | 1 | |
| 18D6 | | NSIL | 263 | 1 | |
| 17E4 | | NSILIKYGDTWN | 264 | 1 | |
| 1G10 | | NSILQSAGESFLLHNLNLCS | 265 | 1 | |
| 2G3 | | NSITHLEKHTILYTNSSTK | 266 | 1 | |
| 3A4 | | NSKETSSNGTEWNPH | 267 | 1 | |
| 17B5 | | NSKGRRV | 268 | 1 | |
| 9E4 | | NSKHR | 269 | 1 | |
| 21H6 | | NSKIMFSKMFLSQITE | 270 | 1 | |
| 19H5 | | NSKQRFFLKKK | 271 | 1 | |
| 17C5 | | NSLCGICI | 272 | 1 | |

TABLE 5-continued

Sequence Identity for phage clones associated with diagnosis and prognosis.

| Clone ID | Associated with Diagnosis | Prognosis | Translated Protein Sequences | SEQ ID NO | No. of Clones | Protein Identity |
|---|---|---|---|---|---|---|
| 7C11 | | | NSLKKL | 273 | 1 | |
| 19H7 | | | NSLLCLICLT | 274 | 1 | |
| 10B2 | | | NSLNKIQNTFESSTID | 275 | 1 | |
| 21B4 | | | NSLPLT | 276 | 1 | |
| 10B10 | | | NSLPWKQKV | 277 | 1 | Chain A, Structurally Distinct Recognition Motifs In Lymphotoxin-B Receptor And Cd40 For Traf-Mediated Signaling |
| 12D7 | | | NSLS | 278 | 1 | |
| 11H12 | | | NSLSFADWFWKRS | 279 | 1 | |
| 5H5 | | | NSLSSFHCSSHCF | 280 | 1 | |
| 8B2 | | | NSMMDHVTNNATGMNIMEK | 281 | 1 | |
| 4G1 | | | NSMSMPRLCGRMKECVPATNAPTSTS | 282 | 1 | |
| 13C9 | | | NSMVVTATSYSTPIPEDRLSTRGKEQMPHEMS | 283 | 1 | |
| 7E5 | | | NSNEE | 284 | 1 | |
| 22E11 | | | NSNPYPGGRSTSGDPKFKPRNCSVPQWLGYNPFWP | 285 | 1 | |
| 4F2 | | | NSPAGISRELVDKLAAALE | 286 | 1 | |
| 1C6 | | | NSPASAS | 287 | 1 | |
| 10B1 | | | NSPKMGSPSLLKYYT | 288 | 1 | |
| 9D1 | | | NSPKMGSPSLLKYYT-RS | 289 | 1 | |
| 6A2 | | | NSPPAN | 290 | 1 | |
| 3D4 | | | NSPSQPACLGAQR | 291 | 1 | |
| 5F1 | | | NSPVPSVTTDYQNISLLT | 292 | 1 | |
| 10H10 | | | NSQAVCIFF | 293 | 1 | |
| 21H10 | | | NSQNVFNSSSFHFMALERYRRK | 294 | 1 | |
| 1H5 | | | NSQRLIWLSN | 295 | 1 | |
| 14H6 | | | NSQVGLSSSYPQ | 296 | 1 | |
| 3D3 | | | NSRCHCPA | 297 | 1 | |
| 8A1 | | | NSRFDF | 298 | 1 | |
| 11D4 | | | NSSDITLIEKKELIKANI | 299 | 1 | TAK1-like protein |

TABLE 5-continued

Sequence Identity for phage clones associated with diagnosis and prognosis.

| Clone ID | Associated with Diagnosis | Prognosis | Translated Protein Sequences | SEQ ID NO | No. of Clones | Protein Identity |
|---|---|---|---|---|---|---|
| 2D11 | | | NSSFLMT | 300 | 1 | |
| 4E11 | | | NSSFLQGALVPLSGE | 301 | 1 | |
| 17D6 | | | NSSGLLKVSLLKYHPSFMNSRGFSLQVL | 302 | 1 | |
| 16G8 | | | NSSRQPHPLLTSLNILYI | 303 | 1 | |
| 3B10 | | | NSSRTAFSFHSLLLL | 304 | 1 | |
| 10G5 | | | NSSSSQHREHEKEEKY | 305 | 1 | HGDF-related pro 2 |
| 4D7 | | | NSSSSSNPILSHGTTKNKVCSAPEALYAGDGQLNENLKGKPSGLRCVPLRDFT | 306 | 1 | 2 |
| 17A9 | | | NSSSYRPQRVWCGSICSRASTGIPIPQGLPPKYLAFKELSYLNSAGTSC | 307 | 1 | |
| 7F8 | | | NSSV | 1 | | |
| 18C5 | | | NSSVTLMRQRVMMMGRHTT | 308 | 1 | dipeptide ABC transporter, dipeptide-binding protein |
| 11H8 | | | NSSWHIRSQGEDNRETALVYRKQIFSETLHYYKKKK | 309 | 1 | |
| 20E7 | | | NSTDK | 310 | 1 | |
| 16B6 | | | NSTGNMKGIHLTFQLKRMGKPTPLLF | 311 | 1 | |
| 1D4 | | | NSTR | 312 | 1 | |
| 19A2 | | | NSTSKSVEHS | 313 | 1 | |
| 9A3 | | | NSTVLKYVTLPHLRE | 314 | 1 | |
| 5F2 | | | NSVCV | 315 | 1 | |
| 10C6 | | | NSVIIESLVVNV | 316 | 1 | |
| 1C7 | | | NSVNFILIPLDLEG | 317 | 1 | |
| 12C8 | | | NSVQGRAVLLCHGLTGRAWFYLYGLFCV | 318 | 1 | |
| 6C2 | | | NSVVH | 319 | 1 | |
| 4E4 | | | NSVYMI | 320 | 1 | |
| 3F3 | | | NSYCVNQAGLELLASSDPLALASGMLGL | 321 | 1 | |
| 1H4 | | | NSYLFSR | 322 | 1 | |
| 1D12 | | | PAWATKSKTPS | 323 | 1 | |
| 13H6 | | | PGLGEWCRVCV | 324 | 1 | |
| 6B10 | | | PGRHLAEAQHGHPRPCLHSEVFS | 325 | 1 | |

TABLE 5-continued

Sequence Identity for phage clones associated with diagnosis and prognosis.

| Clone ID | Associated with Diagnosis | Prognosis | Translated Protein Sequences | SEQ ID NO | No. of Clones | Protein Identity |
|---|---|---|---|---|---|---|
| 3E6 | | | PHATSHLRVKHEISQIQHPPLLS | 326 | 1 | |
| 14F11 | | | PISLRGATAGRAERIREEEVRGAVHHKRH | 327 | 1 | |
| 7B1 | | | PQRTTLNFLLGQPARLPLGLSVGDRPTSQGR | 328 | 1 | |
| 1B9 | | | PRFPSSAQQRMK | 329 | 1 | |
| 5E11 | | | PSRPPRRGGGARAHVLGPERW | 330 | 1 | |
| 1A9 | | | QGHTGVSHK | 331 | 1 | |
| 1B7 | | | QKTKHRIFSLIGGN | 332 | 1 | |
| 2A2 | | | QMLLLPAI | 333 | 1 | |
| 3E12 | | | QRSRVAEGWRGPLNPELTPKCIDPSMHGWR | 334 | 1 | |
| 20F1 | | | QSLPPARNCNKLPDSML | 335 | 1 | |
| 1E9 | | | QVPRVLPQHRLGLAGEEAGAPSIPATDHRRLRSGQL | 336 | 1 | GADD45 gamma |
| 2E2 | | | QVSGPPSKI | 337 | 1 | |
| 2H3 | | | QWLTPVIPTLWEAKAGG | 338 | 1 | breast cancer suppressor element Ishmael Upper RP2 |
| 2B4 | | | RALQQLRHPDLHLQRRSQAQQHQGGQDS | 339 | 1 | |
| 14E10 | | | RAVRREASHRLPSPPLASRRPLDALS | 340 | 1 | |
| 4D8 | | | RDDSDYSVE | 341 | 1 | |
| 18F10 | | | RECTRCRRKTESTAQRVKKPATLLASVKPPANAVSTM | 342 | 1 | |
| 1B5 | | | RGPKRLL | 343 | 1 | |
| 20G3 | | | RISILKR | 344 | 1 | |
| 18E11 | | | RIVRVTPRRSWNHYETIESKE | 345 | 1 | |
| 8G6 | | | RLGPQARHG | 346 | 1 | |
| 18F2 | | | RLHR | 347 | 1 | |
| 1E3 | | | RMKQIVRKVEPIMT | 348 | 1 | |
| 19D3 | | | RMMSSSIQSLRKAGSEP | 349 | 1 | |
| 2E7 | | | RNWNKPSKRNCP | 350 | 1 | |
| 8C11 | | | RPQP | 351 | 1 | |
| 14C10 | | | RPQTDLPRTDVPGTLLVLRRAASPWSPTRGDPITCCLITVVISPREGA | 352 | 1 | PSIP1 protein |

TABLE 5-continued

Sequence Identity for phage clones associated with diagnosis and prognosis.

| Clone ID | Associated with Diagnosis | Prognosis | Translated Protein Sequences | SEQ ID NO | No. of Clones | Protein Identity |
|---|---|---|---|---|---|---|
| 13B11 | | | RPTDRQTSPGQTSPAR SLSSGGLRPPGVQRGA TP | 353 | 1 | |
| 2F6 | | | RQDCF | 354 | 1 | |
| 19C12 | | | RRLLGLYMVL | 355 | 1 | |
| 6F7 | | | RRRLW | 356 | 1 | |
| 14B8 | | | RRSRPSWPTG | 357 | 1 | |
| 1D7 | | | RRWTKAHCK | 358 | 1 | |
| 10H11 | | | RTLKAEVEKGSM | 359 | 1 | |
| 20E12 | | | RVPFTFFNLSL | 360 | 1 | |
| 22B12 | | | SFSRG | 361 | 1 | |
| 12A11 | | | SLSSTHFDICAGSGGR RSTKCKGLSTSVQCVY EEAH | 362 | 1 | |
| 23H10 | | | SNEGLKEVKISTCRLS KQSVSKLLNEKKS | 363 | 1 | |
| 15F12 | | | SNSHSPSTQGSLDCVF QETHLIWSDFVSPPKS HLEL | 364 | 1 | |
| 6D9 | | | SRRMA | 365 | 1 | |
| 12E11 | | | SRSASFMVGTTTVSDR LRTSDFRS | 366 | 1 | |
| 2H5 | | | SXARXPIQRESRMGD | 367 | 1 | |
| 13D4 | | | TIPGLRTPVSTRPTGTV PIPPIL | 368 | 1 | |
| 1G11 | | | TPTRDTSVMQIEETGR GKESSTMVVATTIHHG EATGTISMSSTGTRTTI MGTGDIWMPTVPEAI DPTTCPERGLMTSTSL RPHSSN | 369 | 1 | |
| 15H6 | | | TRLAWDLNWKLNVV | 370 | 1 | |
| 2A10 | | | TRPPSGRRPPTS | 371 | 1 | |
| 7H12 | | | TVLFGV | 372 | 1 | |
| 21H4 | | | VAQRPAGPVGWAAG GEALIG | 373 | 1 | |
| 1E11 | | | VFEDLKKYLKF | 374 | 1 | putative prolyl oligopeptidase |
| 20F12 | | | VFTVVISTSGARCQRQ Y | 375 | 1 | |
| 8C10 | | | VGSWERAGGPPRGEPP PVPAPCLSAPPRCS | 376 | 1 | |
| 24H12 | | | VGTIY | 377 | 1 | |
| 4E6 | | | VGVGIILS | 378 | 1 | |
| 2D6 | | | VHYHNINNLVK | 379 | 1 | |

TABLE 5-continued

Sequence Identity for phage clones associated with diagnosis and prognosis.

| Clone ID | Associated with Diagnosis | Associated with Prognosis | Translated Protein Sequences | SEQ ID NO | No. of Clones | Protein Identity |
|---|---|---|---|---|---|---|
| 21D5 | | | VIGSLMGMALNL | 380 | 1 | |
| 16A12 | | | VKKLVVGSWERAGGP PRGEPPPVPAPCLSAPP RCS | 381 | 1 | |
| 17D12 | | | VKNYF | 382 | 1 | |
| 9G3 | | | VLLYLKR | 383 | 1 | |
| 8C3 | | | VPGHARWLTPIIPALR DAEAGGS | 384 | 1 | |
| 9D8 | | | VVCSISLLSF | 385 | 1 | |
| 2E8 | | | VVFLR | 386 | 1 | |
| 14A9 | | | VVQTESLKSPSTYRCA QQDQVTSSSDCHHK | 387 | 1 | |
| 3E11 | | | VVVVVETGAI | 388 | 1 | |
| 1G1 | | | VYGRNYDGI | 389 | 1 | |
| 13A3 | | | WELNSEKTWTQGGEH HTPGPLWGRGARGGI ALG | 390 | 1 | |
| 16D10 | | | WKKNSRCY | 391 | 1 | |
| 22H4 | | | WKSGRS | 392 | 1 | |
| 24F10 | | | WMQSKYSKKSCCYVY G | 393 | 1 | |
| 11F5 | | | WPPELRLLTDQWQHSI LMGM | 394 | 1 | |
| 20H3 | | | WPPSSGPDCRFTHAIK L | 395 | 1 | |
| 16B7 | | | WRSSFPSTIYGKD | 396 | 1 | |
| 19A1 | | | WSGWPT | 397 | 1 | |
| 11F11 | | | YWTNPPTLTIPRHHLS TVLA | 398 | 1 | |

Example 4

Humoral Immune Response Profiles Associated with Prognosis in Prostate Cancer

This example describes the investigation of association of phage epitope clones with prognosis of prostate cancer. The prostate cancer cDNA phage display library described in Example 1 was biopanned using a pool of IgG from 16 prostate cancer sera (7 samples with Gleason=6 and 9 samples with Gleason=8 and 9). After construction of phage epitope microarray platform, 32 sera samples were screened. Raw data scanned were normalized as described in Example 1 for prostate cancer diagnosis. In order to identify the phage clones for prognosis, the samples were randomly assigned to a training set (31 samples) or a test set (11 samples) with an equal proportion of samples having the same Gleason score. T-test combined with leave-one-out cross validation was applied on the training set. Low risk patients with a Gleason score ≦6 and high risk patients with a Gleason score ≧8 were considered as two groups. A total of 21 clones were selected based on their best performance on the training set with 100% specificity (13/13) and 62.5% sensitivity (5/8). When applying these 21 phage epitopes on an independent test set, its performance was shown to be 100% specificity (4/4) and 75% sensitivity (5/6).

Example 5

Humoral Response to Lung Cancer

A. Materials and Methods

Patient population and samples. This study was approved by the Institutional Review Boards (IRBs) of the University of Michigan Medical School and the University of Pittsburgh. Sera from 150 lung adenocarcinomas were collected at the time of surgery from January 1995 to January 2003 at the University of Michigan Hospital. All the primary tumor sections were evaluated by a study pathologist and clinical information was collected (Tables 7-9). All patient identifiers were coded to protect confidentiality. As non-cancer control subjects, 100 serum samples with no known history of cancer were collected from the University of Michigan Clinical Pathology laboratories (Table 9). These samples were collected between 2001 and 2004 in 3 independent collection periods. No patients in this cohort received chemical or radiation treatment before the sera were collected. All sera were stored in aliquots at −80° C. until use.

An independent cohort of sera including 62 lung adenocarcinomas and 60 controls (Table 11), matched for both age and smoking status and collected between 2000 and 2005 was provided by the University of Pittsburgh Cancer Institute/Hillman Cancer Center.

Autoantibody profiling. By iterative biopanning of a phage display library derived from lung cancer tissue pools, phage-peptide microarrays were constructed and used to profile and define an autoantibody signature of lung adenocarcinoma.

Normalization and Analysis of the Microarray Data. Slides were scanned and quantified using the GenePix 400B scanner (Axon Laboratories, Providence, R.I.). According to the experimental design, the median of Cy5/Cy3 ratio was utilized to control small variations in the amount of phage epitope spotted. The spots were treated as missing values if the Cy3 signal alone was 50% less than the average value across slides. Each slide was then scaled to have the same median across slides. Clones that have more than 20% missing values across slides were excluded from further analyses. The entire dataset was quantile normalized (Bolstad et al., Bioinformatics 2003; 19:185-93) and base 2 log transformed. The missing values were then imputed using Sequential KNN imputation method (Kim et al., BMC Bioinformatics 2004; 5(1):160).

Statistical analysis. To determine whether autoantibody signatures can be used for the non-invasive detection of lung adenocarcinoma, class prediction was performed using the "BRB Array Tools" software. A greedy-pairs method (Bo et al., Genome Biol 2002; 3(4): RESEARCH0017) was used to select informative feature clones for the predictors. Briefly, all phage-peptide clones were ranked based on their individual t-scores on the training set, and the top-ranked clone $x_i$ was determined. Then the procedure searched for another clone $x_j$ that together with $x_i$ provided the best discrimination using as a measure the distance between centroids of the two classes with regard to the two clones when projected to the diagonal linear discriminant axis. These two clones were then removed from the clone set and the procedure was repeated on the remaining set until the specified number of pairs had been selected. This process was repeated for all training sets created during the leave-one-out cross-validation (LOOCV) and k-nearest neighbor (k=3) prediction was used to predict the left-out test sets during LOOCV. The number of pairs was varied from 2 to 20 in a stepwise fashion and the desired number of pairs was selected to minimize the error rate of LOOCV. After the phage-peptide pairs were determined, a predictor signature was applied to an independent test set.

Supervised clustering analysis was performed using Cluster and TreeView software. All other statistical analyses were performed with R or SPSS 11.5 (SPSS Inc.). The receiver operating characteristics (ROC) analysis was performed to assess the sensitivity and specificity of the autoantibody profile for discriminating lung cancer patient sera from control sera in the test set and for each individual autoantibody. The ROC curves have been widely used to assess the accuracy of a diagnostic test that yields continuous test results in clinical research areas. Briefly, a receiver operating characteristic plot is obtained by calculating the sensitivity and specificity of every test result value and plotting sensitivity against 1-specificity. A perfect diagnostic test would yield a "curve" that coincides with the left and top sides of the plot and a test that is completely useless would give a straight line from the bottom left corner to the top right corner. As a summary statistic, the area under the ROC curve (AUC) and the associated p values are usually used to assess the performance of a test.

Meta-analysis of gene expression of humoral response targets. The gene expression level of ubiquilin 1 was studied using ONCOMINE (Rhodes et al., Proc Natl Acad Sci USA 2004; 101(25):9309-14; Rhodes et al., Neoplasia 2004; 6(1):1-6). Briefly, ubiquilin 1 gene was queried in the database, and the results were filtered by selecting lung adenocarcinoma. The data from study classes of benign vs. cancer were used for box plots. p values for each group were calculated using student t-test.

2-D PAGE and Western blot analysis. Analytical 2-D PAGE protein quantification was performed as previously described (Chen et al., Mol Cell Proteomics 2002; 1(4):304-13). In this study, two protein spots were selected that represent native and phosphorylated forms of ubiquilin 1 on 2-D PAGE gels for further analysis. Protein separation and 2-D Western blotting were performed as described previously (Chen et al., Clin Cancer Res 2002; 8(7):2298-305). Individual membranes were incubated with mouse anti-human UBQLN1 antibody (Zymed Laboratories Inc, Carlsbad, Calif.) at 1 µg/ml concentration. Following additional washes, membranes were incubated with a secondary antibody conjugated to horseradish peroxidase (HRP) (Amersham, Piscataway, N.J.) at a 1:5000 dilution for 1 hour, then washed, and incubated for 1 min with enhanced ECL detection system (Amersham) and autoradiography.

Construction of T7 phage display lung cancer cDNA libraries. Total RNA was isolated according to the standard Trizol protocol separately from 7 lung cancer tissues (Table 8) from regions containing greater than 80% tumor cellularity. The integrity of each RNA preparation was assessed by the A260/A280 ratios greater than 1.8 as well as intact 28S and 18S RNA by gel electrophoresis. Equal amounts of total RNA from 7 tissues were pooled and poly(A) RNA was purified from the total RNA pool following Straight A's mRNA Isolation System protocol (Novagen, San Diego, Calif.). A total of 8.7 µg of mRNA was eluted and its integrity was judged by gel electrophoresis.

OrientExpression cDNA Synthesis and Cloning System (Novagen) was used for the construction of the T7 phage lung cancer cDNA libraries. cDNA was constructed using directional oligo(dT) primers. After vector ligation and T7 packaging, the cDNA phage display library was constructed and the library titers were determined by plaque assay with 4.2× $10^6$ pfu.

Amplification of libraries. Five ml of Lennoxl Broth Base (LB) with carbenicillin was inoculated at 37° C. overnight with a single colony of BLT5615 from a freshly streaked plate. Overnight culture was added to 100 ml of LB with carbenicillin and grown to an OD600 of 0.45. One mM IPTG was added and the cells then incubated for 20 additional minutes. A 5 ml culture was infected with the phage library at a multiplicity of infection (MOI) of 0.001-0.01 (i.e., 100-1000 cells for each pfu). The infected bacteria were incubated with shaking at 37° C. for 1-2 hr until lysis was observed. The phage lysate was then separated from bacterial debris by centrifugation at 8000×g for 10 min. The supernatant was collected and stored at −80° C. The quality and diversity of the phage library was tested by PCR amplification of 30 randomly selected phage colonies and DNA sequencing of 30 randomly selected phage colonies from the library.

Biopanning for phage-epitope clones specific to lung cancer and non-cancer controls. To enrich for T7 phage-peptides recognized by cancer or non-cancer control sera, separate biopanning selections were performed on 10 lung cancer and 3 non-cancer control sera (Table 9). Protein A/G agarose beads (Pierce, Rockford, Ill.) were used to purify IgGs from the sera of lung cancer patients and non-cancer controls. Briefly, 100 µl protein-A/G agarose beads were placed into 1.5 ml Eppendorf tubes and washed two times with 1×PBS. Washed beads were blocked with 1% BSA for 1 hr. The beads were then incubated at 4° C. with 50 µl of individual serum from control or lung cancer patients at 1:50 dilution in 1% BSA. After overnight incubation, the beads were washed with 1×PBS by centrifuging at 1000×g for 2 min. After three washes, 100 µl of 1×PBS was added to each sample. The A/G bead:human IgG complex tubes from the 3 control sera and 10 lung cancer sera were stored at 4° C. as stocks for four rounds of biopanning.

Twenty five µl of protein A/G bead:human IgG complex was incubated with 300 µl amplified phage library diluted 1:40 with 10% BSA at 4° C. overnight. The mixture was centrifuged at 1000×g for 2 min and the supernatant discarded. To elute bound phage, 50 µl of 1% SDS was added and shaken vigorously at room temperature for 10 min to break up the antibody:antigen reaction without disrupting T7 phage particles. The bound phage were removed from the beads by centrifugation at 5500×g for 8 min. Eluted phages were transferred to 5 ml culture of BLT5615 cells for amplification. A total of four cycles of affinity selection were carried out for enrichment of lung cancer or noncancer control related T7 phage-peptides.

Construction of the T7 phage-peptide microarrays. The phage library (~1010 pfu) from the fourth cycle of biopanning was diluted 1:108 and allowed to grow on LB agar plates with carbenicillin. 2.3k phage colonies were randomly picked and amplified in 96-well plates. The phage lysates were spotted onto ONCYTE nitrocellulose coated glass microscope slides (Grace Bio-Labs, Bend, Oreg.), using a GMS 417 printer (Affymetrix, Santa Clara, Calif.), to fabricate phage peptide microarrays. Eleven T7 phage clones without cDNA inserts were spotted as negative controls.

Assay of sera on phage-epitope microarrays. Before processing, microarray slides were rinsed briefly in PBS with 0.1% Tween-20 (PBS-T) to remove unbound phage, and then transferred immediately to 4% nonfat milk/PBS-T blocking solution for 1.5 hrs at room temperature. Serum from lung adenocarcinoma or control individuals was pre-adsorbed the day before with a 50-fold higher amount (v/v) of bacterial lysate (OD600 of 0.5) and then used for incubation. After blocking, 2.5 µl of human serum (final concentration 1:300 dilution) and T7-tag antibody (Novagen, 1:5000 dilution) in 4% nonfat milk in PBS was incubated with the slide in a screw-top slide hybridization tube.

Slides were incubated with sera from lung cancer or control for 1 hour at room temperature and then washed 5 times in PBS-T for 5 min each at room temperature. After washing, arrays were incubated with 2.5 ml of PBS-T milk containing Cy3-labeled goat anti-mouse antibody and Cy5-labeled goat anti-human IgG antibody (Jackson ImmunoResearch) both diluted 1:5,000 for 1 hr in the dark. Five washes were performed using PBS-T with 5 min each. The arrays were then dried by centrifugation at 500×g for 5 min.

Sequence analysis of humoral immune response targets. Phage-peptide clones identified as significant by this study were sequenced as previously described (Wang et al., N Engl J Med 2005; 353(12): 1224-35). DNA sequences and potentially translated protein sequences were aligned using NCBI BLAST.

Immunofluorescence and confocal microscopy. The lung cancer tissue section slides were soaked in xylene to remove paraffin. Antigen retrieval was by heating the slides in citrate buffer pH 6.0 for 15 minutes in a pressure cooker. Slides were then blocked in PBS-T containing 0.05% Tween and 5% normal donkey serum for 1 hour. Mouse anti-ubiquilin 1 antibody (Zymed) was added to the slides at 1:40 dilution in blocking buffer and incubated overnight at 4° C. Slides were then washed and incubated with secondary antibody at 1:1000 dilution (anti-mouse Alexa 555, Molecular Probes, Eugene, Oreg.) for 1 hour. After washing the slides with PBS-T and PBS, they were mounted using Vectashield mounting medium containing DAPI. Confocal images were taken with Zeiss LSM510 META (Carl Zeiss, Thornwood, N.Y.) imaging system. The double color images were exported as TIFF images.

Immunohistochemistry of tissue microarrays. A tissue microarray block was constructed and used the best representative morphological areas of the tumors in this study. Deparaffinized sections of the pulmonary adenocarcinoma tissue microarray were microwaved after pretreatment in citric acid to retrieve antigenicity. The sections were incubated with blocking solution containing PBS and 1% bovine serum album for 60 min at room temperature. The sections were incubated with mouse anti-ubiquilin 1 antibody (Zymed) at 1:100 dilution overnight at 4° C. The immunocomplexes were visualized by the immunoglobulin enzyme bridge technique using a Vector ABC-peroxidase kit (Vector Laboratories, Burlingame, Calif.) with 3,3'-diaminobenzidine tetrachloride as a substrate. The sections were lightly counterstained with hematoxylin.

TABLE 8

Clinical and pathology information of lung cancer tissues used for construction of T7 phage display cDNA library

| Sample ID* | Age | Sex | Stage | Survival** (months) | Differentiation |
|---|---|---|---|---|---|
| Ad2 | 59 | F | Ia | 33.0 | Well/moderate |
| Ad14 | 68 | F | Ib | 10.1 | Moderate |
| Ad84 | 58 | M | IIIa | 17.6 | Poor |
| Sq6 | 87 | F | Ib | 33.1 | Moderate |
| Sq16 | 61 | M | Ib | 10.2 | Well |
| Sq27 | 71 | M | Ib | 48.6 | Poor |
| Sq Ls-8 | 62 | M | Ib | 136.1 | Poor |

*Ad = adenocarcinomas, Sq = squamous;
**follow up time after surgery.

TABLE 9

Clinical and pathology information for lung cancer and noncancer control sera used for biopanning of T7 phage display cDNA library

| Sample ID* | Bp tube ID | Age | Sex | Stage | Survival** (months) | Differentiation |
|---|---|---|---|---|---|---|
| Ad22 | 1 | 81 | F | Ia | 21.2 | Well |
| Ad30 | 2 | 74 | F | Ib | 55.6 | Moderate |
| Ad32 | 3 | 55 | M | IIb | 29.3 | Well |
| Ad69 | 4 | 70 | M | Ia | 50.2 | Moderate |

TABLE 9-continued

Clinical and pathology information for lung cancer and noncancer control sera used for biopanning of T7 phage display cDNA library

| Sample ID* | Bp tube ID | Age | Sex | Stage | Survival** (months) | Differentiation |
|---|---|---|---|---|---|---|
| Ad75 | 5 | 88 | F | Ia | 69.2 | Well |
| Ad102 | 6 | 52 | F | IIb | 22.7 | Moderate |
| Sq20 | 7 | 76 | M | Ib | 62.4 | NA |
| Sq37 | 8 | 64 | F | IIIa | 23.1 | NA |
| Sq48 | 9 | 70 | M | IIIa | 34.4 | NA |
| Sq5 | 10 | 82 | F | IIb | 78.1 | NA |
| N1 | 12 | 56 | M | COPD | | |
| N2 | 13 | NA | NA | Pneumonia | | |
| N3 | 11 | 65 | F | Asthma, arthritis | | |

*Ad = adenocarcinomas, Sq = squamous, N = non-cancer control, Bp = biopanning, NA = non available
**follow up time after surgery

TABLE 10

Clinical information of training and validation set samples

| | Training set | Validation set |
|---|---|---|
| Adenocarcinomas (n) | 75 | 75 |
| Age average (years) | 64.9 | 64.9 |
| Age range | 43-88 | 34-90 |
| Male | 37 | 37 |
| Female | 38 | 38 |
| Stage I + II | 58 | 58 |
| Stage III + IV | 17 | 17 |
| Dead | 34 | 34 |
| Alive | 41 | 41 |
| Survival time (months) | 31.5 | 32.3 |
| Non-cancer control (n) | 50 | 50 |
| Age average (years) | 61.6 | 60.8 |
| Age range | 50-77 | 40-77 |
| Male | 30 | 31 |
| Female | 20 | 19 |

TABLE 11

Clinical information of Pittsburgh samples

| Adenocarcinomas (n) | 62 |
|---|---|
| Age average (years) | 66.7 |
| Age range | 49-82 |
| Male | 23 |
| Female | 39 |
| Non-cancer control (n) | 60 |
| Age average (years) | 63.9 |
| Age range | 51-83 |
| Male | 30 |
| Female | 30 |

B. Results and Discussion

Construction and analysis of the T7 phage-peptide microarrays. A schematic overview of the approach used to identify autoantibody signatures of lung cancer is shown in FIG. 4, US 20060014138 and (N Engl J Med 2005; 353(12): 1224-35). To develop a T7 phage display library for lung cancer, total RNA was isolated and pooled from 7 lung cancer tissues each of which was comprised of at least 80% tumor cells (Table 8). Once packaged into the T7 phage system, peptides from the library were expressed as a fusion protein with the capsid 10B protein on the surface of the phage. This protein serves as a "bait" to capture autoantibodies present in serum. To enrich for T7 phage-peptides recognized by cancer or non-cancer control sera, separate biopanning selections were performed using 10 lung cancer and 3 non-cancer control sera (Table 9). Protein A/G beads, bound with antibodies from sera, were used to isolate phage-peptide particles that could bind these sera antibodies. The bound phage were eluted and amplified in bacteria, thus completing one round of biopanning. After four rounds of biopanning, phage particles expressing peptides that specifically elicit a humoral immune response in lung cancer patients or controls were enriched. A total of 2304 phage-peptide clones were randomly selected from the biopanned phage libraries to generate phage-peptide microarrays. Once in a microarray format, these enriched phage-peptide clones can be used to interrogate serum samples for humoral immune response markers.

Using this 2.3K phage-peptide microarray, sera from 150 lung adenocarcinoma patients and 100 non-cancer control subjects was evaluated (Table 10). A two-color system was used in which a green fluorescent dye (Cy3) was used to measure levels of the capsid 10B fusion protein spotted as a control, and a red fluorescent dye (Cy5) was used to measure levels of bound IgG (Table 10). Therefore, increased Cy5/Cy3 ratios represented varying levels of immune reactivity. Most of the sera from lung adenocarcinoma patients exhibited antibody repertoires that display distinct reactivity relative to controls. The correlation coefficients of 20 replicate experiments ranged between 0.78-0.96 suggesting excellent reproducibility (FIG. 6). After data normalization and imputation of missing values, 2304 clones were used for subsequent statistical analyses.

Autoantibody profiles for the diagnosis of lung adenocarcinoma. It was next determined whether autoantibody signatures can be used for the non-invasive detection of lung adenocarcinoma. First, 250 lung cancer patients and non-cancer controls were divided into a training set and a validation set with equal number of samples (comprised of 75 cancer sera and 50 control sera in each set). The collection of cases and controls were separately matched based on age and sex; the training and validation samples were generated by assigning one sample from the pair randomly to each set (Table 10). In the training set, a "greedy-pairs" method (Bo et al., Genome Biol 2002; 3(4):RESEARCH0017) was adopted to select "informative" autoantibodies and k-nearest neighbor analysis (k=3) was employed to build a class prediction model. Different autoantibody pairs ranging from 2 to 20 were tested in a stepwise fashion and it was observed that the top-ranked 22 autoantibodies (or 11 autoantibody pairs) had the best classification accuracy (85.6%, $107/125$) in the training set according to leave-one-out cross-validation (LOOCV) with a sensitivity of 82.7% ($62/75$) and a specificity of 90.0% ($45/50$) (Table 6). These 22 autoantibodies were then used as a class predictor on an independent validation set, resulting in 85.3% ($64/75$) sensitivity and 86.0% ($43/50$) specificity (Table 6).

In order to evaluate the performance of this 22-autoantibody signature on a continuous scale, a compound covariate predictor approach was utilized to create an index score for each validation sample as described previously (Radmacher et al., J Comput Biol 2002; 9(3):505-11; Tukey et al., Control Clin Trials 1993; 14(4):266-85). Each sample's value for each of those 22 autoantibodies was multiplied by the corresponding coefficients derived from univariate logistic regressions on the training set with cancer/control as a binary response variable and then the values were totaled. The created index scores were then assessed by the receiver operating characteristic (ROC) curve, which provided a pure index of a test's accuracy by plotting the sensitivity against 1-specificity for each result value of the test. The ROC analysis yielded the area under the ROC curve (AUC) of 0.92 (P<0.0001, 95% confidence interval (CI)=0.88-0.97) for the validation set (FIG. 1C), demonstrating the strong discriminative power of this 22-antoantibody signature.

Figure 17:
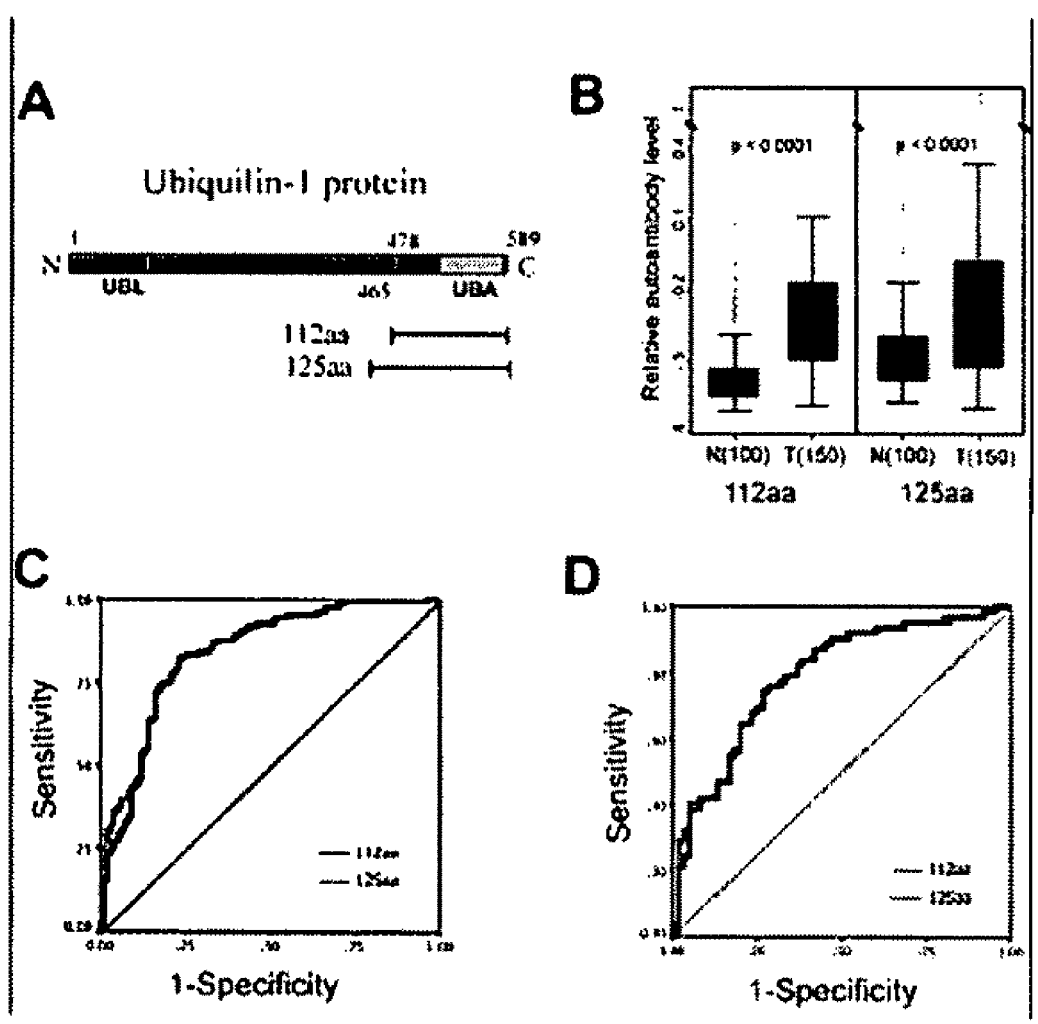
FIG. 17 shows the identification and characterization of ubiquilin 1 as a humoral response target in lung adenocarcinoma patients. A, Ubiquilin 1 contains a ubiquitin-like domain (UBL) in the N-terminus and a ubiquitin-associated domain (UBA) in C-terminal region. B, Immunoreactivity against two phage-peptide clones encoding fragments of ubiquilin 1. C, ROC curve of the two phage-peptide clones encoding different over-lapping fragments of ubiquilin 1 exhibited AUCs of 0.84 (95% CI=0.78-0.89) and 0.71 (95% CI=0.65-0.77), respectively, on 150 adenocarcinomas and 100 non-cancer controls of University of Michigan cohort sera. D, ROC curve of the two phage-peptide clones encoding different over-lapping fragments of ubiquilin 1 exhibited AUCs of 0.79 (95% CI=0.71-0.87) and 0.74 (95% CI=0.65-0.83), respectively, on 62 adenocarcinomas and 60 non-cancer controls of University of Pittsburgh cohort sera.

Identification of ubiquilin 1. The phage-peptide microarray strategy facilitated identification of autoantibody targets by sequencing the respective phage cDNA clone. Table 6 lists the identity of the peptide sequences of the 22 diagnosis-related humoral immune response targets. Of these 22 diagnosis-related targets, peptides encoding ubiquilin 1 were found in 9 independent phage-peptide cDNA clones based on the top 100 lung adenocarcinoma associated phage-peptides sequenced. Seven immunoreactive phage-peptides clones of ubiquilin 1 spanned 112 amino acids (aa) from aa478 to aa589 and two clones spanned 125aa from aa465 to aa589 (FIG. 17A). Both peptide-stretches of ubiquilin 1 were the target of autoantibodies in lung adenocarcinoma patients relative to control subjects (P<0.0001) (FIG. 17B). For lung cancer diagnosis, a single autoantibody against phage-peptide clone encoding 112aa or 125aa of ubiquilin 1 exhibited AUCs of 0.84 (95% CI=0.78-0.89) and 0.71 (95% CI=0.65-0.77), respectively (FIG. 17C).

Figure 20:
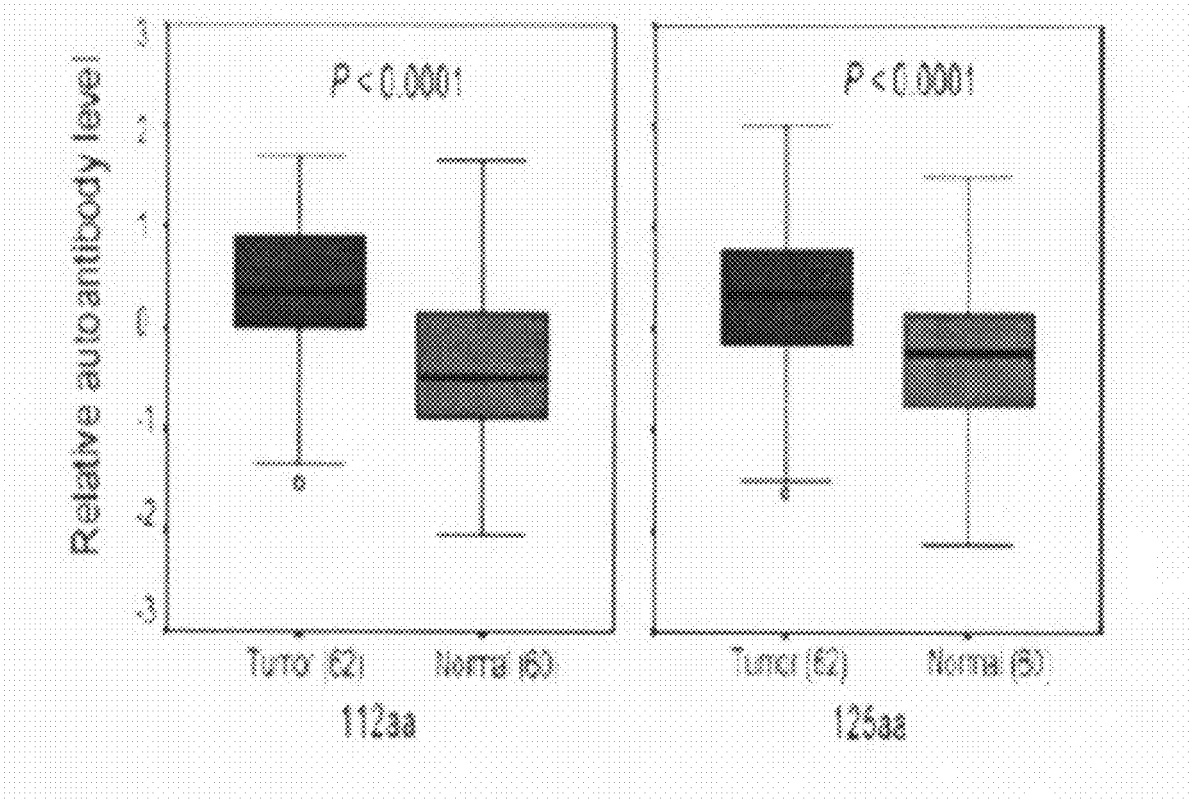
FIG. 20 shows a boxplot showing that the immunoreactivity against two phagepeptide clones encoding fragments of ubiquilin-1 were higher in tumors relative to controls in Pittsburgh sera.

A more focused phage array with 1129 clones, an independent, but clinically and demographically similar, case-control cohort of sera from the University of Pittsburgh was next examined. These included 62 lung adenocarcinomas and 60 controls (Table 11), matched for both age and smoking status. The autoantibodies for both isoforms of ubiquilin 1 (112aa and 125aa) were also significantly higher in case sera compared to controls (P<0.0001) (FIG. 20), exhibiting AUCs of 0.79 (95% CI=0.71-0.87) and 0.74 (95% CI=0.65-0.83), respectively (FIG. 17D).

Ubiquilin 1, also called PLIC, contains a ubiquitin-like domain (UBL) in the N-terminus and a ubiquitin-associated domain (UBA) in C-terminal region, which are essential for its ability to inhibit the degradation of several ubiquitin-dependent proteasome substrates including p53, IκB, and the GABA(A) receptor (Kleijnen et al., Mol Cell 2000; 6(2):409-19; Mah et al., J Cell Biol 2000; 151(4):847-62). Ubiquilin 1 is also involved in the proteasome-mediated degradation of various proteins, including presenilins, cyclin A, hepatitis C virus RNA-dependent RNA polymerase protein and amyloid precursor protein (Hiltunen et al., J Biol Chem 2006; 281(43): 32240-53; Thomas et al., J Biol Chem 2006; 281(36):26400-7). In addition, it has been suggested that splice variants of the ubiquilin 1 gene are associated with an increased risk of developing Alzheimer's disease (Slifer et al., N Engl J Med 2005; 352(26):2752-3; author reply −3).

Figure 18:
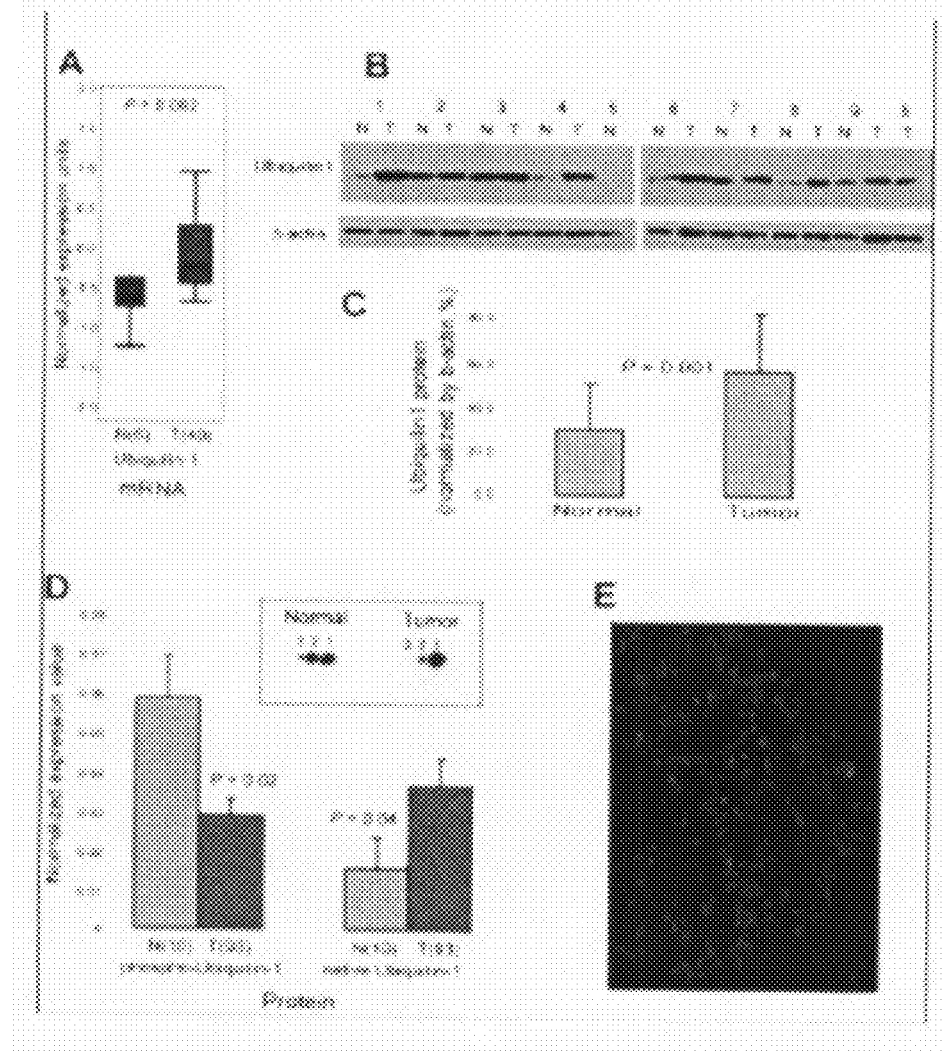
FIG. 18 shows Ubiquilin 1 mRNA and protein expression in lung cancer tissues. A, mRNA transcript levels of ubiquilin 1 in lung adenocarcinoma as assessed using ONCOMINE and derived from the Garber et al (4) lung gene expression profiling study. B, & C, Western blot showed that the ubiquilin 1 protein was significantly higher in lung tumors relative to normal lung tissues. D, Quantitative 2-D PAGE analysis of ubiquilin 1 in lung adenocarcinoma tissues. Inset, immunoblot analysis of ubiquilin 1 in lung adenocarcinoma. 1=unphosphorylated isoform (native ubiquilin 1); 2, 3=phosphorylated isoforms (p-ubiquilin 1). E, Immunofluorescence staining of ubiquilin 1 in lung adenocarcinoma.
Figure 19:
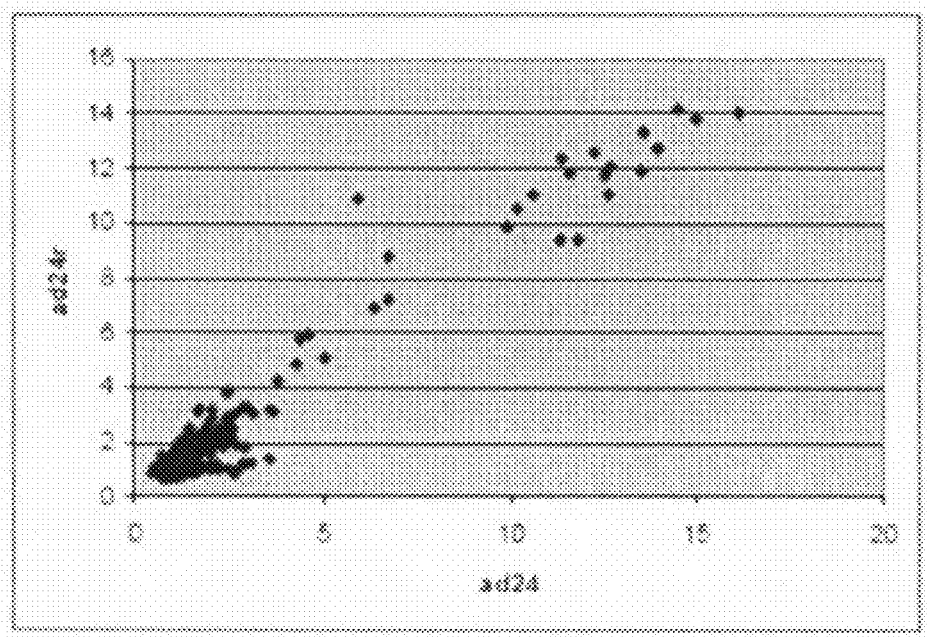
FIG. 19 shows a representative figure of one sample showed the correlation coefficients of replicate experiments is 0.96
Figure 21:
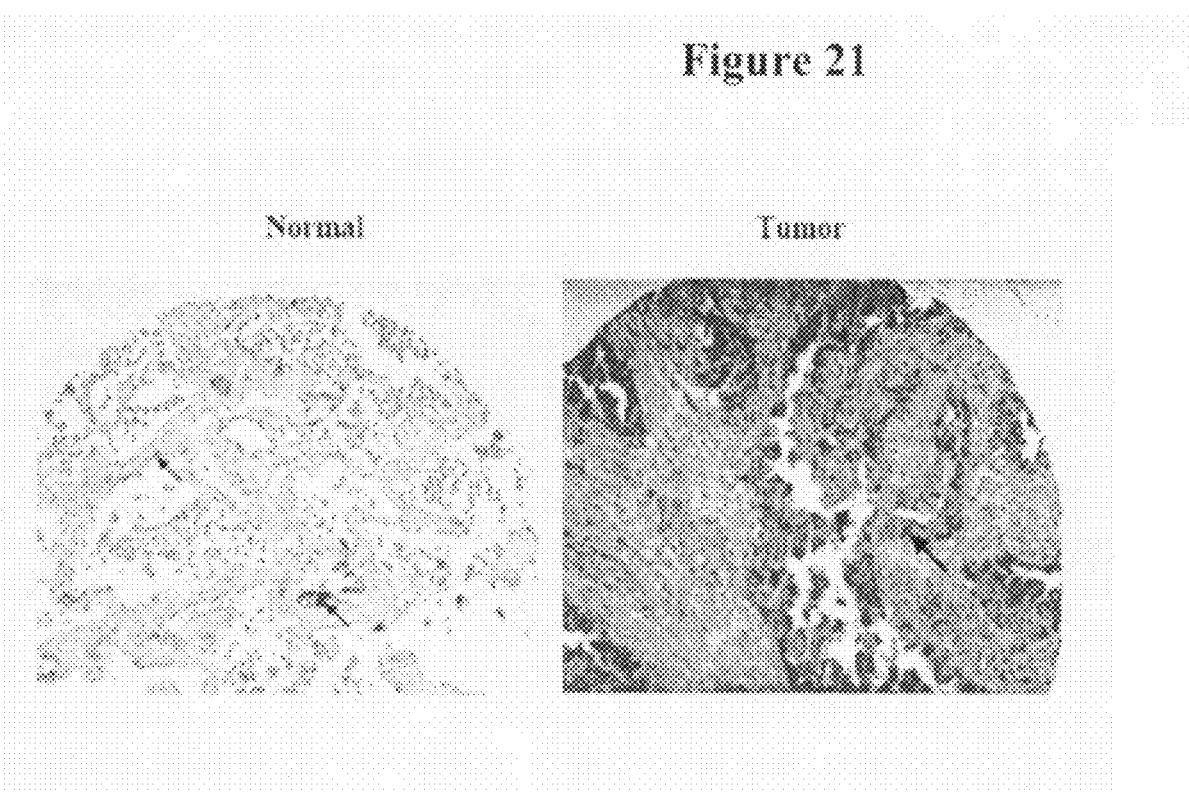
FIG. 21 shows that immunohistochemical staining using anti-ubiquilin 1 antibody showed weak cytoplasmic staining in type 1 and 2 epithelial cells and macrophages within normal lung tissues (arrows) and strong cytoplasmic staining of ubiquilin 1 in lung adenocarcinoma tumor cells (arrow).
Figure 22:
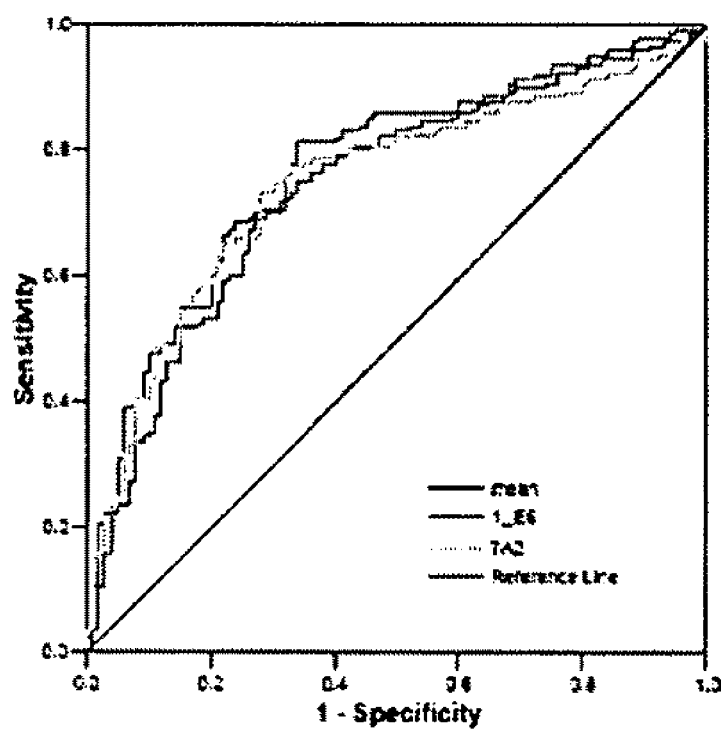
FIG. 22 shows a ROC curve of the two phage-peptide clones encoding different overlapping fragments (clone 1_E6 spanned aa113-197 and clone 7A2 spanned aa113-219 CDS) of heat shock protein 70 showing identical increased immune response patterns in lung adenocarcinomas relative to controls with AUC 0.75 (based on 150 adenocarcinomas and 100 non-cancer controls) and mean of these two clones was AUC 0.77.

Ubiquilin 1 mRNA and protein are increased in lung tumors. An independent gene expression profiling study of lung cancer showed that the mRNA for ubiquilin 1 was increased in lung adenocarcinomas relative to normal lung (Garber et al., Proc Natl Acad Sci USA 2001; 98(24):13784-9) (FIG. 18A). To assess ubiquilin 1 protein levels, Western blot analysis was performed using an ubiquilin 1 specific antibody and 9 pairs of lung tumor and associated normal lung tissue. Ubiquilin 1 protein levels were significantly higher in lung cancer compared to normal lung tissues (FIG. 18B, C). Using the same antibody with two-dimensional (2-D) Western blot analysis of lung adenocarcinoma tissues, two isoforms of the ubiquilin 1 protein were detected (FIG. 3D, 1=a native isoform, 2=phosphorylated isoform). These two spots were matched to a compendium of 2-D PAGE gels (Chen et al., Proc Natl Acad Sci USA 2003; 100(23):13537-42) and quantified, showing that the unphosphorylated form was more abundant among the 93 lung adenocarcinomas compared to 10 normal lung tissues. The phosphorylated form of ubiquilin 1 was decreased in tumors with expression of an additional phosphorylated isoform of ubiquilin 1 exclusively present in normal lung (FIG. 18D, 3=second phosphorylated isoform). To assess the cellular localization and expression of ubiquilin 1 antigen in situ, lung adenocarcinoma and normal lung tissues were examined using immunofluorescence (FIG. 18E) and immunohistochemical analysis. Using both experimental approaches, strong cytoplasmic staining of ubiquilin 1 was observed in lung adenocarcinomas and a week cytoplasmic staining was found in type 1 and 2 epithelial cells as well as macrophages in normal lung tissues (FIG. 21).

In addition to ubiquilin 1, two independent, overlapping clones of heat shock 70 protein were in the top 100 lung adenocarcinoma associated phage-peptides sequenced. Autoantibodies against heat shock 70 protein were not selected in the 22 diagnosis-related autoantibody targets based on the supervised models we employed (listed in Table 6). Both phage-peptide clones encoding heat shock protein 70 showed identical increased immune response patterns in lung cancer relative to controls with AUC 0.75 (FIG. 9). This protein has been previously reported to elicit an immune response in lung cancer patients (Zhong et al., Cancer Detect Prev 2003; 27(4):285-90; Zhong et al., Proteomics 2004; 4(4):1216-25).

Most of the phage peptides identified in Table 6 (FIG. 23) were either in untranslated regions of expressed genes or out of frame in the coding sequence of known genes. These peptides may be weakly homologous to known proteins or may have no distinct homology to the primary sequences of known proteins and thus may be "mimotopes" (i.e., stretches of amino acids that mimic an antigen but are not homologous at the sequence level) (Wang X, Yu J, Sreekumar A, et al. Autoantibody signatures in prostate cancer. N Engl J Med 2005; 353(12):1224-35).

The present example describes a robust approach combining phage display with protein microarrays to detect lung cancer based on the endogenous humoral immune response signature. As this approach relies on a multiplex set of markers, it is less likely to suffer from the drawbacks of monitoring any single biomarker (Koziol et al., Clin Cancer Res 2003; 9(14):5120-6). The present results have led to the detection of a number of novel peptide targets that elicit a humoral immune response in lung cancer patients. Several of the peptides identified represent known proteins including ubiquilin 1, and heat shock 70 protein. Ubiquilin 1 plays a role in the ubiquitination pathway, which has been implicated in various cancer progression models (Kleijnen et al., Mol Cell 2000; 6(2):409-19; Rossi et al., Breast Cancer Res 2003; 5(1):16-22; Huebener et al., Expert Opin Biol Ther 2003; 3(1):187-92).

In summary, the present studies demonstrate that autoantibody signatures of lung cancer have utility for the screening and early diagnosis of lung cancer due to the greater than 80% sensitivity and specificity of the assay. As lung cancer lacks an accepted biomarker for screening such as PSA for prostate cancer, this approach has a clinical use as well as in the screening of high risk populations. Unlike gene expression studies of tumor tissues, autoantibody profiling is performed in serum, which can be obtained much less invasively and is easily monitored over time. Likewise, while there has been intensive activity in the use of proteomic approaches to identify biomarkers in sera (Xiao et al, Dis Markers 2003; 19(1): 33-9), monitoring the immune response takes advantage of the inherent biological amplification provided by autoantibodies which can be more easily detected than low abundant proteins in a complex biological milieu such as serum.

All publications and patents mentioned in the above specification are herein incorporated by reference. Various modifications and variations of the described method and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for detecting lung cancer, comprising:
   a) providing a sample from a subject suspected of having lung cancer;
   b) detecting the presence or absence of an autoantibody to Ubiquilin 1 in said sample; and
   c) detecting lung cancer in said sample when said autoantibody to Ubiquilin 1 is present in said sample.

2. The method of claim 1, wherein said detecting the presence of an autoantibody to said Ubiquilin 1 comprises detecting the binding of an antibody to said autoantibody.

3. The method of claim 1, wherein said method further comprises step c) providing a prognosis to said subject.

4. The method of claim 1, wherein said sample is selected from the group consisting of a serum sample and a blood sample.

* * * * *

SEQUENCE LISTING

```
<160> NUMBER OF SEQ ID NOS: 486

<210> SEQ ID NO 1
<211> LENGTH: 112
<212> TYPE: PRT
<213> ORGANISM: Homo sapiens

<400> SEQUENCE: 1

Pro Gly Leu Ile Pro Gly Phe Thr Pro Gly Leu Gly Ala Leu Gly Ser
1               5                   10                  15

Thr Gly Gly Ser Ser Gly Thr Asn Gly Ser Asn Ala Thr Pro Ser Glu
            20                  25                  30

Asn Thr Ser Pro Thr Ala Gly Thr Thr Glu Pro Gly His Gln Gln Phe
        35                  40                  45

Ile Gln Gln Met Leu Gln Ala Leu Ala Gly Val Asn Pro Gln Leu Gln
    50                  55                  60

Asn Pro Glu Val Arg Phe Gln Gln Leu Glu Gln Leu Ser Ala Met
65                  70                  75                  80

Gly Phe Leu Asn Arg Glu Ala Asn Leu Gln Ala Leu Ile Ala Thr Gly
                85                  90                  95

Gly Asp Ile Asn Ala Ala Ile Glu Arg Leu Leu Gly Ser Gln Pro Ser
            100                 105                 110

<210> SEQ ID NO 2
<211> LENGTH: 125
<212> TYPE: PRT
<213> ORGANISM: Homo sapiens

<400> SEQUENCE: 2

Gln Ile Gln Gln Gly Leu Gln Thr Leu Ala Thr Glu Ala Pro Gly Leu
1               5                   10                  15

Ile Pro Gly Phe Thr Pro Gly Leu Gly Ala Leu Gly Ser Thr Gly Gly
            20                  25                  30

Ser Ser Gly Thr Asn Gly Ser Asn Ala Thr Pro Ser Glu Asn Thr Ser
        35                  40                  45

Pro Thr Ala Gly Thr Thr Glu Pro Gly His Gln Gln Phe Ile Gln Gln
    50                  55                  60

Met Leu Gln Ala Leu Ala Gly Val Asn Pro Gln Leu Gln Asn Pro Glu
65                  70                  75                  80

Val Arg Phe Gln Gln Gln Leu Glu Gln Leu Ser Ala Met Gly Phe Leu
                85                  90                  95

Asn Arg Glu Ala Asn Leu Gln Ala Leu Ile Ala Thr Gly Gly Asp Ile
            100                 105                 110

Asn Ala Ala Ile Glu Arg Leu Leu Gly Ser Gln Pro Ser
        115                 120                 125

<210> SEQ ID NO 3
<211> LENGTH: 107
<212> TYPE: PRT
```

<213> ORGANISM: Homo sapiens

<400> SEQUENCE: 3

```
Asn Ser Leu Glu Ser Tyr Ala Phe Asn Met Lys Ala Thr Val Glu Asp
1               5                   10                  15

Glu Lys Leu Gln Gly Lys Ile Asn Asp Glu Asp Lys Gln Lys Ile Leu
            20                  25                  30

Asp Lys Cys Asn Glu Ile Ile Asn Trp Leu Asp Lys Asn Gln Thr Ala
        35                  40                  45

Glu Lys Glu Glu Phe Glu His Gln Gln Lys Glu Leu Glu Lys Val Cys
    50                  55                  60

Asn Pro Ile Ile Thr Lys Leu Tyr Gln Ser Ala Gly Gly Met Pro Gly
65                  70                  75                  80

Gly Met Pro Gly Gly Phe Pro Gly Gly Ala Pro Pro Ser Gly Gly
                85                  90                  95

Ala Ser Ser Gly Pro Thr Ile Glu Glu Val Asp
            100                 105
```

<210> SEQ ID NO 4
<211> LENGTH: 68
<212> TYPE: PRT
<213> ORGANISM: Homo sapiens

<400> SEQUENCE: 4

```
Gly Ala Tyr Pro Ser Thr Tyr Asp Leu Asp Ile Glu Val His Gly Gly
1               5                   10                  15

Leu Gln Pro Cys Leu Glu Leu Glu Tyr Gly Ala Glu Pro Ile Val Gly
            20                  25                  30

Ile Lys Gly Ser Leu Asp Ser Leu Ala Ser Glu Ala Thr Met Lys
        35                  40                  45

Val Glu Ser Trp Gly Ser Arg Lys His Glu Ala Leu Tyr Cys Ile Gln
    50                  55                  60

Asn Thr Glu Ile
65
```

<210> SEQ ID NO 5
<211> LENGTH: 18
<212> TYPE: PRT
<213> ORGANISM: Homo sapiens

<400> SEQUENCE: 5

```
Gln Ala Phe Pro Gln Gln Thr Gly Arg Arg Ala Thr Ser Glu Pro Thr
1               5                   10                  15

Ala Met
```

<210> SEQ ID NO 6
<211> LENGTH: 13
<212> TYPE: PRT
<213> ORGANISM: Homo sapiens

<400> SEQUENCE: 6

```
Val Thr Arg Pro Pro Ser Gly Arg Arg Pro Pro Thr Ser
1               5                   10
```

<210> SEQ ID NO 7
<211> LENGTH: 52
<212> TYPE: PRT
<213> ORGANISM: Homo sapiens

<400> SEQUENCE: 7

```
Ala Val Ala Gln Met Arg Met Arg Met Lys Met Arg Met Arg Met Gly
1               5                   10                  15

Gln Glu Gly Thr Gln Gln Glu Pro Gln Gln Gln Asn Ile Leu Glu Asp
            20                  25                  30

Asp Thr Arg Asp Gln Gly Ala His Thr Gly Gly Pro Pro Gly Lys Pro
            35                  40                  45

Asp Ala Asp Glu
        50
```

<210> SEQ ID NO 8
<211> LENGTH: 24
<212> TYPE: PRT
<213> ORGANISM: Homo sapiens

<400> SEQUENCE: 8

```
Gln Glu Arg Gln Thr Arg Ala Gln Lys Lys Gly Thr Ser Ser Ser Gly
1               5                   10                  15

His Ser Thr Thr Lys Val Ile Pro
            20
```

<210> SEQ ID NO 9
<211> LENGTH: 219
<212> TYPE: PRT
<213> ORGANISM: Homo sapiens

<400> SEQUENCE: 9

```
Gly Thr Glu Ile Asp Gly Arg Ser Ile Ser Leu Tyr Tyr Thr Gly Glu
1               5                   10                  15

Lys Gly Gln Asn Gln Asp Tyr Arg Gly Gly Lys Asn Ser Thr Trp Ser
            20                  25                  30

Gly Glu Ser Lys Thr Leu Val Leu Ser Asn Leu Ser Tyr Ser Ala Thr
            35                  40                  45

Glu Glu Thr Leu Gln Glu Val Phe Glu Lys Ala Thr Phe Ile Lys Val
        50                  55                  60

Pro Gln Asn Gln Asn Gly Lys Ser Lys Gly Tyr Ala Phe Ile Glu Phe
65                  70                  75                  80

Ala Ser Phe Glu Asp Ala Lys Glu Ala Leu Asn Ser Cys Asn Lys Arg
                85                  90                  95

Glu Ile Glu Gly Arg Ala Ile Arg Leu Glu Leu Gln Gly Pro Arg Gly
            100                 105                 110

Ser Pro Asn Ala Arg Ser Gln Pro Ser Lys Thr Leu Phe Val Lys Gly
            115                 120                 125

Leu Ser Glu Asp Thr Thr Glu Glu Thr Leu Lys Glu Ser Phe Asp Gly
        130                 135                 140

Ser Val Arg Ala Arg Ile Val Thr Asp Arg Glu Thr Gly Ser Ser Lys
145                 150                 155                 160

Gly Phe Gly Phe Val Asp Phe Asn Ser Glu Glu Asp Ala Lys Ala Ala
                165                 170                 175

Lys Glu Ala Met Glu Asp Gly Glu Ile Asp Gly Asn Lys Val Thr Leu
            180                 185                 190

Asp Trp Ala Lys Pro Lys Gly Glu Gly Gly Phe Gly Gly Arg Gly Gly
            195                 200                 205

Gly Gln Ala Cys Gly Arg Thr Arg Val Thr Ser
        210                 215
```

<210> SEQ ID NO 10

```
<211> LENGTH: 140
<212> TYPE: PRT
<213> ORGANISM: Homo sapiens

<400> SEQUENCE: 10

Leu Gly Thr Ala Ile Gly Pro Val Gly Pro Val Thr Pro Ile Gly Pro
1               5                   10                  15

Ile Gly Pro Ile Val Pro Phe Thr Pro Ile Gly Pro Ile Gly Pro Ile
                20                  25                  30

Gly Pro Thr Gly Pro Ala Ala Pro Pro Gly Ser Thr Gly Ser Gly Gly
            35                  40                  45

Pro Thr Gly Pro Thr Val Ser Ser Ala Ala Pro Ser Glu Thr Thr Ser
50                  55                  60

Pro Thr Ser Glu Ser Gly Pro Asn Gln Gln Phe Ile Gln Gln Met Val
65                  70                  75                  80

Gln Ala Leu Ala Gly Ala Asn Ala Pro Gln Leu Pro Asn Pro Glu Val
                85                  90                  95

Arg Phe Gln Gln Gln Leu Glu Gln Leu Asn Ala Met Gly Phe Leu Asn
                100                 105                 110

Arg Glu Ala Asn Leu Gln Ala Leu Ile Ala Thr Gly Gly Asp Ile Asn
                115                 120                 125

Ala Ala Ile Glu Arg Leu Leu Gly Ser Gln Pro Ser
            130                 135                 140

<210> SEQ ID NO 11
<211> LENGTH: 20
<212> TYPE: PRT
<213> ORGANISM: Homo sapiens

<400> SEQUENCE: 11

Ala Glu Arg Val Ser Glu Thr Trp Tyr Met Lys Gly Thr Val Gln His
1               5                   10                  15

Cys Asp Phe Asn
            20

<210> SEQ ID NO 12
<211> LENGTH: 25
<212> TYPE: PRT
<213> ORGANISM: Homo sapiens

<400> SEQUENCE: 12

Ala Lys His Ser Ser Ala Tyr Thr Phe Phe His Pro His Ser Asn Pro
1               5                   10                  15

Val Ser His Tyr His Pro Arg Phe Ile
                20                  25

<210> SEQ ID NO 13
<211> LENGTH: 8
<212> TYPE: PRT
<213> ORGANISM: Homo sapiens

<400> SEQUENCE: 13

Ala Arg Trp Gly Leu Arg Met Gly
1               5

<210> SEQ ID NO 14
<211> LENGTH: 12
<212> TYPE: PRT
<213> ORGANISM: Homo sapiens

<400> SEQUENCE: 14
```

```
Cys Cys Leu Pro Arg Phe Thr Glu Ser Thr Ser Val
1               5                   10

<210> SEQ ID NO 15
<211> LENGTH: 8
<212> TYPE: PRT
<213> ORGANISM: Homo sapiens

<400> SEQUENCE: 15

Gly Glu Leu Lys Gly Lys Glu Lys
1               5

<210> SEQ ID NO 16
<211> LENGTH: 9
<212> TYPE: PRT
<213> ORGANISM: Homo sapiens

<400> SEQUENCE: 16

Gly Lys Val Gly Gly Gly Phe Leu Ile
1               5

<210> SEQ ID NO 17
<211> LENGTH: 53
<212> TYPE: PRT
<213> ORGANISM: Homo sapiens

<400> SEQUENCE: 17

Gly Pro Gln Thr Asp Arg Pro Pro Gln Asp Arg Arg Pro Arg His Ala
1               5                   10                  15

Pro Cys Pro Gln Glu Gly Cys Val Pro Leu Glu Ser Asn Ala Gly Arg
                20                  25                  30

Pro His Asn Leu Leu Ser Asp Tyr Ser Cys Asp Lys Ser Pro Gly Arg
        35                  40                  45

Ser Met Thr Arg Gly
        50

<210> SEQ ID NO 18
<211> LENGTH: 20
<212> TYPE: PRT
<213> ORGANISM: Homo sapiens

<400> SEQUENCE: 18

Gly Ser Arg Gly Gln Glu Phe Lys Thr Ser Leu Ala Asn Met Val Lys
1               5                   10                  15

Leu His Leu Tyr
        20

<210> SEQ ID NO 19
<211> LENGTH: 17
<212> TYPE: PRT
<213> ORGANISM: Homo sapiens

<400> SEQUENCE: 19

His Leu His Asn Pro Gly Asp Pro Cys Arg Val Met Ser Gln Arg Pro
1               5                   10                  15

Leu

<210> SEQ ID NO 20
<211> LENGTH: 38
<212> TYPE: PRT
<213> ORGANISM: Homo sapiens
```

```
<400> SEQUENCE: 20

His Pro Trp Ala Pro Lys Gly Trp Ala Arg Trp Gly Ala Ala Pro Trp
1               5                   10                  15

Ala Ala Gly Trp Pro Gly Thr Pro Ala Leu Ser Ala Gly Thr Pro Lys
            20                  25                  30

Leu Ala Ala Ala Leu Glu
        35

<210> SEQ ID NO 21
<211> LENGTH: 30
<212> TYPE: PRT
<213> ORGANISM: Homo sapiens

<400> SEQUENCE: 21

Ile Ile Ser Arg Arg Gly Thr Asn Thr Ala Pro Leu Thr Ser Ser Ser
1               5                   10                  15

Ala Thr Thr Arg Thr Pro Ala Arg Leu Trp Cys Cys Arg Ser
            20                  25                  30

<210> SEQ ID NO 22
<211> LENGTH: 24
<212> TYPE: PRT
<213> ORGANISM: Homo sapiens

<400> SEQUENCE: 22

Ile Lys Thr Lys Glu Asn Met Leu Arg Glu Ala Arg Gln Lys Gly Leu
1               5                   10                  15

Val Thr Asn Gly Ser Pro Ser Asp
            20

<210> SEQ ID NO 23
<211> LENGTH: 28
<212> TYPE: PRT
<213> ORGANISM: Homo sapiens

<400> SEQUENCE: 23

Ile Arg Ile Ala Pro Leu Glu Val Lys Phe Leu Asp Arg Arg Lys Thr
1               5                   10                  15

Asp Gln Ser Glu Ser Ile Cys Gln Glu Cys Phe His
            20                  25

<210> SEQ ID NO 24
<211> LENGTH: 6
<212> TYPE: PRT
<213> ORGANISM: Homo sapiens

<400> SEQUENCE: 24

Lys Lys Lys Asp Asn Leu
1               5

<210> SEQ ID NO 25
<211> LENGTH: 17
<212> TYPE: PRT
<213> ORGANISM: Homo sapiens
<220> FEATURE:
<221> NAME/KEY: misc_feature
<222> LOCATION: (16)..(16)
<223> OTHER INFORMATION: Xaa can be any naturally occurring amino acid

<400> SEQUENCE: 25

Lys Lys Thr Ser Gly Pro Asp Gly Phe Thr Gly Glu Arg Tyr Gln Xaa
1               5                   10                  15
```

Ile

<210> SEQ ID NO 26
<211> LENGTH: 11
<212> TYPE: PRT
<213> ORGANISM: Homo sapiens

<400> SEQUENCE: 26

Lys Tyr Trp Arg Ser Ile Glu Asp Arg Lys Ile
1               5                   10

<210> SEQ ID NO 27
<211> LENGTH: 9
<212> TYPE: PRT
<213> ORGANISM: Homo sapiens

<400> SEQUENCE: 27

Leu Glu Leu Gln Arg Gln Ser Ser Leu
1               5

<210> SEQ ID NO 28
<211> LENGTH: 44
<212> TYPE: PRT
<213> ORGANISM: Homo sapiens

<400> SEQUENCE: 28

Leu Glu Pro Ser Phe Ser Ala Asn Tyr His Lys Asp Lys Lys Thr Pro
1               5                   10                  15

His Val Leu Thr His Arg Trp Glu Leu Asn Asn Glu Asn Thr Trp Thr
            20                  25                  30

Gln Glu Glu Glu Gln His Thr Leu Gly Pro Val Leu
        35                  40

<210> SEQ ID NO 29
<211> LENGTH: 16
<212> TYPE: PRT
<213> ORGANISM: Homo sapiens

<400> SEQUENCE: 29

Leu Ile Phe Arg Gly Asn Gly Gln Gly Met Arg Glu Gly Asn Lys Lys
1               5                   10                  15

<210> SEQ ID NO 30
<211> LENGTH: 11
<212> TYPE: PRT
<213> ORGANISM: Homo sapiens

<400> SEQUENCE: 30

Leu Leu Leu Lys Leu Glu Pro Ile Ser Gln Gln
1               5                   10

<210> SEQ ID NO 31
<211> LENGTH: 29
<212> TYPE: PRT
<213> ORGANISM: Homo sapiens

<400> SEQUENCE: 31

Leu Arg Gln Glu Asp Cys Leu Asn Pro Gly Gly Arg Gly Cys Ser Glu
1               5                   10                  15

Pro Arg Ser Cys His Cys Thr Pro Ala Trp Ala Thr Glu
            20                  25

<210> SEQ ID NO 32

-continued

```
<211> LENGTH: 9
<212> TYPE: PRT
<213> ORGANISM: Homo sapiens

<400> SEQUENCE: 32

Leu Arg Ser His Ala Trp Trp Trp Thr
1               5

<210> SEQ ID NO 33
<211> LENGTH: 6
<212> TYPE: PRT
<213> ORGANISM: Homo sapiens

<400> SEQUENCE: 33

Leu Ser Ile Ser Cys Leu
1               5

<210> SEQ ID NO 34
<211> LENGTH: 8
<212> TYPE: PRT
<213> ORGANISM: Homo sapiens

<400> SEQUENCE: 34

Met Val Leu Val Asn Leu Lys Pro
1               5

<210> SEQ ID NO 35
<211> LENGTH: 15
<212> TYPE: PRT
<213> ORGANISM: Homo sapiens

<400> SEQUENCE: 35

Asn Lys Thr Pro Ser Val Pro His Asn His Phe Ser Leu Ile Lys
1               5                   10                  15

<210> SEQ ID NO 36
<211> LENGTH: 45
<212> TYPE: PRT
<213> ORGANISM: Homo sapiens

<400> SEQUENCE: 36

Asn Ser Cys Ile Leu Lys Glu Asp Lys Asp Ile Leu Lys Lys Pro Leu
1               5                   10                  15

Asn Ser Arg Phe Ser Ser Asn Ser Lys Val Lys Asn Met Arg Leu Leu
                20                  25                  30

Glu His Ser Thr Phe Ser Ala Pro Leu Asn Arg Val Met
            35                  40                  45

<210> SEQ ID NO 37
<211> LENGTH: 10
<212> TYPE: PRT
<213> ORGANISM: Homo sapiens

<400> SEQUENCE: 37

Asn Ser Asp Phe Tyr Asp Phe Phe His Lys
1               5                   10

<210> SEQ ID NO 38
<211> LENGTH: 8
<212> TYPE: PRT
<213> ORGANISM: Homo sapiens

<400> SEQUENCE: 38

Asn Ser Glu Gly Arg Leu Leu Ser
```

```
<210> SEQ ID NO 39
<211> LENGTH: 33
<212> TYPE: PRT
<213> ORGANISM: Homo sapiens

<400> SEQUENCE: 39

Asn Ser Phe Asp Leu Val Gly Thr Gly Gly Leu Glu Glu Ser Arg Leu
1               5                   10                  15

Ser Ile Pro Trp Pro Leu Gly Ser Leu Leu Tyr Ala Lys Ser Pro Arg
            20                  25                  30

Lys

<210> SEQ ID NO 40
<211> LENGTH: 6
<212> TYPE: PRT
<213> ORGANISM: Homo sapiens

<400> SEQUENCE: 40

Asn Ser Lys Glu Ser Ile
1               5

<210> SEQ ID NO 41
<211> LENGTH: 23
<212> TYPE: PRT
<213> ORGANISM: Homo sapiens

<400> SEQUENCE: 41

Asn Ser Lys Asn Thr Val Leu Gln Leu Asp Ser Val Arg Ser Met Ser
1               5                   10                  15

Glu Ser Arg Ala Ile Thr Thr
            20

<210> SEQ ID NO 42
<211> LENGTH: 26
<212> TYPE: PRT
<213> ORGANISM: Homo sapiens

<400> SEQUENCE: 42

Asn Ser Leu Pro Gly Leu Pro Ser Leu Tyr Phe Val Ser Met Ala Lys
1               5                   10                  15

His Lys Asn Asn Thr Ser Thr Thr Ile Ser
            20                  25

<210> SEQ ID NO 43
<211> LENGTH: 15
<212> TYPE: PRT
<213> ORGANISM: Homo sapiens

<400> SEQUENCE: 43

Asn Ser Pro Asn Thr Leu Phe Arg Ser Ala Ser Thr Lys Pro Lys
1               5                   10                  15

<210> SEQ ID NO 44
<211> LENGTH: 23
<212> TYPE: PRT
<213> ORGANISM: Homo sapiens

<400> SEQUENCE: 44

Asn Ser Gln Glu Cys Leu Ser Gln Ile Leu Leu Ile Pro Ser Ser Cys
1               5                   10                  15
```

-continued

```
Leu Lys Lys Asn Ile Cys Val
            20

<210> SEQ ID NO 45
<211> LENGTH: 8
<212> TYPE: PRT
<213> ORGANISM: Homo sapiens

<400> SEQUENCE: 45

Asn Ser Arg Leu Arg Gly Ile Leu
1               5

<210> SEQ ID NO 46
<211> LENGTH: 36
<212> TYPE: PRT
<213> ORGANISM: Homo sapiens

<400> SEQUENCE: 46

Asn Ser Val Phe Leu Pro Phe Ile Asn Met Phe Ile Arg Lys Trp Tyr
1               5                   10                  15

His Ser Glu His Ile Ser Tyr Ile Leu Phe Phe Phe Cys Val Trp Ile
            20                  25                  30

Phe Thr Leu Arg
        35

<210> SEQ ID NO 47
<211> LENGTH: 7
<212> TYPE: PRT
<213> ORGANISM: Homo sapiens

<400> SEQUENCE: 47

Asn Val Thr Arg Val Phe Lys
1               5

<210> SEQ ID NO 48
<211> LENGTH: 17
<212> TYPE: PRT
<213> ORGANISM: Homo sapiens

<400> SEQUENCE: 48

Pro Ala Ser Thr Leu Lys Gly Gln Asp Ala Arg Asn Arg Leu Thr Gln
1               5                   10                  15

Lys

<210> SEQ ID NO 49
<211> LENGTH: 44
<212> TYPE: PRT
<213> ORGANISM: Homo sapiens

<400> SEQUENCE: 49

Pro Ile His Met Cys Tyr Thr Gly Ala Lys Lys Glu Gly Cys Phe Val
1               5                   10                  15

Gly Lys Ser Ser Glu Glu Val Pro Arg Thr Trp Leu Leu Ser Leu Lys
            20                  25                  30

Gly Asp Gly Val Asn Ser Pro Cys Trp Gly Ser Tyr
        35                  40

<210> SEQ ID NO 50
<211> LENGTH: 21
<212> TYPE: PRT
<213> ORGANISM: Homo sapiens

<400> SEQUENCE: 50
```

```
Pro Gln Ile Ala Ser His Ser Leu Phe Leu Leu Pro Arg Val Leu Ser
1               5                   10                  15

Thr Ser Ile Ile Ser
            20
```

<210> SEQ ID NO 51
<211> LENGTH: 13
<212> TYPE: PRT
<213> ORGANISM: Homo sapiens

<400> SEQUENCE: 51

```
Pro Gln Met Thr Lys Thr Lys Arg Thr His Lys Asn Ile
1               5                   10
```

<210> SEQ ID NO 52
<211> LENGTH: 6
<212> TYPE: PRT
<213> ORGANISM: Homo sapiens

<400> SEQUENCE: 52

```
Gln Ala Tyr Val Asn Val
1               5
```

<210> SEQ ID NO 53
<211> LENGTH: 47
<212> TYPE: PRT
<213> ORGANISM: Homo sapiens

<400> SEQUENCE: 53

```
Gln Glu Ala Ser Val Ser Gly Leu Lys Met Lys Ser Met Ser Thr Lys
1               5                   10                  15

Gln Val Trp Asn Gln Ile Ala Phe Asp Glu Lys Gly Ser Gly Phe Trp
            20                  25                  30

Arg Leu Tyr Phe Arg Cys Cys Tyr Asn Ala Ser Ser Asn Gln Asp
        35                  40                  45
```

<210> SEQ ID NO 54
<211> LENGTH: 13
<212> TYPE: PRT
<213> ORGANISM: Homo sapiens

<400> SEQUENCE: 54

```
Gln Thr Cys Lys Gln Leu Gln Phe Leu Pro Phe Ala Ser
1               5                   10
```

<210> SEQ ID NO 55
<211> LENGTH: 24
<212> TYPE: PRT
<213> ORGANISM: Homo sapiens

<400> SEQUENCE: 55

```
Arg Met Thr Tyr Leu Trp Gly Leu Asn His Lys Pro Thr Asp Asn Val
1               5                   10                  15

Asn Cys His Ser Gln Phe Leu Pro
            20
```

<210> SEQ ID NO 56
<211> LENGTH: 16
<212> TYPE: PRT
<213> ORGANISM: Homo sapiens

<400> SEQUENCE: 56

```
Arg Ser Gln Phe Gln Gln Gly Asn Val Pro Val Gln Ser Arg Leu Arg
1               5                   10                  15
```

<210> SEQ ID NO 57
<211> LENGTH: 16
<212> TYPE: PRT
<213> ORGANISM: Homo sapiens

<400> SEQUENCE: 57

```
Arg Val Thr Pro Thr Ala Glu Gln Ser Pro Ile Pro Gly Cys Arg Lys
1               5                   10                  15
```

<210> SEQ ID NO 58
<211> LENGTH: 26
<212> TYPE: PRT
<213> ORGANISM: Homo sapiens

<400> SEQUENCE: 58

```
Val Cys Ser Ser Ser Ile His Arg Ser Pro Gln Val Glu Arg Val Ser
1               5                   10                  15

Pro Pro His His Phe Pro Glu Glu Gln Thr
            20                  25
```

<210> SEQ ID NO 59
<211> LENGTH: 11
<212> TYPE: PRT
<213> ORGANISM: Homo sapiens

<400> SEQUENCE: 59

```
Val Glu Ser Ala Ser Leu His Leu Asp Cys Phe
1               5                   10
```

<210> SEQ ID NO 60
<211> LENGTH: 16
<212> TYPE: PRT
<213> ORGANISM: Homo sapiens

<400> SEQUENCE: 60

```
Val Gly Gly Gly Arg Ala Ser Gly Arg Ile Ala Asn Gly Cys Trp Ala
1               5                   10                  15
```

<210> SEQ ID NO 61
<211> LENGTH: 13
<212> TYPE: PRT
<213> ORGANISM: Homo sapiens

<400> SEQUENCE: 61

```
Val Pro Ile Gln Met Pro Pro Glu Ala Thr Cys Val Thr
1               5                   10
```

<210> SEQ ID NO 62
<211> LENGTH: 7
<212> TYPE: PRT
<213> ORGANISM: Homo sapiens

<400> SEQUENCE: 62

```
Val Ser Asn Ser Met Lys Ile
1               5
```

<210> SEQ ID NO 63
<211> LENGTH: 22
<212> TYPE: PRT
<213> ORGANISM: Homo sapiens

<400> SEQUENCE: 63

Val Val Ser Gly Ser Gly His Leu Glu Arg Ser Gln Asp Cys Gly Glu
1               5                   10                  15

Lys Gly Asn Ile Phe Gln
            20

<210> SEQ ID NO 64
<211> LENGTH: 16
<212> TYPE: PRT
<213> ORGANISM: Homo sapiens

<400> SEQUENCE: 64

Ala His Ser Pro Thr Lys Gly Cys Gln Ile Cys Gln Asp Gln Glu Lys
1               5                   10                  15

<210> SEQ ID NO 65
<211> LENGTH: 10
<212> TYPE: PRT
<213> ORGANISM: Homo sapiens

<400> SEQUENCE: 65

Ala His Ser Arg Arg Lys Thr Ala Gly Asn
1               5                   10

<210> SEQ ID NO 66
<211> LENGTH: 16
<212> TYPE: PRT
<213> ORGANISM: Homo sapiens

<400> SEQUENCE: 66

Glu His Ile Pro Ala Pro Ala Ser Pro Arg Phe Ser Ile Gln Gly Ser
1               5                   10                  15

<210> SEQ ID NO 67
<211> LENGTH: 8
<212> TYPE: PRT
<213> ORGANISM: Homo sapiens

<400> SEQUENCE: 67

Gly Asn Arg Asp Pro Val Ala Cys
1               5

<210> SEQ ID NO 68
<211> LENGTH: 19
<212> TYPE: PRT
<213> ORGANISM: Homo sapiens

<400> SEQUENCE: 68

Gly Pro Trp His Gln Met Pro Ser Pro Thr Lys Gly Trp Leu Gly Arg
1               5                   10                  15

Ile Ser Gln

<210> SEQ ID NO 69
<211> LENGTH: 9
<212> TYPE: PRT
<213> ORGANISM: Homo sapiens

<400> SEQUENCE: 69

Ile Ala His Ser Gly Ser Ser Val Phe
1               5

<210> SEQ ID NO 70
<211> LENGTH: 12
<212> TYPE: PRT

```
<213> ORGANISM: Homo sapiens

<400> SEQUENCE: 70

Ile Gln Cys Val Tyr Lys Pro Asn Ser His Phe Val
1               5                   10

<210> SEQ ID NO 71
<211> LENGTH: 27
<212> TYPE: PRT
<213> ORGANISM: Homo sapiens

<400> SEQUENCE: 71

Ile Tyr Ile Ser Leu Asn Val Val Thr Leu Lys Ala Cys Thr Leu Lys
1               5                   10                  15

Phe Gly Cys Ile Asn Ala Thr Phe Asn Leu Asn
            20                  25

<210> SEQ ID NO 72
<211> LENGTH: 19
<212> TYPE: PRT
<213> ORGANISM: Homo sapiens

<400> SEQUENCE: 72

Leu Phe Tyr Gly Gly Met Gly Gly Trp Lys Asn Gly Ser Arg Ala Ser
1               5                   10                  15

Glu Ala Asp

<210> SEQ ID NO 73
<211> LENGTH: 23
<212> TYPE: PRT
<213> ORGANISM: Homo sapiens

<400> SEQUENCE: 73

Leu Leu Gln Arg Asn Thr Val Pro Gln Lys Gln Arg Asn Lys Ala Gly
1               5                   10                  15

Trp Arg Met Thr Leu Thr Ser
            20

<210> SEQ ID NO 74
<211> LENGTH: 47
<212> TYPE: PRT
<213> ORGANISM: Homo sapiens

<400> SEQUENCE: 74

Leu Pro Ser Val Ala Arg Arg Ser Pro Gly Leu Gly Pro Gln Leu Arg
1               5                   10                  15

Gln Gln Gly Gly Cys Gly Pro Val Cys His His His Gln Asp Ile Pro
            20                  25                  30

Pro Pro Gln Gly Leu Pro Phe Pro Leu Ala Pro Ser Pro Phe Leu
        35                  40                  45

<210> SEQ ID NO 75
<211> LENGTH: 20
<212> TYPE: PRT
<213> ORGANISM: Homo sapiens

<400> SEQUENCE: 75

Asn Ser Ala Leu Gly Asn His Gly Glu Gly Lys Pro Ile Val Glu Cys
1               5                   10                  15

Leu Leu Arg Cys
            20
```

```
<210> SEQ ID NO 76
<211> LENGTH: 10
<212> TYPE: PRT
<213> ORGANISM: Homo sapiens

<400> SEQUENCE: 76

Asn Ser Ala Ser Ser Lys Cys Pro Ser Tyr
1               5                   10

<210> SEQ ID NO 77
<211> LENGTH: 8
<212> TYPE: PRT
<213> ORGANISM: Homo sapiens

<400> SEQUENCE: 77

Asn Ser Phe Lys Ala Ile Arg Lys
1               5

<210> SEQ ID NO 78
<211> LENGTH: 11
<212> TYPE: PRT
<213> ORGANISM: Homo sapiens

<400> SEQUENCE: 78

Asn Ser Phe Leu Glu Gly Glu Glu Gln Ile Leu
1               5                   10

<210> SEQ ID NO 79
<211> LENGTH: 19
<212> TYPE: PRT
<213> ORGANISM: Homo sapiens

<400> SEQUENCE: 79

Asn Ser Ser Val Thr Leu Met Arg Gln Arg Val Thr Met Met Gly Arg
1               5                   10                  15

His Thr Thr

<210> SEQ ID NO 80
<211> LENGTH: 17
<212> TYPE: PRT
<213> ORGANISM: Homo sapiens

<400> SEQUENCE: 80

Pro Asp Trp Asp Ala Val Val Gln Ser Trp Leu Thr Ala Ala Ser Asn
1               5                   10                  15

Ser

<210> SEQ ID NO 81
<211> LENGTH: 26
<212> TYPE: PRT
<213> ORGANISM: Homo sapiens

<400> SEQUENCE: 81

Pro Arg Arg Thr Gly Glu Gly Ala Pro Pro Ala Arg Leu Ala Arg Arg
1               5                   10                  15

Ala Gly Glu Val Glu His Glu Arg Thr Cys
            20                  25

<210> SEQ ID NO 82
<211> LENGTH: 12
<212> TYPE: PRT
<213> ORGANISM: Homo sapiens
```

```
<400> SEQUENCE: 82

Ser Lys Leu Ser Lys Gly Tyr Glu Lys Leu Val Phe
1               5                   10

<210> SEQ ID NO 83
<211> LENGTH: 11
<212> TYPE: PRT
<213> ORGANISM: Homo sapiens

<400> SEQUENCE: 83

Thr Met Pro Lys Gly Asn Val Lys Leu Gly Asn
1               5                   10

<210> SEQ ID NO 84
<211> LENGTH: 7
<212> TYPE: PRT
<213> ORGANISM: Homo sapiens

<400> SEQUENCE: 84

Val Ile Thr Leu Ile Tyr Arg
1               5

<210> SEQ ID NO 85
<211> LENGTH: 86
<212> TYPE: PRT
<213> ORGANISM: Homo sapiens

<400> SEQUENCE: 85

Gly Pro Glu Gly Ser Glu Ala Val Gln Ser Gly Thr Pro Glu Glu Pro
1               5                   10                  15

Glu Pro Glu Leu Glu Ala Glu Ala Ser Lys Glu Ala Glu Pro Glu Pro
                20                  25                  30

Glu Pro Glu Pro Glu Leu Glu Pro Glu Ala Glu Ala Glu Pro Glu Pro
            35                  40                  45

Glu Leu Glu Pro Glu Pro Asp Pro Glu Pro Glu Pro Asp Phe Glu Glu
        50                  55                  60

Arg Asp Glu Ser Glu Gly Ile Pro Glu Gly Gln Ser Ser Asp Arg Arg
65                  70                  75                  80

Cys Pro Ala His Ala Gly
                85

<210> SEQ ID NO 86
<211> LENGTH: 10
<212> TYPE: PRT
<213> ORGANISM: Homo sapiens

<400> SEQUENCE: 86

Pro Gln Cys Arg Glu Lys Thr Lys Phe Asn
1               5                   10

<210> SEQ ID NO 87
<211> LENGTH: 16
<212> TYPE: PRT
<213> ORGANISM: Homo sapiens

<400> SEQUENCE: 87

Ser Gly Met Pro Arg Arg Tyr Ser Asp Tyr Pro Asp Ala Tyr Thr Thr
1               5                   10                  15

<210> SEQ ID NO 88
<211> LENGTH: 12
<212> TYPE: PRT
```

-continued

<213> ORGANISM: Homo sapiens

<400> SEQUENCE: 88

Asp Val Arg Val Ser Ile His Lys His Ile Leu Gly
1               5                   10

<210> SEQ ID NO 89
<211> LENGTH: 10
<212> TYPE: PRT
<213> ORGANISM: Homo sapiens

<400> SEQUENCE: 89

Gly Lys Arg Arg Asp Ser Phe Phe Ser Phe
1               5                   10

<210> SEQ ID NO 90
<211> LENGTH: 26
<212> TYPE: PRT
<213> ORGANISM: Homo sapiens

<400> SEQUENCE: 90

Leu Glu Thr Ile Ile Leu Ser Lys Leu Ala Gln Glu Gln Lys Thr Lys
1               5                   10                  15

His Arg Met Phe Ser Leu Ile Ser Gly Ser
            20                  25

<210> SEQ ID NO 91
<211> LENGTH: 10
<212> TYPE: PRT
<213> ORGANISM: Homo sapiens

<400> SEQUENCE: 91

Asn Ser Pro Ser Val Gly Leu Phe Thr His
1               5                   10

<210> SEQ ID NO 92
<211> LENGTH: 10
<212> TYPE: PRT
<213> ORGANISM: Homo sapiens

<400> SEQUENCE: 92

Asn Ser Arg Leu Tyr Gln Lys Tyr Lys Asn
1               5                   10

<210> SEQ ID NO 93
<211> LENGTH: 17
<212> TYPE: PRT
<213> ORGANISM: Homo sapiens

<400> SEQUENCE: 93

Pro Ala Arg Leu Ala Arg Arg Ala Gly Glu Val Glu His Glu Arg Thr
1               5                   10                  15

Cys

<210> SEQ ID NO 94
<211> LENGTH: 17
<212> TYPE: PRT
<213> ORGANISM: Homo sapiens

<400> SEQUENCE: 94

Ser Leu Thr Ser Thr Ala Ser Asp Gly Asp Tyr Ser Ala Arg Thr Val
1               5                   10                  15

Met

```
<210> SEQ ID NO 95
<211> LENGTH: 15
<212> TYPE: PRT
<213> ORGANISM: Homo sapiens

<400> SEQUENCE: 95

Thr Gln Ser Pro Thr Thr Leu Asn Val Ala Gly Thr Pro Gln Gln
1               5                   10                  15

<210> SEQ ID NO 96
<211> LENGTH: 31
<212> TYPE: PRT
<213> ORGANISM: Homo sapiens

<400> SEQUENCE: 96

Pro Ser Gln Leu Lys Cys Ser Pro Ser Ala Asn Val Lys Met Gly Gly
1               5                   10                  15

Gly Lys Gly Leu Lys Ile Arg Glu Asn Cys Met His Leu Arg Thr
            20                  25                  30

<210> SEQ ID NO 97
<211> LENGTH: 25
<212> TYPE: PRT
<213> ORGANISM: Homo sapiens

<400> SEQUENCE: 97

Gly Glu Arg Gly Lys Arg Thr Phe Gln Lys Glu Ser Asp Thr Ala Leu
1               5                   10                  15

Ile Leu Arg Glu Cys Pro Ile Cys Leu
            20                  25

<210> SEQ ID NO 98
<211> LENGTH: 25
<212> TYPE: PRT
<213> ORGANISM: Homo sapiens

<400> SEQUENCE: 98

Asn Ser Leu Glu Trp Thr Lys Val Tyr Leu Gly Lys Lys Ile Trp Thr
1               5                   10                  15

Pro Glu Lys Gly Asn Ser Ser Tyr Lys
            20                  25

<210> SEQ ID NO 99
<211> LENGTH: 53
<212> TYPE: PRT
<213> ORGANISM: Homo sapiens

<400> SEQUENCE: 99

Arg Pro Gln Thr Asp Arg Pro Gln Asp Arg Arg Pro Arg His Ala
1               5                   10                  15

Pro Cys Pro Gln Glu Gly Cys Val Pro Leu Glu Ser Asn Ala Gly Arg
            20                  25                  30

Pro His Asn Leu Leu Ser Asp Tyr Ser Cys Asp Lys Ser Pro Gly Arg
                35                  40                  45

Ser Met Thr Arg Gly
        50

<210> SEQ ID NO 100
<211> LENGTH: 14
<212> TYPE: PRT
<213> ORGANISM: Homo sapiens
```

```
<400> SEQUENCE: 100

Gly Gln Gln Arg Lys Pro Cys Leu Gly Gly Lys Lys Thr
1               5                   10

<210> SEQ ID NO 101
<211> LENGTH: 56
<212> TYPE: PRT
<213> ORGANISM: Homo sapiens

<400> SEQUENCE: 101

Asn Ser Thr Ala Thr Thr Ser Ser Ser Leu Lys Asp Pro Gly Ser
1               5                   10                  15

Arg Arg Pro Ser Trp Thr Ser Leu Ala Lys Glu Arg Ser Gln Glu Gln
            20                  25                  30

Ala Lys Arg Asn Leu Glu Phe Gln Ser Pro Thr Leu Ser Pro Pro Met
        35                  40                  45

Lys Ala Thr Leu Ser Lys Pro Ser
    50                  55

<210> SEQ ID NO 102
<211> LENGTH: 5
<212> TYPE: PRT
<213> ORGANISM: Homo sapiens

<400> SEQUENCE: 102

Pro Cys Ser Lys His
1               5

<210> SEQ ID NO 103
<211> LENGTH: 37
<212> TYPE: PRT
<213> ORGANISM: Homo sapiens

<400> SEQUENCE: 103

Gln Glu Arg Pro Ser Glu Thr Ile Asp Arg Glu Arg Lys Arg Leu Val
1               5                   10                  15

Glu Thr Leu Gln Ala Asp Ser Gly Glu Pro Asp Phe Glu Glu Arg Asp
            20                  25                  30

Glu Ser Glu Asp Ser
        35

<210> SEQ ID NO 104
<211> LENGTH: 25
<212> TYPE: PRT
<213> ORGANISM: Homo sapiens

<400> SEQUENCE: 104

Arg Ile Cys Pro Thr His Thr Lys Pro Gln Asn Thr Val Pro Leu His
1               5                   10                  15

Leu Leu Arg Pro Thr Ile Asp Gln Leu
            20                  25

<210> SEQ ID NO 105
<211> LENGTH: 12
<212> TYPE: PRT
<213> ORGANISM: Homo sapiens

<400> SEQUENCE: 105

Trp Val Ser Glu Pro His Cys Val Val Val Asn Met
1               5                   10
```

```
<210> SEQ ID NO 106
<211> LENGTH: 19
<212> TYPE: PRT
<213> ORGANISM: Homo sapiens

<400> SEQUENCE: 106

Gly Ala Gly Thr Gly Ala Arg Ala Arg Ala Arg Ala Gly Ala Ala Leu
1               5                   10                  15

Thr Trp Ser

<210> SEQ ID NO 107
<211> LENGTH: 28
<212> TYPE: PRT
<213> ORGANISM: Homo sapiens

<400> SEQUENCE: 107

Ile Leu Leu Met Arg Arg Met Thr Arg Met Ser Gly Gly Ala Glu
1               5                   10                  15

Gln Thr Gln Thr Met Gln Met Gly Val Lys Thr Lys
            20                  25

<210> SEQ ID NO 108
<211> LENGTH: 19
<212> TYPE: PRT
<213> ORGANISM: Homo sapiens

<400> SEQUENCE: 108

Leu His His Ile Gly Gln Gln His Pro Gln Arg Phe Trp His Gln Arg
1               5                   10                  15

Pro Ile Ser

<210> SEQ ID NO 109
<211> LENGTH: 27
<212> TYPE: PRT
<213> ORGANISM: Homo sapiens

<400> SEQUENCE: 109

Leu Met Arg Val Leu Lys Thr Glu Val Thr Gly Tyr Gln Glu Val Cys
1               5                   10                  15

Thr Pro Lys Arg Asn Trp Asn Ser Arg Gln Glu
            20                  25

<210> SEQ ID NO 110
<211> LENGTH: 12
<212> TYPE: PRT
<213> ORGANISM: Homo sapiens

<400> SEQUENCE: 110

Asn Ser Leu Ile Gln His Gln His Leu Gly Gln Ile
1               5                   10

<210> SEQ ID NO 111
<211> LENGTH: 18
<212> TYPE: PRT
<213> ORGANISM: Homo sapiens

<400> SEQUENCE: 111

Asn Ser Gln Gly Leu Asp Phe Ser Lys Ala Thr Leu Arg Ser Arg Gln
1               5                   10                  15

Arg Leu
```

-continued

<210> SEQ ID NO 112
<211> LENGTH: 36
<212> TYPE: PRT
<213> ORGANISM: Homo sapiens

<400> SEQUENCE: 112

Asn Ser Ser Asp Ser Leu Arg Ile Val Trp Leu Leu Ser Asp Val Tyr
1               5                   10                  15

Glu Ser Phe Leu His Leu Pro Phe Gln Ile Ser His Cys Ser Trp Tyr
            20                  25                  30

Lys Tyr Leu Ser
        35

<210> SEQ ID NO 113
<211> LENGTH: 12
<212> TYPE: PRT
<213> ORGANISM: Homo sapiens

<400> SEQUENCE: 113

Asn Ser Ser Pro Ala Asp Leu Pro Cys Arg Ile Cys
1               5                   10

<210> SEQ ID NO 114
<211> LENGTH: 31
<212> TYPE: PRT
<213> ORGANISM: Homo sapiens

<400> SEQUENCE: 114

Arg Thr Pro Ser Ser Pro Cys Trp Pro Pro Gly Pro Val Leu Ala Glu
1               5                   10                  15

Glu Pro Glu Pro Asp Phe Glu Glu Arg Asp Glu Ser Glu Asp Ser
            20                  25                  30

<210> SEQ ID NO 115
<211> LENGTH: 28
<212> TYPE: PRT
<213> ORGANISM: Homo sapiens

<400> SEQUENCE: 115

Arg Val Pro Lys Gln Arg Tyr Arg Ser Met Glu Gln Asn Arg Ala Leu
1               5                   10                  15

Arg Asn Asn Ala Val Tyr Leu Gln Leu Ser Asp Leu
            20                  25

<210> SEQ ID NO 116
<211> LENGTH: 17
<212> TYPE: PRT
<213> ORGANISM: Homo sapiens

<400> SEQUENCE: 116

Ser Thr Lys Lys Met Gly Thr Gln Ala Leu Ser Lys Ala Ala Pro His
1               5                   10                  15

Cys

<210> SEQ ID NO 117
<211> LENGTH: 30
<212> TYPE: PRT
<213> ORGANISM: Homo sapiens

<400> SEQUENCE: 117

Thr Arg Ser Gly Ser Ser Ser Trp Ala Val Leu Thr Gly Ala Arg Pro
1               5                   10                  15

```
Lys Arg Leu Cys Ala Ala Thr Phe Pro Asn Met Glu Lys Ser
             20                  25                  30
```

<210> SEQ ID NO 118
<211> LENGTH: 13
<212> TYPE: PRT
<213> ORGANISM: Homo sapiens

<400> SEQUENCE: 118

```
Ala Glu Glu Tyr Arg Leu Gln Arg His Tyr Cys Ser Tyr
1               5                   10
```

<210> SEQ ID NO 119
<211> LENGTH: 25
<212> TYPE: PRT
<213> ORGANISM: Homo sapiens

<400> SEQUENCE: 119

```
Ala Glu Ser Thr Pro Val Gln Asp Pro Ser Ile Phe Cys Glu Tyr Ser
1               5                   10                  15

Thr Pro Thr Ser Met Gly Gly Gly Lys
             20                  25
```

<210> SEQ ID NO 120
<211> LENGTH: 10
<212> TYPE: PRT
<213> ORGANISM: Homo sapiens

<400> SEQUENCE: 120

```
Ala Glu Val Pro Ile Leu Phe Ile Pro Pro
1               5                   10
```

<210> SEQ ID NO 121
<211> LENGTH: 30
<212> TYPE: PRT
<213> ORGANISM: Homo sapiens

<400> SEQUENCE: 121

```
Ala Gly Gly Ser Phe Ser Pro Trp Pro Val Leu Leu Pro Pro Pro
1               5                   10                  15

Pro Gly Gly Lys Ser Gly His Asn Arg Gly Gln Arg Pro His
             20                  25                  30
```

<210> SEQ ID NO 122
<211> LENGTH: 12
<212> TYPE: PRT
<213> ORGANISM: Homo sapiens

<400> SEQUENCE: 122

```
Ala His Ile Arg Thr Lys Asp Ser Ile Asn Cys Ile
1               5                   10
```

<210> SEQ ID NO 123
<211> LENGTH: 6
<212> TYPE: PRT
<213> ORGANISM: Homo sapiens

<400> SEQUENCE: 123

```
Ala Ile Cys Ser Ile Leu
1               5
```

<210> SEQ ID NO 124
<211> LENGTH: 10
<212> TYPE: PRT

```
<213> ORGANISM: Homo sapiens

<400> SEQUENCE: 124

Ala Ile Gly Lys Ile Ala Lys Asn Asn Pro
1               5                   10

<210> SEQ ID NO 125
<211> LENGTH: 18
<212> TYPE: PRT
<213> ORGANISM: Homo sapiens

<400> SEQUENCE: 125

Ala Asn Asn Leu Leu Asn Gly Gly Leu Tyr Thr Gly Lys Pro Tyr Cys
1               5                   10                  15

Gly Asn

<210> SEQ ID NO 126
<211> LENGTH: 10
<212> TYPE: PRT
<213> ORGANISM: Homo sapiens

<400> SEQUENCE: 126

Ala Asn Gln Leu Asn Glu Leu Asn Pro Lys
1               5                   10

<210> SEQ ID NO 127
<211> LENGTH: 18
<212> TYPE: PRT
<213> ORGANISM: Homo sapiens

<400> SEQUENCE: 127

Ala Gln Gly Pro Arg Cys Ala Gly Cys Thr Gly Lys Gly Arg Thr Thr
1               5                   10                  15

Ala Gly

<210> SEQ ID NO 128
<211> LENGTH: 35
<212> TYPE: PRT
<213> ORGANISM: Homo sapiens

<400> SEQUENCE: 128

Ala Gln Val Leu Cys His Ile Glu Asp Gln Val Pro Asp Gln Ile Leu
1               5                   10                  15

Pro Gly Val Pro Leu Glu Leu Leu Gly Glu Phe Cys Gln Glu Ser Gly
            20                  25                  30

Arg Arg Lys
        35

<210> SEQ ID NO 129
<211> LENGTH: 26
<212> TYPE: PRT
<213> ORGANISM: Homo sapiens

<400> SEQUENCE: 129

Ala Arg Gly Pro Ser Trp Arg Ser Asn Glu Leu Trp Leu His His Leu
1               5                   10                  15

Ser Ser Ser Ser Arg His Leu Met Ser Ser
            20                  25

<210> SEQ ID NO 130
<211> LENGTH: 14
<212> TYPE: PRT
```

<213> ORGANISM: Homo sapiens

<400> SEQUENCE: 130

Ala Ser Cys Tyr Leu Thr Ser Asn Cys Thr Thr Arg Val Gln
1               5                   10

<210> SEQ ID NO 131
<211> LENGTH: 31
<212> TYPE: PRT
<213> ORGANISM: Homo sapiens

<400> SEQUENCE: 131

Ala Ser Arg Lys Ile Trp Tyr Glu Leu Asn Ser Gly Tyr Ala Glu Trp
1               5                   10                  15

Arg Thr Glu Glu Ala Ile Arg Arg Ser Gly Arg His Gln Val Gln
            20                  25                  30

<210> SEQ ID NO 132
<211> LENGTH: 5
<212> TYPE: PRT
<213> ORGANISM: Homo sapiens

<400> SEQUENCE: 132

Ala Thr Leu Ser Val
1               5

<210> SEQ ID NO 133
<211> LENGTH: 8
<212> TYPE: PRT
<213> ORGANISM: Homo sapiens

<400> SEQUENCE: 133

Ala Val Tyr Phe Phe Lys Ala Lys
1               5

<210> SEQ ID NO 134
<211> LENGTH: 10
<212> TYPE: PRT
<213> ORGANISM: Homo sapiens

<400> SEQUENCE: 134

Ala Trp Tyr Lys Ile Cys Lys Ile Cys Leu
1               5                   10

<210> SEQ ID NO 135
<211> LENGTH: 8
<212> TYPE: PRT
<213> ORGANISM: Homo sapiens

<400> SEQUENCE: 135

Ala Tyr Asn Lys Phe Leu His Leu
1               5

<210> SEQ ID NO 136
<211> LENGTH: 12
<212> TYPE: PRT
<213> ORGANISM: Homo sapiens

<400> SEQUENCE: 136

Cys Trp Pro Gly Trp Ser Gln Thr Pro Asp Leu Arg
1               5                   10

<210> SEQ ID NO 137
<211> LENGTH: 16

```
<212> TYPE: PRT
<213> ORGANISM: Homo sapiens

<400> SEQUENCE: 137

Asp Glu Trp Lys Asn Thr Phe Gln Gly Glu Leu Lys Gly Leu Lys Cys
1               5                   10                  15

<210> SEQ ID NO 138
<211> LENGTH: 10
<212> TYPE: PRT
<213> ORGANISM: Homo sapiens

<400> SEQUENCE: 138

Asp Lys Lys Phe Leu Ile Glu Thr Ser Ile
1               5                   10

<210> SEQ ID NO 139
<211> LENGTH: 26
<212> TYPE: PRT
<213> ORGANISM: Homo sapiens

<400> SEQUENCE: 139

Asp Val Phe Asn Thr Val Gly Pro Leu Gly Trp Ser Val Phe His Pro
1               5                   10                  15

Gln Thr Asn Ala Asp Gln Asn Gly Val Phe
            20                  25

<210> SEQ ID NO 140
<211> LENGTH: 6
<212> TYPE: PRT
<213> ORGANISM: Homo sapiens

<400> SEQUENCE: 140

Glu Cys Gln Gly Gln Cys
1               5

<210> SEQ ID NO 141
<211> LENGTH: 21
<212> TYPE: PRT
<213> ORGANISM: Homo sapiens

<400> SEQUENCE: 141

Glu Glu Glu His Ser Asp Lys Tyr Val Leu Ser Leu Leu Met Asn Ser
1               5                   10                  15

Leu Ser Leu Arg Ser
            20

<210> SEQ ID NO 142
<211> LENGTH: 10
<212> TYPE: PRT
<213> ORGANISM: Homo sapiens

<400> SEQUENCE: 142

Glu Phe Phe Leu Met Thr Ile Gly Lys Asn
1               5                   10

<210> SEQ ID NO 143
<211> LENGTH: 18
<212> TYPE: PRT
<213> ORGANISM: Homo sapiens

<400> SEQUENCE: 143

Glu Lys Glu Lys Asn Leu Asn Cys Phe Phe Gly Arg Thr Thr Thr Lys
1               5                   10                  15
```

```
Lys Arg

<210> SEQ ID NO 144
<211> LENGTH: 25
<212> TYPE: PRT
<213> ORGANISM: Homo sapiens

<400> SEQUENCE: 144

Glu Lys Leu Ala Thr Ser Met Tyr Leu Gln Asn Pro Asn Trp Arg Leu
1               5                   10                  15
Ser Ser Glu Ser Glu Val Ser Met Glu
            20                  25

<210> SEQ ID NO 145
<211> LENGTH: 28
<212> TYPE: PRT

<213> ORGANISM: Homo sapiens

<400> SEQUENCE: 145

Glu Leu Glu Ser Cys Cys Val Thr Gln Ala Gly Val Pro Cys Tyr Asp
1               5                   10                  15

Leu Cys Ser Leu Gln Pro Pro Ser Pro Gly Phe Lys
            20                  25

<210> SEQ ID NO 146
<211> LENGTH: 5
<212> TYPE: PRT
<213> ORGANISM: Homo sapiens

<400> SEQUENCE: 146

Glu Leu Leu Phe Leu
1               5

<210> SEQ ID NO 147
<211> LENGTH: 11
<212> TYPE: PRT
<213> ORGANISM: Homo sapiens

<400> SEQUENCE: 147

Glu Met Leu Asn Gly Gly Arg Val Leu Trp Met
1               5                   10

<210> SEQ ID NO 148
<211> LENGTH: 5
<212> TYPE: PRT
<213> ORGANISM: Homo sapiens

<400> SEQUENCE: 148

Glu Gln Leu Gln Thr
1               5

<210> SEQ ID NO 149
<211> LENGTH: 5
<212> TYPE: PRT
<213> ORGANISM: Homo sapiens

<400> SEQUENCE: 149

Glu Arg Lys Val Phe
1               5

<210> SEQ ID NO 150
<211> LENGTH: 7
<212> TYPE: PRT
```

<210> SEQ ID NO 150
<211> LENGTH: 7 (?)
<212> TYPE: PRT
<213> ORGANISM: Homo sapiens

<400> SEQUENCE: 150

Glu Thr Ser Ile Lys Tyr Thr
1               5

<210> SEQ ID NO 151
<211> LENGTH: 21
<212> TYPE: PRT
<213> ORGANISM: Homo sapiens

<400> SEQUENCE: 151

Gly Ala Gly Lys Phe Leu Arg Glu Lys Glu Lys Glu Ile Ser Leu Gly
1               5                   10                  15

Leu Met Leu Gly Lys
            20

<210> SEQ ID NO 152
<211> LENGTH: 4
<212> TYPE: PRT
<213> ORGANISM: Homo sapiens

<400> SEQUENCE: 152

Gly Cys Leu Gly
1

<210> SEQ ID NO 153
<211> LENGTH: 9
<212> TYPE: PRT
<213> ORGANISM: Homo sapiens

<400> SEQUENCE: 153

Gly Cys Leu Gly Phe Trp Gly Arg Gly
1               5

<210> SEQ ID NO 154
<211> LENGTH: 11
<212> TYPE: PRT
<213> ORGANISM: Homo sapiens

<400> SEQUENCE: 154

Gly Glu Ala Cys Leu Ser Thr Ala Thr Ser Trp
1               5                   10

<210> SEQ ID NO 155
<211> LENGTH: 39
<212> TYPE: PRT
<213> ORGANISM: Homo sapiens

<400> SEQUENCE: 155

Gly Phe Leu Thr Met Glu Arg Lys Lys Ile Thr Pro Pro Thr Thr Lys
1               5                   10                  15

Thr Tyr Ile Ser Thr Leu Pro Thr Asp Ser Ile Lys Gln Leu Arg Asn
            20                  25                  30

Gly Asp Tyr Lys Ala Thr Ser
        35

<210> SEQ ID NO 156
<211> LENGTH: 34
<212> TYPE: PRT
<213> ORGANISM: Homo sapiens

<400> SEQUENCE: 156

```
Gly Gly Cys Asp His Cys Arg Asp Thr Thr His Gly Gly Cys Gly His
1               5                   10                  15

Cys Gly Leu Arg Gly Asn Pro Ser Arg Pro Pro Asp Leu Gln Asp Cys
            20                  25                  30

Leu Cys

<210> SEQ ID NO 157
<211> LENGTH: 8
<212> TYPE: PRT
<213> ORGANISM: Homo sapiens

<400> SEQUENCE: 157

Gly Ile Phe Phe Val Ser Lys Ile
1               5

<210> SEQ ID NO 158
<211> LENGTH: 14
<212> TYPE: PRT
<213> ORGANISM: Homo sapiens

<400> SEQUENCE: 158

Gly Ile Gly Asn Val Lys Asp Gly Arg His Gly Glu Ser Phe
1               5                   10

<210> SEQ ID NO 159
<211> LENGTH: 27
<212> TYPE: PRT
<213> ORGANISM: Homo sapiens

<400> SEQUENCE: 159

Gly Ile Ser Pro Thr Lys Glu Asp Val Ile His Ser Asp Val Gln Asp
1               5                   10                  15

Glu Leu Val His Ser Ala Cys Tyr Val Cys Ile
            20                  25

<210> SEQ ID NO 160
<211> LENGTH: 7
<212> TYPE: PRT
<213> ORGANISM: Homo sapiens

<400> SEQUENCE: 160

Gly Lys His Glu Gly Glu Gly
1               5

<210> SEQ ID NO 161
<211> LENGTH: 27
<212> TYPE: PRT
<213> ORGANISM: Homo sapiens

<400> SEQUENCE: 161

Gly Lys Ile Asp Glu Arg Gly Arg Gln Gly Gly Arg Glu Arg Asp Arg
1               5                   10                  15

Asn Arg Asp Arg Glu Arg Gln Arg Glu Arg Glu
            20                  25

<210> SEQ ID NO 162
<211> LENGTH: 15
<212> TYPE: PRT
<213> ORGANISM: Homo sapiens

<400> SEQUENCE: 162

Gly Lys Pro Lys Arg His Trp Asp Glu Arg Ala Ala Gly Gly Leu
1               5                   10                  15
```

<210> SEQ ID NO 163
<211> LENGTH: 8
<212> TYPE: PRT
<213> ORGANISM: Homo sapiens

<400> SEQUENCE: 163

Gly Lys Pro Thr Pro Leu Ile Gln
1               5

<210> SEQ ID NO 164
<211> LENGTH: 36
<212> TYPE: PRT
<213> ORGANISM: Homo sapiens
<220> FEATURE:
<221> NAME/KEY: misc_feature
<222> LOCATION: (23)..(23)
<223> OTHER INFORMATION: Xaa can be any naturally occurring amino acid

<400> SEQUENCE: 164

Gly Lys Val Lys Glu Leu Asn Lys Glu Val Arg Glu Lys Lys Gly Lys
1               5                   10                  15

Ile Lys Gln Tyr Asn Thr Xaa Gln Lys Gly Lys Ser Arg Arg Gln
            20                  25                  30

Cys Lys Asn Ser
        35

<210> SEQ ID NO 165
<211> LENGTH: 14
<212> TYPE: PRT
<213> ORGANISM: Homo sapiens

<400> SEQUENCE: 165

Gly Leu Pro Leu Trp Arg Arg Glu Arg Val Lys Val Met Arg
1               5                   10

<210> SEQ ID NO 166
<211> LENGTH: 56
<212> TYPE: PRT
<213> ORGANISM: Homo sapiens

<400> SEQUENCE: 166

Gly Leu Trp Trp Lys Arg Lys Tyr Leu His Leu Asn Thr Arg Glu Lys
1               5                   10                  15

His Ser Gln Lys Leu Leu Cys Asp Asp Cys Ile His Leu Thr Glu Leu
            20                  25                  30

Asn Ile Pro Ile Asp Arg Ala Val Trp Lys His Ser Cys Cys Gly Met
        35                  40                  45

Cys Lys Trp Arg Phe Gly Ala Leu
    50                  55

<210> SEQ ID NO 167
<211> LENGTH: 4
<212> TYPE: PRT
<213> ORGANISM: Homo sapiens

<400> SEQUENCE: 167

Gly Met Ser Thr
1

<210> SEQ ID NO 168
<211> LENGTH: 5
<212> TYPE: PRT

```
<213> ORGANISM: Homo sapiens

<400> SEQUENCE: 168

Gly Asn Tyr Ala Lys
1               5

<210> SEQ ID NO 169
<211> LENGTH: 6
<212> TYPE: PRT
<213> ORGANISM: Homo sapiens

<400> SEQUENCE: 169

Gly Asn Tyr Ala Arg Gln
1               5

<210> SEQ ID NO 170
<211> LENGTH: 36
<212> TYPE: PRT
<213> ORGANISM: Homo sapiens

<400> SEQUENCE: 170

Gly Pro Ala Phe Val Leu Met Lys Pro Gly Ala Ser Pro Tyr Pro Ile
1               5                   10                  15

Leu Ala Leu Thr Leu Ile Thr Asn Gln Met Leu Gln Asn Lys Ser Asn
            20                  25                  30

Asn Asp Pro Asn
        35

<210> SEQ ID NO 171
<211> LENGTH: 52
<212> TYPE: PRT
<213> ORGANISM: Homo sapiens

<400> SEQUENCE: 171

Gly Pro Phe Cys His Gln Arg Ser Gly Asn Pro Arg Ile His His Gln
1               5                   10                  15

His Ser Gln Ala His Pro Trp Ser Gly Leu Gln Glu Ala Cys Thr Ser
            20                  25                  30

Gly Thr Gln Arg Asp Ser Glu Ile Cys His Glu Gly Asp Gly Asn Ser
        35                  40                  45

Arg Cys Ala His
    50

<210> SEQ ID NO 172
<211> LENGTH: 5
<212> TYPE: PRT
<213> ORGANISM: Homo sapiens

<400> SEQUENCE: 172

Gly Pro Thr Ser Asn
1               5

<210> SEQ ID NO 173
<211> LENGTH: 18
<212> TYPE: PRT
<213> ORGANISM: Homo sapiens

<400> SEQUENCE: 173

Gly Gln His Tyr Pro Asn Thr Lys Ala Arg Gln Lys Ile Thr Thr Arg
1               5                   10                  15

Lys Leu
```

```
<210> SEQ ID NO 174
<211> LENGTH: 9
<212> TYPE: PRT
<213> ORGANISM: Homo sapiens

<400> SEQUENCE: 174

Gly Gln Arg Leu Ile Ile Ile Asn Gly
1               5

<210> SEQ ID NO 175
<211> LENGTH: 25
<212> TYPE: PRT
<213> ORGANISM: Homo sapiens

<400> SEQUENCE: 175

Gly Arg Cys Val Val Ala Thr Glu Ile Asn Ser Arg Asn Arg Asp Ser
1               5                   10                  15

Ala Cys Gln Glu Phe Glu Phe Arg Val
            20                  25

<210> SEQ ID NO 176
<211> LENGTH: 17
<212> TYPE: PRT
<213> ORGANISM: Homo sapiens

<400> SEQUENCE: 176

Gly Arg Gly Arg Thr Arg Trp Gly Met Gly Met Leu Leu Lys Lys Ile
1               5                   10                  15

Gln

<210> SEQ ID NO 177
<211> LENGTH: 17
<212> TYPE: PRT
<213> ORGANISM: Homo sapiens

<400> SEQUENCE: 177

Gly Arg Pro Gly Ile Gly Ala Thr His Ser Ser Arg Phe Ile Pro Leu
1               5                   10                  15

Lys

<210> SEQ ID NO 178
<211> LENGTH: 12
<212> TYPE: PRT
<213> ORGANISM: Homo sapiens

<400> SEQUENCE: 178

Gly Arg Val Pro Phe Thr Phe Phe Asn Leu Ser Leu
1               5                   10

<210> SEQ ID NO 179
<211> LENGTH: 28
<212> TYPE: PRT
<213> ORGANISM: Homo sapiens

<400> SEQUENCE: 179

Gly Thr Ser Ser Ser His Asp Pro Leu Ser Arg Leu Pro Lys Leu Asn
1               5                   10                  15

Leu Ser Arg Gly Gly Val Trp Ala Ser Trp Val Lys
            20                  25

<210> SEQ ID NO 180
<211> LENGTH: 49
```

```
<212> TYPE: PRT
<213> ORGANISM: Homo sapiens

<400> SEQUENCE: 180

Gly Val Glu Arg Val Ala Tyr Ser Ile His Pro Ala Ser Pro Thr Ser
1               5                   10                  15

Val Ser His Ser Leu Val Glu Arg Met Ala Met Ala Pro Pro Val Met
                20                  25                  30

Glu Ser Met Arg Ser Pro Pro Gln Ser Thr Arg Pro Arg Val Pro Leu
            35                  40                  45

Ser

<210> SEQ ID NO 181
<211> LENGTH: 7
<212> TYPE: PRT
<213> ORGANISM: Homo sapiens

<400> SEQUENCE: 181

Gly Trp Gly Arg Arg Ile Ala
1               5

<210> SEQ ID NO 182
<211> LENGTH: 9
<212> TYPE: PRT
<213> ORGANISM: Homo sapiens

<400> SEQUENCE: 182

His Cys His Cys Leu Pro Asp Leu Pro
1               5

<210> SEQ ID NO 183
<211> LENGTH: 12
<212> TYPE: PRT
<213> ORGANISM: Homo sapiens

<400> SEQUENCE: 183

His Ile Leu Ser Ser Thr Cys Cys Phe Leu Thr Phe
1               5                   10

<210> SEQ ID NO 184
<211> LENGTH: 21
<212> TYPE: PRT
<213> ORGANISM: Homo sapiens

<400> SEQUENCE: 184

His Leu Trp Ala Gln His His Ser Val Ser Ser Leu Lys Gly Arg Thr
1               5                   10                  15

Thr Leu Glu Tyr Phe
            20

<210> SEQ ID NO 185
<211> LENGTH: 42
<212> TYPE: PRT
<213> ORGANISM: Homo sapiens

<400> SEQUENCE: 185

His Thr Phe Lys Asn Thr Trp Glu Leu Lys Asn Glu Asn Thr Trp Thr
1               5                   10                  15

Gln Gly Gly Glu Tyr His Thr Pro Gly Pro Ala Gly Gly Phe Gly Gly
                20                  25                  30

Lys Gly Arg Glu Ser Ile Arg Thr Lys Ile
            35                  40
```

```
<210> SEQ ID NO 186
<211> LENGTH: 5
<212> TYPE: PRT
<213> ORGANISM: Homo sapiens

<400> SEQUENCE: 186

Ile Ala Ser Tyr Met
1               5

<210> SEQ ID NO 187
<211> LENGTH: 7
<212> TYPE: PRT
<213> ORGANISM: Homo sapiens

<400> SEQUENCE: 187

Ile Asp Leu Lys Ser Asn Leu
1               5

<210> SEQ ID NO 188
<211> LENGTH: 4
<212> TYPE: PRT
<213> ORGANISM: Homo sapiens

<400> SEQUENCE: 188

Ile Phe Arg Asn
1

<210> SEQ ID NO 189
<211> LENGTH: 13
<212> TYPE: PRT
<213> ORGANISM: Homo sapiens

<400> SEQUENCE: 189

Ile Gly Thr Arg Asp Gln Gly Lys Arg Leu Arg Met Lys
1               5                   10

<210> SEQ ID NO 190
<211> LENGTH: 20
<212> TYPE: PRT
<213> ORGANISM: Homo sapiens

<400> SEQUENCE: 190

Ile Leu Leu Gln Gly Tyr Pro Gly Ser Ser Thr Ser Leu Arg Pro
1               5                   10                  15

His Ser Ser Asn
            20

<210> SEQ ID NO 191
<211> LENGTH: 21
<212> TYPE: PRT
<213> ORGANISM: Homo sapiens

<400> SEQUENCE: 191

Ile Asn Gln Lys Tyr Thr Trp Leu Asp Lys Ser His Tyr Ala Leu Thr
1               5                   10                  15

Thr Asn Ala Ser Ser
            20

<210> SEQ ID NO 192
<211> LENGTH: 7
<212> TYPE: PRT
<213> ORGANISM: Homo sapiens
```

```
<400> SEQUENCE: 192

Ile Gln Asn Ser Lys Lys Ser
1               5

<210> SEQ ID NO 193
<211> LENGTH: 26
<212> TYPE: PRT
<213> ORGANISM: Homo sapiens

<400> SEQUENCE: 193

Ile Gln Ser Ala Thr Glu Leu Val Gly Arg Leu Gly Met His Pro Arg
1               5                   10                  15

Ile Gln Ser Ala Thr Glu Leu Val Val Ser
            20                  25

<210> SEQ ID NO 194
<211> LENGTH: 17
<212> TYPE: PRT
<213> ORGANISM: Homo sapiens

<400> SEQUENCE: 194

Ile Arg Ala Ser Asn Gln Tyr Arg Ser Ser Val Lys Tyr Ile Ser Val
1               5                   10                  15

His

<210> SEQ ID NO 195
<211> LENGTH: 9
<212> TYPE: PRT
<213> ORGANISM: Homo sapiens

<400> SEQUENCE: 195

Ile Thr Pro Arg Ala Val Phe Trp Tyr
1               5

<210> SEQ ID NO 196
<211> LENGTH: 8
<212> TYPE: PRT
<213> ORGANISM: Homo sapiens

<400> SEQUENCE: 196

Ile Tyr Phe Lys Lys Lys Lys Thr
1               5

<210> SEQ ID NO 197
<211> LENGTH: 13
<212> TYPE: PRT
<213> ORGANISM: Homo sapiens

<400> SEQUENCE: 197

Lys Asp His Ala Gln Ser Asn Lys Tyr Leu Thr Ser Leu
1               5                   10

<210> SEQ ID NO 198
<211> LENGTH: 13
<212> TYPE: PRT
<213> ORGANISM: Homo sapiens

<400> SEQUENCE: 198

Lys Gly Met Asn Lys Thr Ser Lys Asn Cys Gly Thr Met
1               5                   10

<210> SEQ ID NO 199
<211> LENGTH: 12
```

```
<212> TYPE: PRT
<213> ORGANISM: Homo sapiens

<400> SEQUENCE: 199

Lys Gly Thr Thr Arg Ser Gly Ser Leu Gly Cys Lys
1               5                   10

<210> SEQ ID NO 200
<211> LENGTH: 5
<212> TYPE: PRT
<213> ORGANISM: Homo sapiens

<400> SEQUENCE: 200

Lys Ile Tyr Asn Ile
1               5

<210> SEQ ID NO 201
<211> LENGTH: 8
<212> TYPE: PRT
<213> ORGANISM: Homo sapiens

<400> SEQUENCE: 201

Lys Lys Ala Glu Arg Ser Thr Lys
1               5

<210> SEQ ID NO 202
<211> LENGTH: 12
<212> TYPE: PRT
<213> ORGANISM: Homo sapiens

<400> SEQUENCE: 202

Lys Lys Glu Glu Ser Ser Ser Arg Met Trp Pro Leu
1               5                   10

<210> SEQ ID NO 203
<211> LENGTH: 19
<212> TYPE: PRT
<213> ORGANISM: Homo sapiens

<400> SEQUENCE: 203

Lys Lys His Phe Ile Cys Thr Ser Phe Leu Asp Leu Gly Tyr Thr Val
1               5                   10                  15

Pro Val Tyr

<210> SEQ ID NO 204
<211> LENGTH: 10
<212> TYPE: PRT
<213> ORGANISM: Homo sapiens

<400> SEQUENCE: 204

Lys Ser Phe Cys Arg Ile Phe Leu Cys Trp
1               5                   10

<210> SEQ ID NO 205
<211> LENGTH: 12
<212> TYPE: PRT
<213> ORGANISM: Homo sapiens

<400> SEQUENCE: 205

Lys Ser Thr Ala His Ser Leu Cys Lys Gly Leu Met
1               5                   10

<210> SEQ ID NO 206
<211> LENGTH: 5
```

```
<212> TYPE: PRT
<213> ORGANISM: Homo sapiens

<400> SEQUENCE: 206

Lys Thr Thr Ile Phe
1               5

<210> SEQ ID NO 207
<211> LENGTH: 20
<212> TYPE: PRT
<213> ORGANISM: Homo sapiens

<400> SEQUENCE: 207

Leu Ala Tyr Val Ser Asn Ser His Gln Gly Lys Phe Gly Trp Leu Ser
1               5                   10                  15

Gly Leu Ser Arg
            20

<210> SEQ ID NO 208
<211> LENGTH: 15
<212> TYPE: PRT
<213> ORGANISM: Homo sapiens

<400> SEQUENCE: 208

Leu Asp Gly Met Leu Ala Ala Gln Thr Glu Glu Asp Pro Glu Thr
1               5                   10                  15

<210> SEQ ID NO 209
<211> LENGTH: 17
<212> TYPE: PRT
<213> ORGANISM: Homo sapiens

<400> SEQUENCE: 209

Leu Glu Thr Glu Ala Gly Glu Ser Leu Glu Pro Arg Arg Trp Arg Leu
1               5                   10                  15

Gln

<210> SEQ ID NO 210
<211> LENGTH: 13
<212> TYPE: PRT
<213> ORGANISM: Homo sapiens

<400> SEQUENCE: 210

Leu Glu Val Arg Ile Ser Arg Pro Ser Trp Leu Thr Arg
1               5                   10

<210> SEQ ID NO 211
<211> LENGTH: 10
<212> TYPE: PRT
<213> ORGANISM: Homo sapiens

<400> SEQUENCE: 211

Leu His Lys Pro Gln Ser Gln Trp Thr Arg
1               5                   10

<210> SEQ ID NO 212
<211> LENGTH: 20
<212> TYPE: PRT
<213> ORGANISM: Homo sapiens

<400> SEQUENCE: 212

Leu His Gln Asn Pro Lys Gly Leu Gly Ser Glu Ser Phe Trp Ile Thr
1               5                   10                  15
```

```
Leu Pro Gly Arg
            20
```

<210> SEQ ID NO 213
<211> LENGTH: 17
<212> TYPE: PRT
<213> ORGANISM: Homo sapiens

<400> SEQUENCE: 213

```
Leu Lys Asp Val Thr Val Ser Val Arg Leu Ala Pro Leu Tyr Ile Ser
1               5                   10                  15

Met
```

<210> SEQ ID NO 214
<211> LENGTH: 29
<212> TYPE: PRT
<213> ORGANISM: Homo sapiens

<400> SEQUENCE: 214

```
Leu Lys His Glu Asn Cys Leu Asn Pro Gly Arg Gly Cys Ser Glu
1               5                   10                  15

Ser Arg Trp Cys Arg Cys Thr Pro Thr Arg Thr Thr Glu
            20                  25
```

<210> SEQ ID NO 215
<211> LENGTH: 17
<212> TYPE: PRT
<213> ORGANISM: Homo sapiens

<400> SEQUENCE: 215

```
Leu Lys Gln Ile Leu Ser Ser Val Leu Asn Ser Glu Ile Glu Leu Leu
1               5                   10                  15

Leu
```

<210> SEQ ID NO 216
<211> LENGTH: 19
<212> TYPE: PRT
<213> ORGANISM: Homo sapiens

<400> SEQUENCE: 216

```
Leu Leu His Met Ala Ala Ala Arg Arg Ser Ala Glu Gln Arg Gly Lys
1               5                   10                  15

Ser Pro Ser
```

<210> SEQ ID NO 217
<211> LENGTH: 7
<212> TYPE: PRT
<213> ORGANISM: Homo sapiens

<400> SEQUENCE: 217

```
Leu Leu Pro Gln Pro Pro Glu
1               5
```

<210> SEQ ID NO 218
<211> LENGTH: 11
<212> TYPE: PRT
<213> ORGANISM: Homo sapiens

<400> SEQUENCE: 218

```
Leu Leu Ser His Leu Gln Asp Trp Gln His His
1               5                   10
```

```
<210> SEQ ID NO 219
<211> LENGTH: 14
<212> TYPE: PRT
<213> ORGANISM: Homo sapiens

<400> SEQUENCE: 219

Leu Leu Ser Lys Ser Leu Arg Asn Glu Asp Thr Ala Val Val
1               5                   10

<210> SEQ ID NO 220
<211> LENGTH: 43
<212> TYPE: PRT
<213> ORGANISM: Homo sapiens

<400> SEQUENCE: 220

Leu Gln Thr Gly Lys Glu Lys Ala Ser His Pro Pro Thr Leu Phe
1               5                   10                  15

Ser Pro Ile Ile Tyr Asn Asn Thr Asp Leu Arg Ala Val Lys Val Ile
            20                  25                  30

Leu Lys Tyr Tyr Ile Lys Trp Val Arg Arg Glu
        35                  40

<210> SEQ ID NO 221
<211> LENGTH: 22
<212> TYPE: PRT
<213> ORGANISM: Homo sapiens

<400> SEQUENCE: 221

Leu Gln Val Thr Leu Pro Arg Arg Gly Arg Asp Thr Cys Gly Ser His
1               5                   10                  15

Arg Glu Ala Thr Glu Arg
            20

<210> SEQ ID NO 222
<211> LENGTH: 4
<212> TYPE: PRT
<213> ORGANISM: Homo sapiens

<400> SEQUENCE: 222

Leu Arg Ile Thr
1

<210> SEQ ID NO 223
<211> LENGTH: 21
<212> TYPE: PRT
<213> ORGANISM: Homo sapiens

<400> SEQUENCE: 223

Leu Arg Leu Ser Thr Pro Trp Pro Thr Leu Lys Pro His Leu Lys Gly
1               5                   10                  15

Lys Val Met Ser Leu
            20

<210> SEQ ID NO 224
<211> LENGTH: 15
<212> TYPE: PRT
<213> ORGANISM: Homo sapiens

<400> SEQUENCE: 224

Leu Ser Glu Ser Ile Trp Phe Ala Phe His Phe Asp Asp Cys Lys
1               5                   10                  15

<210> SEQ ID NO 225
```

```
<211> LENGTH: 6
<212> TYPE: PRT
<213> ORGANISM: Homo sapiens

<400> SEQUENCE: 225

Leu Ser His Gly Thr Gly
1               5

<210> SEQ ID NO 226
<211> LENGTH: 6
<212> TYPE: PRT
<213> ORGANISM: Homo sapiens

<400> SEQUENCE: 226

Leu Thr Arg Asn Asp Ile
1               5

<210> SEQ ID NO 227
<211> LENGTH: 5
<212> TYPE: PRT
<213> ORGANISM: Homo sapiens

<400> SEQUENCE: 227

Met Lys Glu Tyr Ala
1               5

<210> SEQ ID NO 228
<211> LENGTH: 18
<212> TYPE: PRT
<213> ORGANISM: Homo sapiens

<400> SEQUENCE: 228

Asn Glu Leu Trp Leu His His Leu Ser Ser Ser Arg His Leu Met
1               5                   10                  15

Ser Ser

<210> SEQ ID NO 229
<211> LENGTH: 11
<212> TYPE: PRT
<213> ORGANISM: Homo sapiens

<400> SEQUENCE: 229

Asn Gly Cys Val Tyr Leu Ser Lys Phe Lys Leu
1               5                   10

<210> SEQ ID NO 230
<211> LENGTH: 23
<212> TYPE: PRT
<213> ORGANISM: Homo sapiens

<400> SEQUENCE: 230

Asn Lys Glu Arg Glu Val Phe Ser Thr Asn Gly Thr Gly Tyr Pro His
1               5                   10                  15

Gly Lys Lys Arg Thr Thr Gln
            20

<210> SEQ ID NO 231
<211> LENGTH: 4
<212> TYPE: PRT
<213> ORGANISM: Homo sapiens

<400> SEQUENCE: 231

Asn Asn Gln Lys
1
```

<210> SEQ ID NO 232
<211> LENGTH: 7
<212> TYPE: PRT
<213> ORGANISM: Homo sapiens

<400> SEQUENCE: 232

Asn Arg Gly Lys His Arg Gly
1               5

<210> SEQ ID NO 233
<211> LENGTH: 5
<212> TYPE: PRT
<213> ORGANISM: Homo sapiens

<400> SEQUENCE: 233

Asn Ser Ala Cys Leu
1               5

<210> SEQ ID NO 234
<211> LENGTH: 5
<212> TYPE: PRT
<213> ORGANISM: Homo sapiens

<400> SEQUENCE: 234

Asn Ser Ala Gln Asn
1               5

<210> SEQ ID NO 235
<211> LENGTH: 32
<212> TYPE: PRT
<213> ORGANISM: Homo sapiens

<400> SEQUENCE: 235

Asn Ser Ala Ser Thr Glu Pro Ser Thr Asn Arg Leu Gln Leu Pro Trp
1               5                   10                  15

Val Gly Gly Leu Met Gln Thr Gly Arg Leu Pro Gly Ser Leu Thr Ala
            20                  25                  30

<210> SEQ ID NO 236
<211> LENGTH: 20
<212> TYPE: PRT
<213> ORGANISM: Homo sapiens

<400> SEQUENCE: 236

Asn Ser Ala Ser Thr Arg Pro Ile Ser His Ile Arg Arg Arg Thr Leu
1               5                   10                  15

Leu Ser Ser Ala
            20

<210> SEQ ID NO 237
<211> LENGTH: 18
<212> TYPE: PRT
<213> ORGANISM: Homo sapiens

<400> SEQUENCE: 237

Asn Ser Asp Leu Val Arg His Gln Phe Lys Gly Lys Thr Thr Leu Lys
1               5                   10                  15

Val His

<210> SEQ ID NO 238
<211> LENGTH: 27
<212> TYPE: PRT

<210> ORGANISM: Homo sapiens

<400> SEQUENCE: 238

Asn Ser Asp Gln Ile Gln Asn Thr Gly Ala Glu Ser Arg Glu Lys Val
1               5                   10                  15

Arg Met Ser Ile Thr Ala Asp Glu Phe Val Gly
            20                  25

<210> SEQ ID NO 239
<211> LENGTH: 5
<212> TYPE: PRT
<213> ORGANISM: Homo sapiens

<400> SEQUENCE: 239

Asn Ser Asp Val Ile
1               5

<210> SEQ ID NO 240
<211> LENGTH: 21
<212> TYPE: PRT
<213> ORGANISM: Homo sapiens

<400> SEQUENCE: 240

Asn Ser Glu Cys Thr Cys Ile Ile Val Lys Gly Asn Thr Phe Ser Pro
1               5                   10                  15

Cys Lys Phe Ile Val
            20

<210> SEQ ID NO 241
<211> LENGTH: 4
<212> TYPE: PRT
<213> ORGANISM: Homo sapiens

<400> SEQUENCE: 241

Asn Ser Glu Gly
1

<210> SEQ ID NO 242
<211> LENGTH: 6
<212> TYPE: PRT
<213> ORGANISM: Homo sapiens

<400> SEQUENCE: 242

Asn Ser Glu Gly Ala Thr
1               5

<210> SEQ ID NO 243
<211> LENGTH: 25
<212> TYPE: PRT
<213> ORGANISM: Homo sapiens

<400> SEQUENCE: 243

Asn Ser Glu Gln Gln Arg Leu Lys Glu Leu Lys Ser Glu His Thr Asn
1               5                   10                  15

Asn Lys Lys Val Lys Gln Pro Cys Cys
            20                  25

<210> SEQ ID NO 244
<211> LENGTH: 14
<212> TYPE: PRT
<213> ORGANISM: Homo sapiens

<400> SEQUENCE: 244

Asn Ser Glu Ser Asn Ser Phe Ala Ser Lys Asn Lys Phe Asn
1               5                   10

<210> SEQ ID NO 245
<211> LENGTH: 12
<212> TYPE: PRT
<213> ORGANISM: Homo sapiens

<400> SEQUENCE: 245

Asn Ser Phe Cys Val Cys Val Phe Asn Ser Gln Ser
1               5                   10

<210> SEQ ID NO 246
<211> LENGTH: 7
<212> TYPE: PRT
<213> ORGANISM: Homo sapiens

<400> SEQUENCE: 246

Asn Ser Phe Gly Phe Ser Thr
1               5

<210> SEQ ID NO 247
<211> LENGTH: 21
<212> TYPE: PRT
<213> ORGANISM: Homo sapiens

<400> SEQUENCE: 247

Asn Ser Phe Leu Leu Glu Ile Gln Glu Pro Ser Leu Gly Val Trp Ile
1               5                   10                  15

Arg Thr Pro Phe Leu
            20

<210> SEQ ID NO 248
<211> LENGTH: 6
<212> TYPE: PRT
<213> ORGANISM: Homo sapiens

<400> SEQUENCE: 248

Asn Ser Phe Leu Ser Phe
1               5

<210> SEQ ID NO 249
<211> LENGTH: 11
<212> TYPE: PRT
<213> ORGANISM: Homo sapiens

<400> SEQUENCE: 249

Asn Ser Phe Pro Ser Ser Ile Cys Phe Asn Ser
1               5                   10

<210> SEQ ID NO 250
<211> LENGTH: 19
<212> TYPE: PRT
<213> ORGANISM: Homo sapiens

<400> SEQUENCE: 250

Asn Ser Phe Gln Gly Leu Gln Asp Tyr Leu Ile Lys Ser Ser Met Asn
1               5                   10                  15

Leu Val Leu

<210> SEQ ID NO 251
<211> LENGTH: 11
<212> TYPE: PRT
<213> ORGANISM: Homo sapiens

```
<400> SEQUENCE: 251

Asn Ser Phe Arg Lys Gln Arg His Trp Lys Gly
1               5                   10

<210> SEQ ID NO 252
<211> LENGTH: 5
<212> TYPE: PRT
<213> ORGANISM: Homo sapiens

<400> SEQUENCE: 252

Asn Ser Phe Arg Leu
1               5

<210> SEQ ID NO 253
<211> LENGTH: 12
<212> TYPE: PRT
<213> ORGANISM: Homo sapiens

<400> SEQUENCE: 253

Asn Ser Phe Arg Pro His Arg Phe Lys Ser Asn Ala
1               5                   10

<210> SEQ ID NO 254
<211> LENGTH: 7
<212> TYPE: PRT
<213> ORGANISM: Homo sapiens

<400> SEQUENCE: 254

Asn Ser Phe Arg Tyr Phe Ala
1               5

<210> SEQ ID NO 255
<211> LENGTH: 6
<212> TYPE: PRT
<213> ORGANISM: Homo sapiens

<400> SEQUENCE: 255

Asn Ser Gly Val Ser Trp
1               5

<210> SEQ ID NO 256
<211> LENGTH: 6
<212> TYPE: PRT
<213> ORGANISM: Homo sapiens

<400> SEQUENCE: 256

Asn Ser His Cys Asp Ile
1               5

<210> SEQ ID NO 257
<211> LENGTH: 9
<212> TYPE: PRT
<213> ORGANISM: Homo sapiens

<400> SEQUENCE: 257

Asn Ser His Asn Pro Lys Leu Glu Lys
1               5

<210> SEQ ID NO 258
<211> LENGTH: 16
<212> TYPE: PRT
<213> ORGANISM: Homo sapiens

<400> SEQUENCE: 258
```

```
Asn Ser Ile His His Val Leu Leu Ser Leu His Pro Pro Leu Tyr Lys
1               5                   10                  15

<210> SEQ ID NO 259
<211> LENGTH: 5
<212> TYPE: PRT
<213> ORGANISM: Homo sapiens

<400> SEQUENCE: 259

Asn Ser Ile His Met
1               5

<210> SEQ ID NO 260
<211> LENGTH: 20
<212> TYPE: PRT
<213> ORGANISM: Homo sapiens

<400> SEQUENCE: 260

Asn Ser Ile Ile Pro Arg Ala Ile Trp Leu Ser Val Glu Arg Met Trp
1               5                   10                  15

Gln Leu Arg Trp
            20

<210> SEQ ID NO 261
<211> LENGTH: 8
<212> TYPE: PRT
<213> ORGANISM: Homo sapiens

<400> SEQUENCE: 261

Asn Ser Ile Lys Cys Lys Lys Met
1               5

<210> SEQ ID NO 262
<211> LENGTH: 17
<212> TYPE: PRT
<213> ORGANISM: Homo sapiens

<400> SEQUENCE: 262

Asn Ser Ile Lys Arg Phe Ser Ala Ser Cys Val Ala Arg Ile Cys Pro
1               5                   10                  15

Gly

<210> SEQ ID NO 263
<211> LENGTH: 4
<212> TYPE: PRT
<213> ORGANISM: Homo sapiens

<400> SEQUENCE: 263

Asn Ser Ile Leu
1

<210> SEQ ID NO 264
<211> LENGTH: 12
<212> TYPE: PRT
<213> ORGANISM: Homo sapiens

<400> SEQUENCE: 264

Asn Ser Ile Leu Ile Lys Tyr Gly Asp Thr Trp Asn
1               5                   10

<210> SEQ ID NO 265
<211> LENGTH: 20
<212> TYPE: PRT
```

```
<213> ORGANISM: Homo sapiens

<400> SEQUENCE: 265

Asn Ser Ile Leu Gln Ser Ala Gly Glu Ser Phe Leu Leu His Asn Leu
1               5                   10                  15

Asn Leu Cys Ser
            20

<210> SEQ ID NO 266
<211> LENGTH: 19
<212> TYPE: PRT
<213> ORGANISM: Homo sapiens

<400> SEQUENCE: 266

Asn Ser Ile Thr His Leu Glu Lys His Thr Ile Leu Tyr Thr Asn Ser
1               5                   10                  15

Ser Thr Lys

<210> SEQ ID NO 267
<211> LENGTH: 15
<212> TYPE: PRT
<213> ORGANISM: Homo sapiens

<400> SEQUENCE: 267

Asn Ser Lys Glu Thr Ser Ser Asn Gly Thr Glu Trp Asn Pro His
1               5                   10                  15

<210> SEQ ID NO 268
<211> LENGTH: 7
<212> TYPE: PRT
<213> ORGANISM: Homo sapiens

<400> SEQUENCE: 268

Asn Ser Lys Gly Arg Arg Val
1               5

<210> SEQ ID NO 269
<211> LENGTH: 5
<212> TYPE: PRT
<213> ORGANISM: Homo sapiens

<400> SEQUENCE: 269

Asn Ser Lys His Arg
1               5

<210> SEQ ID NO 270
<211> LENGTH: 16
<212> TYPE: PRT
<213> ORGANISM: Homo sapiens

<400> SEQUENCE: 270

Asn Ser Lys Ile Met Phe Ser Lys Met Phe Leu Ser Gln Ile Thr Glu
1               5                   10                  15

<210> SEQ ID NO 271
<211> LENGTH: 11
<212> TYPE: PRT
<213> ORGANISM: Homo sapiens

<400> SEQUENCE: 271

Asn Ser Lys Gln Arg Phe Phe Leu Lys Lys Lys
1               5                   10
```

```
<210> SEQ ID NO 272
<211> LENGTH: 8
<212> TYPE: PRT
<213> ORGANISM: Homo sapiens

<400> SEQUENCE: 272

Asn Ser Leu Cys Gly Ile Cys Ile
1               5

<210> SEQ ID NO 273
<211> LENGTH: 6
<212> TYPE: PRT
<213> ORGANISM: Homo sapiens

<400> SEQUENCE: 273

Asn Ser Leu Lys Lys Leu
1               5

<210> SEQ ID NO 274
<211> LENGTH: 10
<212> TYPE: PRT
<213> ORGANISM: Homo sapiens

<400> SEQUENCE: 274

Asn Ser Leu Leu Cys Leu Ile Cys Leu Thr
1               5                   10

<210> SEQ ID NO 275
<211> LENGTH: 16
<212> TYPE: PRT
<213> ORGANISM: Homo sapiens

<400> SEQUENCE: 275

Asn Ser Leu Asn Lys Ile Gln Asn Thr Phe Glu Ser Ser Thr Ile Asp
1               5                   10                  15

<210> SEQ ID NO 276
<211> LENGTH: 6
<212> TYPE: PRT
<213> ORGANISM: Homo sapiens

<400> SEQUENCE: 276

Asn Ser Leu Pro Leu Thr
1               5

<210> SEQ ID NO 277
<211> LENGTH: 9
<212> TYPE: PRT
<213> ORGANISM: Homo sapiens

<400> SEQUENCE: 277

Asn Ser Leu Pro Trp Lys Gln Lys Val
1               5

<210> SEQ ID NO 278
<211> LENGTH: 4
<212> TYPE: PRT
<213> ORGANISM: Homo sapiens

<400> SEQUENCE: 278

Asn Ser Leu Ser
1

<210> SEQ ID NO 279
<211> LENGTH: 13
```

<212> TYPE: PRT
<213> ORGANISM: Homo sapiens

<400> SEQUENCE: 279

Asn Ser Leu Ser Phe Ala Asp Trp Phe Trp Lys Arg Ser
1               5                   10

<210> SEQ ID NO 280
<211> LENGTH: 13
<212> TYPE: PRT
<213> ORGANISM: Homo sapiens

<400> SEQUENCE: 280

Asn Ser Leu Ser Ser Phe His Cys Ser Ser His Cys Phe
1               5                   10

<210> SEQ ID NO 281
<211> LENGTH: 19
<212> TYPE: PRT
<213> ORGANISM: Homo sapiens

<400> SEQUENCE: 281

Asn Ser Met Met Asp His Val Thr Asn Asn Ala Thr Gly Met Asn Ile
1               5                   10                  15

Met Glu Lys

<210> SEQ ID NO 282
<211> LENGTH: 26
<212> TYPE: PRT
<213> ORGANISM: Homo sapiens

<400> SEQUENCE: 282

Asn Ser Met Ser Met Pro Arg Leu Cys Gly Arg Met Lys Glu Cys Val
1               5                   10                  15

Pro Ala Thr Asn Ala Pro Thr Ser Thr Ser
            20                  25

<210> SEQ ID NO 283
<211> LENGTH: 32
<212> TYPE: PRT
<213> ORGANISM: Homo sapiens

<400> SEQUENCE: 283

Asn Ser Met Val Val Thr Ala Thr Ser Tyr Ser Thr Pro Ile Pro Glu
1               5                   10                  15

Asp Arg Leu Ser Thr Arg Gly Lys Glu Gln Met Pro His Glu Met Ser
            20                  25                  30

<210> SEQ ID NO 284
<211> LENGTH: 5
<212> TYPE: PRT
<213> ORGANISM: Homo sapiens

<400> SEQUENCE: 284

Asn Ser Asn Glu Glu
1               5

<210> SEQ ID NO 285
<211> LENGTH: 35
<212> TYPE: PRT
<213> ORGANISM: Homo sapiens

<400> SEQUENCE: 285

```
Asn Ser Asn Pro Tyr Pro Gly Gly Arg Ser Thr Ser Gly Asp Pro Lys
1               5                   10                  15

Phe Lys Pro Arg Asn Cys Ser Val Pro Gln Trp Leu Gly Tyr Asn Pro
            20                  25                  30

Phe Trp Pro
        35

<210> SEQ ID NO 286
<211> LENGTH: 19
<212> TYPE: PRT
<213> ORGANISM: Homo sapiens

<400> SEQUENCE: 286

Asn Ser Pro Ala Gly Ile Ser Arg Glu Leu Val Asp Lys Leu Ala Ala
1               5                   10                  15

Ala Leu Glu

<210> SEQ ID NO 287
<211> LENGTH: 7
<212> TYPE: PRT
<213> ORGANISM: Homo sapiens

<400> SEQUENCE: 287

Asn Ser Pro Ala Ser Ala Ser
1               5

<210> SEQ ID NO 288
<211> LENGTH: 15
<212> TYPE: PRT
<213> ORGANISM: Homo sapiens

<400> SEQUENCE: 288

Asn Ser Pro Lys Met Gly Ser Pro Ser Leu Leu Lys Tyr Tyr Thr
1               5                   10                  15

<210> SEQ ID NO 289
<211> LENGTH: 17
<212> TYPE: PRT
<213> ORGANISM: Homo sapiens

<400> SEQUENCE: 289

Asn Ser Pro Lys Met Gly Ser Pro Ser Leu Leu Lys Tyr Tyr Thr Arg
1               5                   10                  15

Ser

<210> SEQ ID NO 290
<211> LENGTH: 6
<212> TYPE: PRT
<213> ORGANISM: Homo sapiens

<400> SEQUENCE: 290

Asn Ser Pro Pro Ala Asn
1               5

<210> SEQ ID NO 291
<211> LENGTH: 13
<212> TYPE: PRT
<213> ORGANISM: Homo sapiens

<400> SEQUENCE: 291

Asn Ser Pro Ser Gln Pro Ala Cys Leu Gly Ala Gln Arg
1               5                   10
```

<210> SEQ ID NO 292
<211> LENGTH: 18
<212> TYPE: PRT
<213> ORGANISM: Homo sapiens

<400> SEQUENCE: 292

Asn Ser Pro Val Pro Ser Val Thr Thr Asp Tyr Gln Asn Ile Ser Leu
1               5                   10                  15

Leu Thr

<210> SEQ ID NO 293
<211> LENGTH: 9
<212> TYPE: PRT
<213> ORGANISM: Homo sapiens

<400> SEQUENCE: 293

Asn Ser Gln Ala Val Cys Ile Phe Phe
1               5

<210> SEQ ID NO 294
<211> LENGTH: 22
<212> TYPE: PRT
<213> ORGANISM: Homo sapiens

<400> SEQUENCE: 294

Asn Ser Gln Asn Val Phe Asn Ser Ser Phe His Phe Met Ala Leu
1               5                   10                  15

Glu Arg Tyr Arg Arg Lys
            20

<210> SEQ ID NO 295
<211> LENGTH: 10
<212> TYPE: PRT
<213> ORGANISM: Homo sapiens

<400> SEQUENCE: 295

Asn Ser Gln Arg Leu Ile Trp Leu Ser Asn
1               5                   10

<210> SEQ ID NO 296
<211> LENGTH: 12
<212> TYPE: PRT
<213> ORGANISM: Homo sapiens

<400> SEQUENCE: 296

Asn Ser Gln Val Gly Leu Ser Ser Ser Tyr Pro Gln
1               5                   10

<210> SEQ ID NO 297
<211> LENGTH: 8
<212> TYPE: PRT
<213> ORGANISM: Homo sapiens

<400> SEQUENCE: 297

Asn Ser Arg Cys His Cys Pro Ala
1               5

<210> SEQ ID NO 298
<211> LENGTH: 6
<212> TYPE: PRT
<213> ORGANISM: Homo sapiens

<400> SEQUENCE: 298

Asn Ser Arg Phe Asp Phe
1               5

<210> SEQ ID NO 299
<211> LENGTH: 18
<212> TYPE: PRT
<213> ORGANISM: Homo sapiens

<400> SEQUENCE: 299

Asn Ser Ser Asp Ile Thr Leu Ile Glu Lys Lys Glu Leu Ile Lys Ala
1               5                   10                  15

Asn Ile

<210> SEQ ID NO 300
<211> LENGTH: 7
<212> TYPE: PRT
<213> ORGANISM: Homo sapiens

<400> SEQUENCE: 300

Asn Ser Ser Phe Leu Met Thr
1               5

<210> SEQ ID NO 301
<211> LENGTH: 15
<212> TYPE: PRT
<213> ORGANISM: Homo sapiens

<400> SEQUENCE: 301

Asn Ser Ser Phe Leu Gln Gly Ala Leu Val Pro Leu Ser Gly Glu
1               5                   10                  15

<210> SEQ ID NO 302
<211> LENGTH: 28
<212> TYPE: PRT
<213> ORGANISM: Homo sapiens

<400> SEQUENCE: 302

Asn Ser Ser Gly Leu Leu Lys Val Ser Leu Leu Lys Tyr His Pro Ser
1               5                   10                  15

Phe Met Asn Ser Arg Gly Phe Ser Leu Gln Val Leu
            20                  25

<210> SEQ ID NO 303
<211> LENGTH: 18
<212> TYPE: PRT
<213> ORGANISM: Homo sapiens

<400> SEQUENCE: 303

Asn Ser Ser Arg Gln Pro His Pro Leu Leu Thr Ser Leu Asn Ile Leu
1               5                   10                  15

Tyr Ile

<210> SEQ ID NO 304
<211> LENGTH: 15
<212> TYPE: PRT
<213> ORGANISM: Homo sapiens

<400> SEQUENCE: 304

Asn Ser Ser Arg Thr Ala Phe Ser Phe His Ser Leu Leu Leu Leu
1               5                   10                  15

<210> SEQ ID NO 305
<211> LENGTH: 16

<212> TYPE: PRT
<213> ORGANISM: Homo sapiens

<400> SEQUENCE: 305

Asn Ser Ser Ser Gln His Arg Glu His Glu Lys Glu Glu Lys Tyr
1               5                   10                  15

<210> SEQ ID NO 306
<211> LENGTH: 53
<212> TYPE: PRT
<213> ORGANISM: Homo sapiens

<400> SEQUENCE: 306

Asn Ser Ser Ser Ser Asn Pro Ile Leu Ser His Gly Thr Thr Lys
1               5                   10                  15

Asn Lys Val Cys Ser Ala Pro Glu Ala Leu Tyr Ala Gly Asp Gly Gln
            20                  25                  30

Leu Asn Glu Asn Leu Lys Gly Lys Pro Ser Gly Leu Arg Cys Val Pro
        35                  40                  45

Leu Arg Asp Phe Thr
    50

<210> SEQ ID NO 307
<211> LENGTH: 49
<212> TYPE: PRT
<213> ORGANISM: Homo sapiens

<400> SEQUENCE: 307

Asn Ser Ser Ser Tyr Arg Pro Gln Arg Val Trp Cys Gly Ser Ile Cys
1               5                   10                  15

Ser Arg Ala Ser Thr Gly Ile Pro Ile Pro Gln Gly Leu Pro Pro Lys
            20                  25                  30

Tyr Leu Ala Phe Lys Glu Leu Ser Tyr Leu Asn Ser Ala Gly Thr Ser
        35                  40                  45

Cys

<210> SEQ ID NO 308
<211> LENGTH: 19
<212> TYPE: PRT
<213> ORGANISM: Homo sapiens

<400> SEQUENCE: 308

Asn Ser Ser Val Thr Leu Met Arg Gln Arg Val Met Met Met Gly Arg
1               5                   10                  15

His Thr Thr

<210> SEQ ID NO 309
<211> LENGTH: 36
<212> TYPE: PRT
<213> ORGANISM: Homo sapiens

<400> SEQUENCE: 309

Asn Ser Ser Trp His Ile Arg Ser Gln Gly Glu Asp Asn Arg Glu Thr
1               5                   10                  15

Ala Leu Val Tyr Arg Lys Gln Ile Phe Ser Glu Thr Leu His Tyr Tyr
            20                  25                  30

Lys Lys Lys Lys
        35

<210> SEQ ID NO 310

```
<211> LENGTH: 5
<212> TYPE: PRT
<213> ORGANISM: Homo sapiens

<400> SEQUENCE: 310

Asn Ser Thr Asp Lys
1               5

<210> SEQ ID NO 311
<211> LENGTH: 26
<212> TYPE: PRT
<213> ORGANISM: Homo sapiens

<400> SEQUENCE: 311

Asn Ser Thr Gly Asn Met Lys Gly Ile His Leu Thr Phe Gln Leu Lys
1               5                   10                  15

Arg Met Gly Lys Pro Thr Pro Leu Leu Phe
            20                  25

<210> SEQ ID NO 312
<211> LENGTH: 4
<212> TYPE: PRT
<213> ORGANISM: Homo sapiens

<400> SEQUENCE: 312

Asn Ser Thr Arg
1

<210> SEQ ID NO 313
<211> LENGTH: 10
<212> TYPE: PRT
<213> ORGANISM: Homo sapiens

<400> SEQUENCE: 313

Asn Ser Thr Ser Lys Ser Val Glu His Ser
1               5                   10

<210> SEQ ID NO 314
<211> LENGTH: 15
<212> TYPE: PRT
<213> ORGANISM: Homo sapiens

<400> SEQUENCE: 314

Asn Ser Thr Val Leu Lys Tyr Val Thr Leu Pro His Leu Arg Glu
1               5                   10                  15

<210> SEQ ID NO 315
<211> LENGTH: 5
<212> TYPE: PRT
<213> ORGANISM: Homo sapiens

<400> SEQUENCE: 315

Asn Ser Val Cys Val
1               5

<210> SEQ ID NO 316
<211> LENGTH: 12
<212> TYPE: PRT
<213> ORGANISM: Homo sapiens

<400> SEQUENCE: 316

Asn Ser Val Ile Ile Glu Ser Leu Val Val Asn Val
1               5                   10
```

-continued

<210> SEQ ID NO 317
<211> LENGTH: 14
<212> TYPE: PRT
<213> ORGANISM: Homo sapiens

<400> SEQUENCE: 317

Asn Ser Val Asn Phe Ile Leu Ile Pro Leu Asp Leu Glu Gly
1               5                   10

<210> SEQ ID NO 318
<211> LENGTH: 28
<212> TYPE: PRT
<213> ORGANISM: Homo sapiens

<400> SEQUENCE: 318

Asn Ser Val Gln Gly Arg Ala Val Leu Leu Cys His Gly Leu Thr Gly
1               5                   10                  15

Arg Ala Trp Phe Tyr Leu Tyr Gly Leu Phe Cys Val
            20                  25

<210> SEQ ID NO 319
<211> LENGTH: 5
<212> TYPE: PRT
<213> ORGANISM: Homo sapiens

<400> SEQUENCE: 319

Asn Ser Val Val His
1               5

<210> SEQ ID NO 320
<211> LENGTH: 6
<212> TYPE: PRT
<213> ORGANISM: Homo sapiens

<400> SEQUENCE: 320

Asn Ser Val Tyr Met Ile
1               5

<210> SEQ ID NO 321
<211> LENGTH: 28
<212> TYPE: PRT
<213> ORGANISM: Homo sapiens

<400> SEQUENCE: 321

Asn Ser Tyr Cys Val Asn Gln Ala Gly Leu Glu Leu Leu Ala Ser Ser
1               5                   10                  15

Asp Pro Leu Ala Leu Ala Ser Gly Met Leu Gly Leu
            20                  25

<210> SEQ ID NO 322
<211> LENGTH: 7
<212> TYPE: PRT
<213> ORGANISM: Homo sapiens

<400> SEQUENCE: 322

Asn Ser Tyr Leu Phe Ser Arg
1               5

<210> SEQ ID NO 323
<211> LENGTH: 11
<212> TYPE: PRT
<213> ORGANISM: Homo sapiens

<400> SEQUENCE: 323

```
Pro Ala Trp Ala Thr Lys Ser Lys Thr Pro Ser
1               5                   10
```

<210> SEQ ID NO 324
<211> LENGTH: 11
<212> TYPE: PRT
<213> ORGANISM: Homo sapiens

<400> SEQUENCE: 324

```
Pro Gly Leu Gly Glu Trp Cys Arg Val Cys Val
1               5                   10
```

<210> SEQ ID NO 325
<211> LENGTH: 23
<212> TYPE: PRT
<213> ORGANISM: Homo sapiens

<400> SEQUENCE: 325

```
Pro Gly Arg His Leu Ala Glu Ala Gln His Gly His Pro Arg Pro Cys
1               5                   10                  15

Leu His Ser Glu Val Phe Ser
            20
```

<210> SEQ ID NO 326
<211> LENGTH: 23
<212> TYPE: PRT
<213> ORGANISM: Homo sapiens

<400> SEQUENCE: 326

```
Pro His Ala Thr Ser His Leu Arg Val Lys His Glu Ile Ser Gln Ile
1               5                   10                  15

Gln His Pro Pro Leu Leu Ser
            20
```

<210> SEQ ID NO 327
<211> LENGTH: 29
<212> TYPE: PRT
<213> ORGANISM: Homo sapiens

<400> SEQUENCE: 327

```
Pro Ile Ser Leu Arg Gly Ala Thr Ala Gly Arg Ala Glu Arg Ile Arg
1               5                   10                  15

Glu Glu Glu Val Arg Gly Ala Val His His Lys Arg His
            20                  25
```

<210> SEQ ID NO 328
<211> LENGTH: 31
<212> TYPE: PRT
<213> ORGANISM: Homo sapiens

<400> SEQUENCE: 328

```
Pro Gln Arg Thr Thr Leu Asn Phe Leu Leu Gly Gln Pro Ala Arg Leu
1               5                   10                  15

Pro Leu Gly Leu Ser Val Gly Asp Arg Pro Thr Ser Gln Gly Arg
            20                  25                  30
```

<210> SEQ ID NO 329
<211> LENGTH: 12
<212> TYPE: PRT
<213> ORGANISM: Homo sapiens

<400> SEQUENCE: 329

```
Pro Arg Phe Pro Ser Ser Ala Gln Gln Arg Met Lys
```

```
1               5                   10
```

<210> SEQ ID NO 330
<211> LENGTH: 21
<212> TYPE: PRT
<213> ORGANISM: Homo sapiens

<400> SEQUENCE: 330

```
Pro Ser Arg Pro Pro Arg Arg Gly Gly Gly Ala Arg Ala His Val Leu
1               5                   10                  15

Gly Pro Glu Arg Trp
            20
```

<210> SEQ ID NO 331
<211> LENGTH: 9
<212> TYPE: PRT
<213> ORGANISM: Homo sapiens

<400> SEQUENCE: 331

```
Gln Gly His Thr Gly Val Ser His Lys
1               5
```

<210> SEQ ID NO 332
<211> LENGTH: 14
<212> TYPE: PRT
<213> ORGANISM: Homo sapiens

<400> SEQUENCE: 332

```
Gln Lys Thr Lys His Arg Ile Phe Ser Leu Ile Gly Gly Asn
1               5                   10
```

<210> SEQ ID NO 333
<211> LENGTH: 8
<212> TYPE: PRT
<213> ORGANISM: Homo sapiens

<400> SEQUENCE: 333

```
Gln Met Leu Leu Leu Pro Ala Ile
1               5
```

<210> SEQ ID NO 334
<211> LENGTH: 30
<212> TYPE: PRT
<213> ORGANISM: Homo sapiens

<400> SEQUENCE: 334

```
Gln Arg Ser Arg Val Ala Glu Gly Trp Arg Gly Pro Leu Asn Pro Glu
1               5                   10                  15

Leu Thr Pro Lys Cys Ile Asp Pro Ser Met His Gly Trp Arg
            20                  25                  30
```

<210> SEQ ID NO 335
<211> LENGTH: 16
<212> TYPE: PRT
<213> ORGANISM: Homo sapiens

<400> SEQUENCE: 335

```
Gln Ser Leu Pro Pro Ala Arg Asn Cys Asn Lys Pro Asp Ser Met Leu
1               5                   10                  15
```

<210> SEQ ID NO 336
<211> LENGTH: 36
<212> TYPE: PRT
<213> ORGANISM: Homo sapiens

```
<400> SEQUENCE: 336

Gln Val Pro Arg Val Leu Pro Gln His Arg Leu Gly Leu Ala Gly Glu
1               5                   10                  15

Glu Ala Gly Ala Pro Ser Ile Pro Ala Thr Asp His Arg Arg Leu Arg
            20                  25                  30

Ser Gly Gln Leu
        35

<210> SEQ ID NO 337
<211> LENGTH: 9
<212> TYPE: PRT
<213> ORGANISM: Homo sapiens

<400> SEQUENCE: 337

Gln Val Ser Gly Pro Pro Ser Lys Ile
1               5

<210> SEQ ID NO 338
<211> LENGTH: 17
<212> TYPE: PRT
<213> ORGANISM: Homo sapiens

<400> SEQUENCE: 338

Gln Trp Leu Thr Pro Val Ile Pro Thr Leu Trp Glu Ala Lys Ala Gly
1               5                   10                  15

Gly

<210> SEQ ID NO 339
<211> LENGTH: 28
<212> TYPE: PRT
<213> ORGANISM: Homo sapiens

<400> SEQUENCE: 339

Arg Ala Leu Gln Gln Leu Arg His Pro Asp Leu His Leu Gln Arg Arg
1               5                   10                  15

Ser Gln Ala Gln Gln His Gln Gly Gly Gln Asp Ser
            20                  25

<210> SEQ ID NO 340
<211> LENGTH: 25
<212> TYPE: PRT
<213> ORGANISM: Homo sapiens

<400> SEQUENCE: 340

Arg Ala Val Arg Arg Glu Ala Ser His Arg Pro Ser Pro Leu Ala
1               5                   10                  15

Ser Arg Arg Pro Leu Asp Ala Leu Ser
            20                  25

<210> SEQ ID NO 341
<211> LENGTH: 9
<212> TYPE: PRT
<213> ORGANISM: Homo sapiens

<400> SEQUENCE: 341

Arg Asp Asp Ser Asp Tyr Ser Val Glu
1               5

<210> SEQ ID NO 342
<211> LENGTH: 37
<212> TYPE: PRT
```

<213> ORGANISM: Homo sapiens

<400> SEQUENCE: 342

Arg Glu Cys Thr Arg Cys Arg Arg Lys Thr Glu Ser Thr Ala Gln Arg
1               5                   10                  15

Val Lys Lys Pro Ala Thr Leu Leu Ala Ser Val Lys Pro Pro Ala Asn
                20                  25                  30

Ala Val Ser Thr Met
                35

<210> SEQ ID NO 343
<211> LENGTH: 7
<212> TYPE: PRT
<213> ORGANISM: Homo sapiens

<400> SEQUENCE: 343

Arg Gly Pro Lys Arg Leu Leu
1               5

<210> SEQ ID NO 344
<211> LENGTH: 7
<212> TYPE: PRT
<213> ORGANISM: Homo sapiens

<400> SEQUENCE: 344

Arg Ile Ser Ile Leu Lys Arg
1               5

<210> SEQ ID NO 345
<211> LENGTH: 21
<212> TYPE: PRT
<213> ORGANISM: Homo sapiens

<400> SEQUENCE: 345

Arg Ile Val Arg Val Thr Pro Arg Arg Ser Trp Asn His Tyr Glu Thr
1               5                   10                  15

Ile Glu Ser Lys Glu
                20

<210> SEQ ID NO 346
<211> LENGTH: 9
<212> TYPE: PRT
<213> ORGANISM: Homo sapiens

<400> SEQUENCE: 346

Arg Leu Gly Pro Gln Ala Arg His Gly
1               5

<210> SEQ ID NO 347
<211> LENGTH: 4
<212> TYPE: PRT
<213> ORGANISM: Homo sapiens

<400> SEQUENCE: 347

Arg Leu His Arg
1

<210> SEQ ID NO 348
<211> LENGTH: 14
<212> TYPE: PRT
<213> ORGANISM: Homo sapiens

<400> SEQUENCE: 348

-continued

```
Arg Met Lys Gln Ile Val Arg Lys Val Glu Pro Ile Met Thr
1               5                   10
```

<210> SEQ ID NO 349
<211> LENGTH: 17
<212> TYPE: PRT
<213> ORGANISM: Homo sapiens

<400> SEQUENCE: 349

```
Arg Met Met Ser Ser Ser Ile Gln Ser Leu Arg Lys Ala Gly Ser Glu
1               5                   10                  15

Pro
```

<210> SEQ ID NO 350
<211> LENGTH: 12
<212> TYPE: PRT
<213> ORGANISM: Homo sapiens

<400> SEQUENCE: 350

```
Arg Asn Trp Asn Lys Pro Ser Lys Arg Asn Cys Pro
1               5                   10
```

<210> SEQ ID NO 351
<211> LENGTH: 4
<212> TYPE: PRT
<213> ORGANISM: Homo sapiens

<400> SEQUENCE: 351

```
Arg Pro Gln Pro
1
```

<210> SEQ ID NO 352
<211> LENGTH: 48
<212> TYPE: PRT
<213> ORGANISM: Homo sapiens

<400> SEQUENCE: 352

```
Arg Pro Gln Thr Asp Leu Pro Arg Thr Asp Val Pro Gly Thr Leu Leu
1               5                   10                  15

Val Leu Arg Arg Ala Ala Ser Pro Trp Ser Pro Thr Arg Gly Asp Pro
                20                  25                  30

Ile Thr Cys Cys Leu Ile Thr Val Val Ile Ser Pro Arg Glu Gly Ala
                35                  40                  45
```

<210> SEQ ID NO 353
<211> LENGTH: 34
<212> TYPE: PRT
<213> ORGANISM: Homo sapiens

<400> SEQUENCE: 353

```
Arg Pro Thr Asp Arg Gln Thr Ser Pro Gly Gln Thr Ser Pro Ala Arg
1               5                   10                  15

Ser Leu Ser Ser Gly Gly Leu Arg Pro Pro Gly Val Gln Arg Gly Ala
                20                  25                  30

Thr Pro
```

<210> SEQ ID NO 354
<211> LENGTH: 5
<212> TYPE: PRT
<213> ORGANISM: Homo sapiens

<400> SEQUENCE: 354

```
Arg Gln Asp Cys Phe
1               5
```

<210> SEQ ID NO 355
<211> LENGTH: 10
<212> TYPE: PRT
<213> ORGANISM: Homo sapiens

<400> SEQUENCE: 355

```
Arg Arg Leu Leu Gly Leu Tyr Met Val Leu
1               5                   10
```

<210> SEQ ID NO 356
<211> LENGTH: 5
<212> TYPE: PRT
<213> ORGANISM: Homo sapiens

<400> SEQUENCE: 356

```
Arg Arg Arg Leu Trp
1               5
```

<210> SEQ ID NO 357
<211> LENGTH: 10
<212> TYPE: PRT
<213> ORGANISM: Homo sapiens

<400> SEQUENCE: 357

```
Arg Arg Ser Arg Pro Ser Trp Pro Thr Gly
1               5                   10
```

<210> SEQ ID NO 358
<211> LENGTH: 9
<212> TYPE: PRT
<213> ORGANISM: Homo sapiens

<400> SEQUENCE: 358

```
Arg Arg Trp Thr Lys Ala His Cys Lys
1               5
```

<210> SEQ ID NO 359
<211> LENGTH: 12
<212> TYPE: PRT
<213> ORGANISM: Homo sapiens

<400> SEQUENCE: 359

```
Arg Thr Leu Lys Ala Glu Val Glu Lys Gly Ser Met
1               5                   10
```

<210> SEQ ID NO 360
<211> LENGTH: 11
<212> TYPE: PRT
<213> ORGANISM: Homo sapiens

<400> SEQUENCE: 360

```
Arg Val Pro Phe Thr Phe Phe Asn Leu Ser Leu
1               5                   10
```

<210> SEQ ID NO 361
<211> LENGTH: 5
<212> TYPE: PRT
<213> ORGANISM: Homo sapiens

<400> SEQUENCE: 361

```
Ser Phe Ser Arg Gly
1               5
```

```
<210> SEQ ID NO 362
<211> LENGTH: 36
<212> TYPE: PRT
<213> ORGANISM: Homo sapiens

<400> SEQUENCE: 362

Ser Leu Ser Ser Thr His Phe Asp Ile Cys Ala Gly Ser Gly Gly Arg
1               5                   10                  15

Arg Ser Thr Lys Cys Lys Gly Leu Ser Thr Ser Val Gln Cys Val Tyr
            20                  25                  30

Glu Glu Ala His
        35

<210> SEQ ID NO 363
<211> LENGTH: 29
<212> TYPE: PRT
<213> ORGANISM: Homo sapiens

<400> SEQUENCE: 363

Ser Asn Glu Gly Leu Lys Glu Val Lys Ile Ser Thr Cys Arg Leu Ser
1               5                   10                  15

Lys Gln Ser Val Ser Lys Leu Leu Asn Glu Lys Lys Ser
            20                  25

<210> SEQ ID NO 364
<211> LENGTH: 36
<212> TYPE: PRT
<213> ORGANISM: Homo sapiens

<400> SEQUENCE: 364

Ser Asn Ser His Ser Pro Ser Thr Gln Gly Ser Leu Asp Cys Val Phe
1               5                   10                  15

Gln Glu Thr His Leu Ile Trp Ser Asp Phe Val Ser Pro Pro Lys Ser
            20                  25                  30

His Leu Glu Leu
        35

<210> SEQ ID NO 365
<211> LENGTH: 5
<212> TYPE: PRT
<213> ORGANISM: Homo sapiens

<400> SEQUENCE: 365

Ser Arg Arg Met Ala
1               5

<210> SEQ ID NO 366
<211> LENGTH: 24
<212> TYPE: PRT
<213> ORGANISM: Homo sapiens

<400> SEQUENCE: 366

Ser Arg Ser Ala Ser Phe Met Val Gly Thr Thr Thr Val Ser Asp Arg
1               5                   10                  15

Leu Arg Thr Ser Asp Phe Arg Ser
            20

<210> SEQ ID NO 367
<211> LENGTH: 15
<212> TYPE: PRT
<213> ORGANISM: Homo sapiens
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 367

Ser Xaa Ala Arg Xaa Pro Ile Gln Arg Glu Ser Arg Met Gly Asp
1               5                   10                  15

<210> SEQ ID NO 368
<211> LENGTH: 23
<212> TYPE: PRT
<213> ORGANISM: Homo sapiens

<400> SEQUENCE: 368

Thr Ile Pro Gly Leu Arg Thr Pro Val Ser Thr Arg Pro Thr Gly Thr
1               5                   10                  15

Val Pro Ile Pro Pro Ile Leu
            20

<210> SEQ ID NO 369
<211> LENGTH: 86
<212> TYPE: PRT
<213> ORGANISM: Homo sapiens

<400> SEQUENCE: 369

Thr Pro Thr Arg Asp Thr Ser Val Met Gln Ile Glu Glu Thr Gly Arg
1               5                   10                  15

Gly Lys Glu Ser Ser Thr Met Val Val Ala Thr Thr Ile His His Gly
            20                  25                  30

Glu Ala Thr Gly Thr Ile Ser Met Ser Ser Gly Thr Arg Thr Thr
        35                  40                  45

Ile Met Gly Thr Gly Asp Ile Trp Met Pro Thr Val Pro Glu Ala Ile
50                  55                  60

Asp Pro Thr Thr Cys Pro Glu Arg Gly Leu Met Thr Ser Thr Ser Leu
65                  70                  75                  80

Arg Pro His Ser Ser Asn
                85

<210> SEQ ID NO 370
<211> LENGTH: 14
<212> TYPE: PRT
<213> ORGANISM: Homo sapiens

<400> SEQUENCE: 370

Thr Arg Leu Ala Trp Asp Leu Asn Trp Lys Leu Asn Val Val
1               5                   10

<210> SEQ ID NO 371
<211> LENGTH: 12
<212> TYPE: PRT
<213> ORGANISM: Homo sapiens

<400> SEQUENCE: 371

Thr Arg Pro Pro Ser Gly Arg Arg Pro Pro Thr Ser
1               5                   10

<210> SEQ ID NO 372
<211> LENGTH: 6
```

```
<212> TYPE: PRT
<213> ORGANISM: Homo sapiens

<400> SEQUENCE: 372

Thr Val Leu Phe Gly Val
1               5

<210> SEQ ID NO 373
<211> LENGTH: 20
<212> TYPE: PRT
<213> ORGANISM: Homo sapiens

<400> SEQUENCE: 373

Val Ala Gln Arg Pro Ala Gly Pro Val Gly Trp Ala Ala Gly Gly Glu
1               5                   10                  15

Ala Leu Ile Gly
            20

<210> SEQ ID NO 374
<211> LENGTH: 11
<212> TYPE: PRT
<213> ORGANISM: Homo sapiens

<400> SEQUENCE: 374

Val Phe Glu Asp Leu Lys Lys Tyr Leu Lys Phe
1               5                   10

<210> SEQ ID NO 375
<211> LENGTH: 17
<212> TYPE: PRT
<213> ORGANISM: Homo sapiens

<400> SEQUENCE: 375

Val Phe Thr Val Val Ile Ser Thr Ser Gly Ala Arg Cys Gln Arg Gln
1               5                   10                  15

Tyr

<210> SEQ ID NO 376
<211> LENGTH: 30
<212> TYPE: PRT
<213> ORGANISM: Homo sapiens

<400> SEQUENCE: 376

Val Gly Ser Trp Glu Arg Ala Gly Gly Pro Arg Gly Glu Pro Pro
1               5                   10                  15

Pro Val Pro Ala Pro Cys Leu Ser Ala Pro Pro Arg Cys Ser
            20                  25                  30

<210> SEQ ID NO 377
<211> LENGTH: 5
<212> TYPE: PRT
<213> ORGANISM: Homo sapiens

<400> SEQUENCE: 377

Val Gly Thr Ile Tyr
1               5

<210> SEQ ID NO 378
<211> LENGTH: 8
<212> TYPE: PRT
<213> ORGANISM: Homo sapiens

<400> SEQUENCE: 378
```

```
Val Gly Val Gly Ile Ile Leu Ser
1               5

<210> SEQ ID NO 379
<211> LENGTH: 11
<212> TYPE: PRT
<213> ORGANISM: Homo sapiens

<400> SEQUENCE: 379

Val His Tyr His Asn Ile Asn Asn Leu Val Lys
1               5                   10

<210> SEQ ID NO 380
<211> LENGTH: 12
<212> TYPE: PRT
<213> ORGANISM: Homo sapiens

<400> SEQUENCE: 380

Val Ile Gly Ser Leu Met Gly Met Ala Leu Asn Leu
1               5                   10

<210> SEQ ID NO 381
<211> LENGTH: 35
<212> TYPE: PRT
<213> ORGANISM: Homo sapiens

<400> SEQUENCE: 381

Val Lys Lys Leu Val Val Gly Ser Trp Glu Arg Ala Gly Gly Pro Pro
1               5                   10                  15

Arg Gly Glu Pro Pro Val Pro Ala Pro Cys Leu Ser Ala Pro Pro
            20                  25                  30

Arg Cys Ser
        35

<210> SEQ ID NO 382
<211> LENGTH: 5
<212> TYPE: PRT
<213> ORGANISM: Homo sapiens

<400> SEQUENCE: 382

Val Lys Asn Tyr Phe
1               5

<210> SEQ ID NO 383
<211> LENGTH: 7
<212> TYPE: PRT
<213> ORGANISM: Homo sapiens

<400> SEQUENCE: 383

Val Leu Leu Tyr Leu Lys Arg
1               5

<210> SEQ ID NO 384
<211> LENGTH: 23
<212> TYPE: PRT
<213> ORGANISM: Homo sapiens

<400> SEQUENCE: 384

Val Pro Gly His Ala Arg Trp Leu Thr Pro Ile Ile Pro Ala Leu Arg
1               5                   10                  15

Asp Ala Glu Ala Gly Gly Ser
            20
```

```
<210> SEQ ID NO 385
<211> LENGTH: 10
<212> TYPE: PRT
<213> ORGANISM: Homo sapiens

<400> SEQUENCE: 385

Val Val Cys Ser Ile Ser Leu Leu Ser Phe
1               5                   10

<210> SEQ ID NO 386
<211> LENGTH: 5
<212> TYPE: PRT
<213> ORGANISM: Homo sapiens

<400> SEQUENCE: 386

Val Val Phe Leu Arg
1               5

<210> SEQ ID NO 387
<211> LENGTH: 30
<212> TYPE: PRT
<213> ORGANISM: Homo sapiens

<400> SEQUENCE: 387

Val Val Gln Thr Glu Ser Leu Lys Ser Pro Ser Thr Tyr Arg Cys Ala
1               5                   10                  15

Gln Gln Asp Gln Val Thr Ser Ser Asp Cys His His Lys
            20                  25                  30

<210> SEQ ID NO 388
<211> LENGTH: 10
<212> TYPE: PRT
<213> ORGANISM: Homo sapiens

<400> SEQUENCE: 388

Val Val Val Val Val Glu Thr Gly Ala Ile
1               5                   10

<210> SEQ ID NO 389
<211> LENGTH: 9
<212> TYPE: PRT
<213> ORGANISM: Homo sapiens

<400> SEQUENCE: 389

Val Tyr Gly Arg Asn Tyr Asp Gly Ile
1               5

<210> SEQ ID NO 390
<211> LENGTH: 33
<212> TYPE: PRT
<213> ORGANISM: Homo sapiens

<400> SEQUENCE: 390

Trp Glu Leu Asn Ser Glu Lys Thr Trp Thr Gln Gly Gly Glu His His
1               5                   10                  15

Thr Pro Gly Pro Leu Trp Gly Arg Gly Ala Arg Gly Ile Ala Leu
            20                  25                  30

Gly

<210> SEQ ID NO 391
<211> LENGTH: 8
<212> TYPE: PRT
<213> ORGANISM: Homo sapiens
```

-continued

```
<400> SEQUENCE: 391

Trp Lys Lys Asn Ser Arg Cys Tyr
1               5

<210> SEQ ID NO 392
<211> LENGTH: 6
<212> TYPE: PRT
<213> ORGANISM: Homo sapiens

<400> SEQUENCE: 392

Trp Lys Ser Gly Arg Ser
1               5

<210> SEQ ID NO 393
<211> LENGTH: 16
<212> TYPE: PRT
<213> ORGANISM: Homo sapiens

<400> SEQUENCE: 393

Trp Met Gln Ser Lys Tyr Ser Lys Lys Ser Cys Cys Tyr Val Tyr Gly
1               5                   10                  15

<210> SEQ ID NO 394
<211> LENGTH: 20
<212> TYPE: PRT
<213> ORGANISM: Homo sapiens

<400> SEQUENCE: 394

Trp Pro Pro Glu Leu Arg Leu Leu Thr Asp Gln Trp Gln His Ser Ile
1               5                   10                  15

Leu Met Gly Met
            20

<210> SEQ ID NO 395
<211> LENGTH: 17
<212> TYPE: PRT
<213> ORGANISM: Homo sapiens

<400> SEQUENCE: 395

Trp Pro Pro Ser Ser Gly Pro Asp Cys Arg Phe Thr His Ala Ile Lys
1               5                   10                  15

Leu

<210> SEQ ID NO 396
<211> LENGTH: 13
<212> TYPE: PRT
<213> ORGANISM: Homo sapiens

<400> SEQUENCE: 396

Trp Arg Ser Ser Phe Pro Ser Thr Ile Tyr Gly Lys Asp
1               5                   10

<210> SEQ ID NO 397
<211> LENGTH: 6
<212> TYPE: PRT
<213> ORGANISM: Homo sapiens

<400> SEQUENCE: 397

Trp Ser Gly Trp Pro Thr
1               5

<210> SEQ ID NO 398
<211> LENGTH: 20
```

```
<212> TYPE: PRT
<213> ORGANISM: Homo sapiens

<400> SEQUENCE: 398

Tyr Trp Thr Asn Pro Pro Thr Leu Thr Ile Pro Arg His His Leu Ser
1               5                   10                  15

Thr Val Leu Ala
            20

<210> SEQ ID NO 399
<211> LENGTH: 4
<212> TYPE: PRT
<213> ORGANISM: Homo sapiens

<400> SEQUENCE: 399

Asn Ser Ser Val
1

<210> SEQ ID NO 400
<211> LENGTH: 134
<212> TYPE: PRT
<213> ORGANISM: Homo sapiens

<400> SEQUENCE: 400

Arg Cys Glu Gly Ile Asn Ile Ser Gly Asn Phe Tyr Arg Asn Lys Leu
1               5                   10                  15

Lys Tyr Leu Ala Phe Leu Arg Lys Arg Met Asn Thr Asn Pro Ser Arg
            20                  25                  30

Gly Pro Tyr His Phe Arg Ala Pro Ser Arg Ile Phe Trp Arg Thr Val
        35                  40                  45

Arg Gly Met Leu Pro His Lys Thr Lys Arg Gly Gln Ala Ala Leu Asp
    50                  55                  60

Arg Leu Lys Val Phe Asp Gly Ile Pro Pro Tyr Asp Lys Lys
65                  70                  75                  80

Ala Asp Gly Gly Ser Cys Cys Pro Gln Gly Arg Ala Ser Glu Ala Tyr
                85                  90                  95

Lys Lys Val Cys Leu Ser Gly Ala Pro Gly Ser Arg Gly Trp Leu Glu
            100                 105                 110

Val Pro Gly Ser Asp Ser His Pro Gly Gly Glu Glu Gly Ala Cys Gly
        115                 120                 125

Arg Thr Arg Val Thr Ser
    130

<210> SEQ ID NO 401
<211> LENGTH: 66
<212> TYPE: PRT
<213> ORGANISM: Homo sapiens

<400> SEQUENCE: 401

Ser Ser Ile Thr Val Thr Ser Glu Val Pro Phe Ser Lys Arg Tyr Leu
1               5                   10                  15

Lys Tyr Leu Thr Lys Lys Tyr Leu Lys Lys Asn Asn Leu Arg Asp Trp
            20                  25                  30

Leu Arg Val Val Ala Asn Ser Lys Glu Ser Tyr Glu Leu Arg Tyr Phe
        35                  40                  45

Gln Ile Asn Gln Asp Glu Glu Glu Glu Ser Leu Arg Pro His Ser
    50                  55                  60

Ser Asn
65
```

<210> SEQ ID NO 402
<211> LENGTH: 77
<212> TYPE: PRT
<213> ORGANISM: Homo sapiens

<400> SEQUENCE: 402

Pro Ala Ser Ala Ser Ile Leu Ala Gly Val Pro Met Tyr Arg Asn Glu
1               5                   10                  15

Phe Thr Ala Trp Tyr Arg Arg Met Ser Val Val Tyr Gly Ile Gly Thr
            20                  25                  30

Trp Ser Val Leu Gly Ser Leu Leu Tyr Tyr Ser Arg Thr Met Ala Lys
        35                  40                  45

Ser Ser Val Asp Gln Lys Asp Gly Ser Ala Ser Glu Val Pro Ser Glu
50                  55                  60

Leu Ser Glu Arg Pro Ser Leu Arg Pro His Ser Ser Asn
65                  70                  75

<210> SEQ ID NO 403
<211> LENGTH: 124
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 403

Gln Thr Lys Glu Glu Arg Ile Ser Gln Xaa Glu Ile Met Ser Gly Ala
1               5                   10                  15

Arg Thr Ala Ser Thr Pro Thr Pro Pro Gln Thr Gly Gly Gly Leu Glu
            20                  25                  30

Pro Gln Ala Asn Gly Glu Thr Pro Gln Val Ala Val Ile Val Arg Pro
        35                  40                  45

Asp Asp Arg Ser Gln Gly Ala Ile Ile Ala Asp Arg Pro Gly Leu Pro
50                  55                  60

Gly Pro Glu His Ser Pro Ser Glu Ser Gln Pro Ser Pro Ser Ser Pro
65                  70                  75                  80

Thr Pro Ser Pro Ser Pro Val Leu Glu Pro Gly Ser Glu Pro Asn Leu
                85                  90                  95

Ala Val Leu Ser Ile Pro Gly Asp Thr Met Thr Thr Ile Gln Met Ser
            100                 105                 110

Val Glu Glu Ala Cys Gly Arg Thr Arg Val Thr Ser
        115                 120

<210> SEQ ID NO 404
<211> LENGTH: 91
<212> TYPE: PRT
<213> ORGANISM: Homo sapiens

<400> SEQUENCE: 404

Ser Ser Glu Ser Arg Pro Met Ser Tyr Asp Glu Lys Arg Gln Leu Ser
1               5                   10                  15

Leu Asp Ile Asn Lys Leu Pro Gly Glu Lys Leu Gly Arg Val Val His
            20                  25                  30

Ile Ile Gln Ala Arg Glu Pro Ser Leu Arg Asp Ser Asn Pro Glu Glu
        35                  40                  45

Ile Glu Ile Asp Phe Glu Thr Leu Lys Pro Ser Thr Leu Arg Glu Leu
50                  55                  60

```
Glu Arg Tyr Val Leu Ser Cys Leu Arg Lys Lys Pro Arg Lys Pro Tyr
 65                  70                  75                  80

Ser Thr Tyr Glu Met Arg Phe Ile Ser Trp Phe
                 85                  90

<210> SEQ ID NO 405
<211> LENGTH: 44
<212> TYPE: PRT
<213> ORGANISM: Homo sapiens

<400> SEQUENCE: 405

Ile Leu Tyr Pro Glu Thr Leu Leu Lys Leu Leu Ile Ser Leu Arg Arg
 1               5                  10                  15

Phe Trp Ala Glu Met Met Glu Phe Ser Arg Tyr Thr Ile Met Ser Ser
             20                  25                  30

Glu Asn Arg Asp Asn Leu Thr Ser Ser Phe Pro Asn
             35                  40

<210> SEQ ID NO 406
<211> LENGTH: 22
<212> TYPE: PRT
<213> ORGANISM: Homo sapiens

<400> SEQUENCE: 406

Arg Glu Met Val Pro Arg Met Arg Thr Ser Arg Ala Ser Ile His
 1               5                  10                  15

His Ile Lys Pro Thr Glu
             20

<210> SEQ ID NO 407
<211> LENGTH: 32
<212> TYPE: PRT
<213> ORGANISM: Homo sapiens

<400> SEQUENCE: 407

Gly Val Gly Gly Arg Gly Gly Gly Gly Gly Gly Gly Arg Gly Ala
 1               5                  10                  15

Gly Gly Gly Arg Gly Ala Gly Ala Gly Gly Arg Pro Glu Ala Ala
             20                  25                  30

<210> SEQ ID NO 408
<211> LENGTH: 97
<212> TYPE: PRT
<213> ORGANISM: Homo sapiens

<400> SEQUENCE: 408

Lys Ala Glu Cys Phe Lys Asn Leu Ile Val Lys Gln Lys Ser Leu
 1               5                  10                  15

Cys Ser Gly Glu Lys Glu His Leu Asn Glu Ala Ser Ile Leu Ala Gln
             20                  25                  30

Val Ser Val Ser Ser Ser Lys Arg Val Trp Lys Ser Trp Glu Asn Leu
         35                  40                  45

Ile Ser Ser Phe Met Val Trp Asn Pro Ala His Ile Ile Ser Ile
     50                  55                  60

Pro Asn Leu Glu Lys Thr Ser Asp Leu Ser Met Met Ser Lys Leu Ile
 65                  70                  75                  80

Phe Leu Leu Gly Ser Arg Arg Phe Phe Arg Ser Ser Pro Arg Gly Ile
                 85                  90                  95

Phe
```

<210> SEQ ID NO 409
<211> LENGTH: 52
<212> TYPE: PRT
<213> ORGANISM: Homo sapiens

<400> SEQUENCE: 409

```
Arg Met Pro Lys Glu Pro Leu Lys Ile Pro Val Ala Thr Ser Arg Thr
1               5                   10                  15

Gln Ala Ser Leu Gly Lys Gln Lys Cys Arg Arg Arg Ile Met Met Ser
                20                  25                  30

Leu Arg Gln Arg Trp Gln Met Gly Ile Ser Trp Met Gly Arg Leu Lys
            35                  40                  45

Pro Thr Gln Trp
        50
```

<210> SEQ ID NO 410
<211> LENGTH: 19
<212> TYPE: PRT
<213> ORGANISM: Homo sapiens

<400> SEQUENCE: 410

```
Glu Gly Ser Val Tyr Gln Cys Cys Glu Lys Gly Lys Lys Gln Val Cys
1               5                   10                  15

Ser Gln Arg
```

<210> SEQ ID NO 411
<211> LENGTH: 81
<212> TYPE: PRT
<213> ORGANISM: Homo sapiens

<400> SEQUENCE: 411

```
Gln Ser Ser Val Ala Leu Thr Asn Pro Glu Ser Tyr His Ile Leu Lys
1               5                   10                  15

Pro Lys Leu Glu Ala Asp Leu Arg Trp Leu Lys Leu Arg Lys Arg Lys
                20                  25                  30

Gln Val Ser Lys Leu Leu Val Leu Ser Cys Cys Leu Leu Lys Asn Leu
            35                  40                  45

Gly Phe Trp Lys Gly Arg Met Gly Lys Thr Gln Gln Arg Tyr Ala Arg
        50                  55                  60

Leu Thr Leu Trp Arg Leu Trp Thr Leu Gln Val Gln Pro Ser Thr Leu
65                  70                  75                  80

Thr
```

<210> SEQ ID NO 412
<211> LENGTH: 30
<212> TYPE: PRT
<213> ORGANISM: Homo sapiens

<400> SEQUENCE: 412

```
Gln Lys Leu Cys Gln Ala Lys Glu Lys Gly Met Cys Met Lys Lys Leu
1               5                   10                  15

Arg Met Leu Trp Glu Cys Gln Lys Leu Tyr Ser Leu Gly Phe
                20                  25                  30
```

<210> SEQ ID NO 413
<211> LENGTH: 55
<212> TYPE: PRT
<213> ORGANISM: Homo sapiens

```
<400> SEQUENCE: 413

Ala Pro Arg Thr Arg Thr Leu Arg Ala Arg Arg Ser Pro Arg Met Glu
1               5                   10                  15

Ile Ala Gln Lys Trp Met Met Lys Thr Val Lys Glu Glu Glu Trp Asn
            20                  25                  30

Val Trp Met Lys Cys Pro Ile Leu Lys Asn Ser Leu Pro Ile Ser Lys
        35                  40                  45

Ile Asn Phe Ile Lys Asn Asp
    50                  55

<210> SEQ ID NO 414
<211> LENGTH: 48
<212> TYPE: PRT
<213> ORGANISM: Homo sapiens

<400> SEQUENCE: 414

Pro Asn Thr Phe Ser Ile Ser Ser Glu Gly Asn Ser Asp Val Gln Thr
1               5                   10                  15

Asn Phe Asn Lys Arg Ile Lys Arg Phe Ile Trp Val His Gly Pro Gln
            20                  25                  30

Trp Leu Leu Pro Gln Lys Gly Glu Arg Asn Thr Arg Val Asp Asp Phe
        35                  40                  45

<210> SEQ ID NO 415
<211> LENGTH: 38
<212> TYPE: PRT
<213> ORGANISM: Homo sapiens

<400> SEQUENCE: 415

Pro Phe Cys Lys Phe Arg Ile Leu Ser Pro Arg Cys Leu Ser Asp Ala
1               5                   10                  15

Thr Gln Trp Pro Phe Lys Val Leu Phe Lys Trp Asp Cys Ser Ser Asn
            20                  25                  30

Ser Phe Leu Gly Pro Asn
        35

<210> SEQ ID NO 416
<211> LENGTH: 11
<212> TYPE: PRT
<213> ORGANISM: Homo sapiens

<400> SEQUENCE: 416

Asn Asn Val Ser Ala Leu Leu Gly Trp Gln Lys
1               5                   10

<210> SEQ ID NO 417
<211> LENGTH: 12
<212> TYPE: PRT
<213> ORGANISM: Homo sapiens

<400> SEQUENCE: 417

Gln Ser Gln His Gly Gly Pro Glu Asn Phe Lys Ile
1               5                   10

<210> SEQ ID NO 418
<211> LENGTH: 11
<212> TYPE: PRT
<213> ORGANISM: Homo sapiens

<400> SEQUENCE: 418

Leu Val Ser Ile Leu Leu Thr Lys Thr Ile Tyr
```

-continued

```
1               5                   10

<210> SEQ ID NO 419
<211> LENGTH: 14
<212> TYPE: PRT
<213> ORGANISM: Homo sapiens

<400> SEQUENCE: 419

Glu Phe Phe Ala Thr Phe Pro Thr Pro Lys Gln His Gly Ala
1               5                   10

<210> SEQ ID NO 420
<211> LENGTH: 41
<212> TYPE: PRT
<213> ORGANISM: Homo sapiens

<400> SEQUENCE: 420

Ile Leu Tyr Pro Glu Thr Leu Leu Lys Leu Leu Ile Ser Leu Arg Arg
1               5                   10                  15

Phe Trp Ala Glu Met Asn Glu Phe Ser Arg Tyr Thr Ile Asn Ser Ser
            20                  25                  30

Glu Asn Arg Asp Asn Leu Thr Ser Ser
        35                  40

<210> SEQ ID NO 421
<211> LENGTH: 31
<212> TYPE: PRT
<213> ORGANISM: Homo sapiens

<400> SEQUENCE: 421

Ile Leu Tyr Pro Leu Leu Lys Leu Leu Ile Ser Leu Arg Phe Glu Asn
1               5                   10                  15

Glu Phe Ser Arg Tyr Ile Asn Ser Ser Asn Asp Asn Thr Ser Ser
            20                  25                  30

<210> SEQ ID NO 422
<211> LENGTH: 41
<212> TYPE: PRT
<213> ORGANISM: Homo sapiens

<400> SEQUENCE: 422

Ile Leu Tyr Pro Gln Ala Leu Leu Lys Leu Leu Ile Ser Leu Arg Ser
1               5                   10                  15

Phe Cys Thr Glu Thr Asn Glu Phe Ser Arg Tyr Arg Ile Asn Ser Ser
            20                  25                  30

Ala Asn Lys Asp Asn Asn Thr Ser Ser
        35                  40

<210> SEQ ID NO 423
<211> LENGTH: 18
<212> TYPE: PRT
<213> ORGANISM: Homo sapiens

<400> SEQUENCE: 423

Met Val Pro Arg Met Arg Arg Thr Ser Arg Ala Ser Ile His His Ile
1               5                   10                  15

Lys Pro

<210> SEQ ID NO 424
<211> LENGTH: 13
<212> TYPE: PRT
<213> ORGANISM: Homo sapiens
```

<400> SEQUENCE: 424

Met Val Pro Met Arg Ser Ser Ile His His Ile Lys Pro
1               5                   10

<210> SEQ ID NO 425
<211> LENGTH: 18
<212> TYPE: PRT
<213> ORGANISM: Homo sapiens

<400> SEQUENCE: 425

Met Val Pro Cys Met His Arg Ser Ser Gln Thr Ser Ile His His Ile
1               5                   10                  15

Lys Pro

<210> SEQ ID NO 426
<211> LENGTH: 31
<212> TYPE: PRT
<213> ORGANISM: Homo sapiens

<400> SEQUENCE: 426

Gly Val Gly Gly Arg Gly Gly Gly Gly Gly Gly Arg Gly Ala
1               5                   10                  15

Gly Gly Gly Arg Gly Ala Gly Ala Gly Gly Arg Pro Glu Ala
            20                  25                  30

<210> SEQ ID NO 427
<211> LENGTH: 22
<212> TYPE: PRT
<213> ORGANISM: Homo sapiens

<400> SEQUENCE: 427

Gly Gly Gly Gly Gly Gly Gly Gly Gly Gly Gly Gly Gly Gly
1               5                   10                  15

Gly Gly Gly Gly Glu Ala
            20

<210> SEQ ID NO 428
<211> LENGTH: 29
<212> TYPE: PRT
<213> ORGANISM: Homo sapiens

<400> SEQUENCE: 428

Gly Gly Gly Gly Gly Gly Gly Gly Gly Gly Gly Gly Gly Gly
1               5                   10                  15

Gly Gly Gly Gly Gly Gly Gly Gly Gly Gly Gly Glu Ala
            20                  25

<210> SEQ ID NO 429
<211> LENGTH: 22
<212> TYPE: PRT
<213> ORGANISM: Homo sapiens

<400> SEQUENCE: 429

Ile Val Lys Lys Gln Lys Ser Leu Cys Ser Gly Glu Lys Glu His Leu
1               5                   10                  15

Asn Glu Ala Ser Ile Leu
            20

<210> SEQ ID NO 430
<211> LENGTH: 14
<212> TYPE: PRT

```
<213> ORGANISM: Homo sapiens

<400> SEQUENCE: 430

Ile Lys Lys Lys Cys Gly Lys Glu His Asn Glu Ser Ile Leu
1               5                   10

<210> SEQ ID NO 431
<211> LENGTH: 21
<212> TYPE: PRT
<213> ORGANISM: Homo sapiens

<400> SEQUENCE: 431

Ile Ile Lys Lys Ser Lys Cys Arg Gly Lys Glu His Met Ile Gln Asn
1               5                   10                  15

Glu Val Ser Ile Leu
            20

<210> SEQ ID NO 432
<211> LENGTH: 19
<212> TYPE: PRT
<213> ORGANISM: Homo sapiens

<400> SEQUENCE: 432

Pro Leu Lys Ile Pro Val Ala Thr Ser Arg Thr Gln Ala Ser Leu Gly
1               5                   10                  15

Lys Gln Lys

<210> SEQ ID NO 433
<211> LENGTH: 16
<212> TYPE: PRT
<213> ORGANISM: Homo sapiens

<400> SEQUENCE: 433

Pro Leu Lys Ile Pro Ala Thr Ser Arg Thr Ala Ser Leu Lys Gln Lys
1               5                   10                  15

<210> SEQ ID NO 434
<211> LENGTH: 28
<212> TYPE: PRT
<213> ORGANISM: Homo sapiens

<400> SEQUENCE: 434

Pro Leu Lys Ile Pro Pro Ala Arg Val Thr Leu Thr Ser Arg Thr Thr
1               5                   10                  15

Ala Gly Ala Ala Ser Leu Thr Lys Trp Ile Gln Lys
            20                  25

<210> SEQ ID NO 435
<211> LENGTH: 8
<212> TYPE: PRT
<213> ORGANISM: Homo sapiens

<400> SEQUENCE: 435

Cys Cys Glu Lys Gly Lys Lys Gln
1               5

<210> SEQ ID NO 436
<211> LENGTH: 7
<212> TYPE: PRT
<213> ORGANISM: Homo sapiens

<400> SEQUENCE: 436

Cys Cys Glu Lys Gly Lys Gln
```

```
<210> SEQ ID NO 437
<211> LENGTH: 8
<212> TYPE: PRT
<213> ORGANISM: Homo sapiens

<400> SEQUENCE: 437

Cys Cys Glu Lys Gly Lys Arg Gln
1               5

<210> SEQ ID NO 438
<211> LENGTH: 22
<212> TYPE: PRT
<213> ORGANISM: Homo sapiens

<400> SEQUENCE: 438

Gln Ser Ser Val Ala Leu Thr Asn Pro Glu Ser Tyr His Ile Leu Lys
1               5                   10                  15

Pro Lys Leu Glu Ala Asp
            20

<210> SEQ ID NO 439
<211> LENGTH: 12
<212> TYPE: PRT
<213> ORGANISM: Homo sapiens

<400> SEQUENCE: 439

Gln Ser Ser Val Ala Leu Pro Ser Lys Pro Leu Asp
1               5                   10

<210> SEQ ID NO 440
<211> LENGTH: 18
<212> TYPE: PRT
<213> ORGANISM: Homo sapiens

<400> SEQUENCE: 440

Gln Ser Ser Val Ala Leu Ser Thr Pro Ile Ser Lys Pro Gln Leu Asp
1               5                   10                  15

Thr Asp

<210> SEQ ID NO 441
<211> LENGTH: 11
<212> TYPE: PRT
<213> ORGANISM: Homo sapiens

<400> SEQUENCE: 441

Gln Lys Leu Cys Gln Ala Lys Glu Lys Gly Asn
1               5                   10

<210> SEQ ID NO 442
<211> LENGTH: 8
<212> TYPE: PRT
<213> ORGANISM: Homo sapiens

<400> SEQUENCE: 442

Lys Leu Cys Gln Ala Glu Gly Asn
1               5

<210> SEQ ID NO 443
<211> LENGTH: 11
<212> TYPE: PRT
<213> ORGANISM: Homo sapiens
```

```
<400> SEQUENCE: 443

Glu Lys Leu Cys Gln Ala Leu Glu Asn Gly Asn
1               5                   10

<210> SEQ ID NO 444
<211> LENGTH: 19
<212> TYPE: PRT
<213> ORGANISM: Homo sapiens

<400> SEQUENCE: 444

Pro Arg Thr Arg Thr Leu Arg Ala Arg Arg Ser Pro Arg Asn Glu Ile
1               5                   10                  15

Ala Gln Lys

<210> SEQ ID NO 445
<211> LENGTH: 13
<212> TYPE: PRT
<213> ORGANISM: Homo sapiens

<400> SEQUENCE: 445

Pro Thr Arg Thr Leu Arg Pro Arg Asn Glu Ala Gln Lys
1               5                   10

<210> SEQ ID NO 446
<211> LENGTH: 16
<212> TYPE: PRT
<213> ORGANISM: Homo sapiens

<400> SEQUENCE: 446

Pro Thr Thr Arg Thr Leu Arg Pro Arg Asn Glu Ala Pro Ala Gln Lys
1               5                   10                  15

<210> SEQ ID NO 447
<211> LENGTH: 13
<212> TYPE: PRT
<213> ORGANISM: Homo sapiens

<400> SEQUENCE: 447

Pro Gln Trp Leu Leu Pro Gln Lys Gly Glu Arg Asn Thr
1               5                   10

<210> SEQ ID NO 448
<211> LENGTH: 9
<212> TYPE: PRT
<213> ORGANISM: Homo sapiens

<400> SEQUENCE: 448

Pro Trp Leu Leu Gln Lys Arg Asn Thr
1               5

<210> SEQ ID NO 449
<211> LENGTH: 11
<212> TYPE: PRT
<213> ORGANISM: Homo sapiens

<400> SEQUENCE: 449

Pro Arg Trp Leu Leu Ser Gln Lys Arg Asn Thr
1               5                   10

<210> SEQ ID NO 450
<211> LENGTH: 11
<212> TYPE: PRT
<213> ORGANISM: Homo sapiens
```

```
<400> SEQUENCE: 450

Pro Arg Cys Leu Ser Asp Ala Thr Gln Trp Pro
1               5                   10

<210> SEQ ID NO 451
<211> LENGTH: 8
<212> TYPE: PRT
<213> ORGANISM: Homo sapiens

<400> SEQUENCE: 451

Pro Arg Cys Leu Ala Gln Trp Pro
1               5

<210> SEQ ID NO 452
<211> LENGTH: 10
<212> TYPE: PRT
<213> ORGANISM: Homo sapiens

<400> SEQUENCE: 452

Pro Arg Cys Leu His Ala Ser Gln Trp Pro
1               5                   10

<210> SEQ ID NO 453
<211> LENGTH: 9
<212> TYPE: PRT
<213> ORGANISM: Homo sapiens

<400> SEQUENCE: 453

Val Ser Ala Leu Leu Gly Trp Gln Lys
1               5

<210> SEQ ID NO 454
<211> LENGTH: 6
<212> TYPE: PRT
<213> ORGANISM: Homo sapiens

<400> SEQUENCE: 454

Val Leu Leu Gly Trp Lys
1               5

<210> SEQ ID NO 455
<211> LENGTH: 9
<212> TYPE: PRT
<213> ORGANISM: Homo sapiens

<400> SEQUENCE: 455

Val Thr Ser Leu Leu Gly Trp Glu Lys
1               5

<210> SEQ ID NO 456
<211> LENGTH: 6
<212> TYPE: PRT
<213> ORGANISM: Homo sapiens

<400> SEQUENCE: 456

Pro Glu Asn Phe Lys Ile
1               5

<210> SEQ ID NO 457
<211> LENGTH: 6
<212> TYPE: PRT
<213> ORGANISM: Homo sapiens

<400> SEQUENCE: 457
```

```
Pro Glu Asn Phe Lys Ile
1               5

<210> SEQ ID NO 458
<211> LENGTH: 6
<212> TYPE: PRT
<213> ORGANISM: Homo sapiens

<400> SEQUENCE: 458

Pro Glu Asn Phe Lys Ile
1               5

<210> SEQ ID NO 459
<211> LENGTH: 7
<212> TYPE: PRT
<213> ORGANISM: Homo sapiens

<400> SEQUENCE: 459

Leu Leu Thr Lys Thr Ile Tyr
1               5

<210> SEQ ID NO 460
<211> LENGTH: 6
<212> TYPE: PRT
<213> ORGANISM: Homo sapiens

<400> SEQUENCE: 460

Leu Leu Thr Lys Thr Tyr
1               5

<210> SEQ ID NO 461
<211> LENGTH: 7
<212> TYPE: PRT
<213> ORGANISM: Homo sapiens

<400> SEQUENCE: 461

Leu Leu Thr Lys Thr Val Tyr
1               5

<210> SEQ ID NO 462
<211> LENGTH: 6
<212> TYPE: PRT
<213> ORGANISM: Homo sapiens

<400> SEQUENCE: 462

Phe Ala Thr Phe Pro Thr
1               5

<210> SEQ ID NO 463
<211> LENGTH: 6
<212> TYPE: PRT
<213> ORGANISM: Homo sapiens

<400> SEQUENCE: 463

Phe Ala Thr Phe Pro Thr
1               5

<210> SEQ ID NO 464
<211> LENGTH: 6
<212> TYPE: PRT
<213> ORGANISM: Homo sapiens

<400> SEQUENCE: 464

Phe Ala Thr Phe Pro Thr
1               5
```

```
<210> SEQ ID NO 465
<211> LENGTH: 15
<212> TYPE: PRT
<213> ORGANISM: Homo sapiens

<400> SEQUENCE: 465

Ala Gln Ser Arg Ser Arg Ser Arg Arg Gln Ser Pro Trp Pro Pro
1               5                   10                  15

<210> SEQ ID NO 466
<211> LENGTH: 52
<212> TYPE: PRT
<213> ORGANISM: Homo sapiens

<400> SEQUENCE: 466

Ala Val Ala Gln Met Arg Met Arg Met Lys Met Arg Met Arg Met Gly
1               5                   10                  15

Gln Glu Gly Thr Gln Gln Glu Pro Gln Gln Gln Asn Ile Leu Glu Asp
            20                  25                  30

Asp Thr Arg Asp Gln Gly Ala His Thr Gly Gly Pro Gly Lys Pro
        35                  40                  45

Asp Ala Asp Glu
    50

<210> SEQ ID NO 467
<211> LENGTH: 16
<212> TYPE: PRT
<213> ORGANISM: Homo sapiens

<400> SEQUENCE: 467

Glu His Ile Pro Ala Pro Ala Ser Pro Arg Phe Ser Ile Gln Gly Ser
1               5                   10                  15

<210> SEQ ID NO 468
<211> LENGTH: 15
<212> TYPE: PRT
<213> ORGANISM: Homo sapiens

<400> SEQUENCE: 468

Glu Asn Val Ser Phe Lys Lys Thr Lys Met Phe Phe Trp His Asn
1               5                   10                  15

<210> SEQ ID NO 469
<211> LENGTH: 59
<212> TYPE: PRT
<213> ORGANISM: Homo sapiens

<400> SEQUENCE: 469

Gly Phe Ile Arg Ser Ser Ser Pro Phe Lys Leu Ser Leu Ala Tyr Cys
1               5                   10                  15

His Val Lys Leu Ala Cys Leu Pro Phe Phe His Asp Cys Lys Phe Pro
            20                  25                  30

Glu Ala Ser Pro Ala Met Gln Asn Ser Glu Ser Ile Lys Pro Leu Ser
        35                  40                  45

Phe Ile Asn Tyr Pro Val Phe Gly Met Ser Leu
    50                  55

<210> SEQ ID NO 470
<211> LENGTH: 26
<212> TYPE: PRT
<213> ORGANISM: Homo sapiens
```

```
<400> SEQUENCE: 470

Gly His Ala Asn Val Thr Arg Thr Asn Pro Ala Phe Val His Lys Val
1               5                   10                  15

Thr Val Thr Gln Asn Gly Lys Trp Ala Leu
            20                  25

<210> SEQ ID NO 471
<211> LENGTH: 8
<212> TYPE: PRT
<213> ORGANISM: Homo sapiens

<400> SEQUENCE: 471

Gly Asn Arg Asp Pro Val Ala Cys
1               5

<210> SEQ ID NO 472
<211> LENGTH: 30
<212> TYPE: PRT
<213> ORGANISM: Homo sapiens

<400> SEQUENCE: 472

Ile Ile Ser Arg Arg Gly Thr Asn Thr Ala Pro Leu Thr Ser Ser
1               5                   10                  15

Ala Thr Thr Arg Thr Pro Ala Arg Leu Trp Cys Cys Arg Ser
            20                  25                  30

<210> SEQ ID NO 473
<211> LENGTH: 12
<212> TYPE: PRT
<213> ORGANISM: Homo sapiens

<400> SEQUENCE: 473

Ile Gln Cys Val Tyr Lys Pro Asn Ser His Phe Val
1               5                   10

<210> SEQ ID NO 474
<211> LENGTH: 19
<212> TYPE: PRT
<213> ORGANISM: Homo sapiens

<400> SEQUENCE: 474

Leu Phe Tyr Gly Gly Met Gly Gly Trp Lys Asn Gly Ser Arg Ala Ser
1               5                   10                  15

Glu Ala Asp

<210> SEQ ID NO 475
<211> LENGTH: 11
<212> TYPE: PRT
<213> ORGANISM: Homo sapiens

<400> SEQUENCE: 475

Asn Ser Phe Leu Glu Gly Glu Glu Gln Ile Leu
1               5                   10

<210> SEQ ID NO 476
<211> LENGTH: 5
<212> TYPE: PRT
<213> ORGANISM: Homo sapiens

<400> SEQUENCE: 476

Asn Ser Gln Trp Leu
1               5
```

```
<210> SEQ ID NO 477
<211> LENGTH: 54
<212> TYPE: PRT
<213> ORGANISM: Homo sapiens
<220> FEATURE:
<221> NAME/KEY: NON_CONS
<222> LOCATION: (28)..(29)

<400> SEQUENCE: 477

Pro Gly Leu Ile Pro Gly Phe Thr Pro Gly Leu Gly Ala Leu Gly Ser
1               5                   10                  15

Thr Gly Gly Ser Ser Gly Thr Asn Gly Ser Asn Glu Ala Asn Leu Gln
            20                  25                  30

Ala Leu Ile Ala Thr Gly Gly Asp Ile Asn Ala Ala Ile Glu Arg Leu
        35                  40                  45

Leu Gly Ser Gln Pro Ser
    50

<210> SEQ ID NO 478
<211> LENGTH: 10
<212> TYPE: PRT
<213> ORGANISM: Homo sapiens

<400> SEQUENCE: 478

Pro Gln Cys Arg Glu Lys Thr Lys Phe Asn
1               5                   10

<210> SEQ ID NO 479
<211> LENGTH: 14
<212> TYPE: PRT
<213> ORGANISM: Homo sapiens

<400> SEQUENCE: 479

Pro Thr Leu Cys Val Pro Glu Ser Ala Pro Lys Cys Trp Gln
1               5                   10

<210> SEQ ID NO 480
<211> LENGTH: 6
<212> TYPE: PRT
<213> ORGANISM: Homo sapiens

<400> SEQUENCE: 480

Gln Ala Tyr Val Asn Val
1               5

<210> SEQ ID NO 481
<211> LENGTH: 21
<212> TYPE: PRT
<213> ORGANISM: Homo sapiens

<400> SEQUENCE: 481

Gln His Thr Asn Met Ala His Val Tyr Ile Cys Asn Lys Pro Ala Cys
1               5                   10                  15

Cys Ala Gln Val Pro
            20

<210> SEQ ID NO 482
<211> LENGTH: 30
<212> TYPE: PRT
<213> ORGANISM: Homo sapiens

<400> SEQUENCE: 482
```

-continued

```
Gln Ile Ile Lys Leu Asn Lys Gly Val Val Ile Asn Ile Ile Met Glu
1               5                   10                  15

Val Arg Met Ala Ala Arg Asp Gly Gly Leu Phe Ser Val Ile
                20                  25                  30

<210> SEQ ID NO 483
<211> LENGTH: 42
<212> TYPE: PRT
<213> ORGANISM: Homo sapiens

<400> SEQUENCE: 483

Arg Asn Pro Val Ser Met Lys Asn Ala Lys Lys Ile Ser Trp Ala Trp
1               5                   10                  15

Trp His Thr Ser Val Val Ser Ser Thr Gln Glu Val Glu Ala Gly Glu
                20                  25                  30

Leu Leu Glu Pro Gly Arg Arg Arg Leu Gln
            35                  40

<210> SEQ ID NO 484
<211> LENGTH: 11
<212> TYPE: PRT
<213> ORGANISM: Homo sapiens

<400> SEQUENCE: 484

Thr Met Pro Lys Gly Asn Val Lys Leu Gly Asn
1               5                   10

<210> SEQ ID NO 485
<211> LENGTH: 17
<212> TYPE: PRT
<213> ORGANISM: Homo sapiens

<400> SEQUENCE: 485

Thr Met Thr Asn Gln Thr Asn Leu Lys Thr Asn Asp Asn His Thr Gln
1               5                   10                  15

His

<210> SEQ ID NO 486
<211> LENGTH: 23
<212> TYPE: PRT
<213> ORGANISM: Homo sapiens

<400> SEQUENCE: 486

Thr Val Arg Val Ile Met Thr Cys Trp Leu Ile Val Asp Ile Gly Leu
1               5                   10                  15

Leu Ile Val Ser Ser Val Phe
                20
```